US006753421B2

(12) United States Patent
Stender et al.

(10) Patent No.: US 6,753,421 B2
(45) Date of Patent: Jun. 22, 2004

(54) PROBES FOR THE DETECTION OF MYCOBACTERIA

(75) Inventors: Henrik Stender, Gentofte (DK); Kaare Lund, Frederiksberg (DK); Tina Anderson Mollerup, Leire (DK)

(73) Assignee: Dako A/S, Glostrup (DK)

( * ) Notice: Subject to any disclaimer, the term of this patent is extended or adjusted under 35 U.S.C. 154(b) by 102 days.

(21) Appl. No.: 09/544,934

(22) Filed: Apr. 7, 2000

(65) Prior Publication Data

US 2002/0137035 A1 Sep. 26, 2002

Related U.S. Application Data

(62) Division of application No. 08/943,777, filed on Oct. 3, 1997, now abandoned.

(60) Provisional application No. 60/028,395, filed on Oct. 15, 1996, provisional application No. 60/029,595, filed on Oct. 23, 1996, and provisional application No. 60/045,962, filed on May 8, 1997.

(51) Int. Cl.[7] ........................ C07H 21/02; C07H 21/04; C12Q 1/68

(52) U.S. Cl. .................... 536/24.3; 536/22.1; 536/23.1; 536/24.31; 536/24.32; 536/24.33; 435/6; 435/91.2

(58) Field of Search ................... 435/6, 91.2; 536/22.1, 536/23.1, 24.3, 24.31, 24.32, 24.33

(56) References Cited

U.S. PATENT DOCUMENTS

| | | | | | |
|---|---|---|---|---|---|
| 5,521,300 | A | * | 5/1996 | Shah et al. | 536/24.32 |
| 5,541,308 | A | * | 7/1996 | Hogan et al. | 536/23.1 |
| 5,547,842 | A | | 8/1996 | Hogan et al. | |
| 5,726,021 | A | * | 3/1998 | Britschgi et al. | 435/6 |

FOREIGN PATENT DOCUMENTS

| | | | |
|---|---|---|---|
| EP | 0572120 | | 12/1993 |
| WO | 9636734 | | 5/1995 |
| WO | 9532305 | | 11/1995 |
| WO | 9617956 | | 6/1996 |
| WO | WO 98/15648 | * | 4/1998 |

* cited by examiner

*Primary Examiner*—Jeffrey Fredman
(74) *Attorney, Agent, or Firm*—Finnegan, Henderson, Farabow, Garrett & Dunner, L.L.P.

(57) ABSTRACT

Novel hybridisation assay probes and mixtures of such probes for detecting a target sequence of one or mycobacteria optionally present in a sample. The probes may suitable be directed to target sequences of mycobacterial rDNA, precursor rRNA or rRNA, said probes being capable of forming detectable hybrids. The probes are in particular directed to mycobacterial rDNA, to precursor rRNA, or to 23S, 16S or 5S rRNA. The probes are useful for detecting the organisms in test samples such as sputum, laryngeal swabs, gastric lavage, bronchial washings, biopsies, aspirates, expectorates, body fluids (spinal, pleural, pericardial synovial, blood, pus, bone marrow), urine, tissue sections as well as food samples, soil, air and water samples, and cultures thereof.

9 Claims, 31 Drawing Sheets

```
           130       140       150       160
1093 GGGGAAACCCAGCACGAGTGATGTCGTGCTACCCGCATCT M.tuberculosis
 422 GGGGGAACCCAGCACGAGTGATGTCGTGTTACCCGTATCT M.avium
 422 GGGGGAACCCAGCACGAGTGATGTCGTGTTACCCGTATCT M.paratuberc.
 507 GGGGGAACCCGGCACGAGTGATGTCGTGTCACCCAACGCT M.phlei
 432 GGGGAAACCCAACACGAGTCAGGTCGTGTTACCCGTATCT M.leprae
 207 GGGGAAACCCAGCACGAGTAATGTCGTGTTACCCGTATCT M.gastri
 150 GGGGAAACCCAGCACGAGTGATGTCGTGTTACCCGCATCT M.kansasii
2588 GGGGAAACCCGGCACGAGTGATGTCGTGTCACCAGGCGCT M.smegmatis

                         - - - -

           210       220       230       240
1172 CATCTCAGTACCCGTAGGAGGAGAAAACAATTGTGATTCC M.tuberculosis
 501 CATCTCAGTACCCGTAGGAGAAGAAAACAATTGTGATTCC M.avium
 501 CATCTCAGTACCCGTAGGAGAAGAAAACAATTGTGATTCC M.paratuberc.
 586 CATCTCAGTACCCGTAGAAGAAGAAAACAATTGTGATTCC M.phlei
 511 CATCTCAGTACCCGTAGGAGAAGAAAACAATTGTGATTCC M.leprae
 286 CATCTCAGTACCCGTAGGAGAAGAAAACAAAAGTGATTCC M.gastri
 229 CATCTCAGTACCCGTAGGAGAAGAAAACAAAAGTGATTCC M.kansasii
2667 CATCTCAGTCCCGTAGGAAGAGAAAACAAATGTGATTCC  M.smegmatis

                         - - - -

           330       340       350       360
1289 TGTGGGAG-GATATGTCTCAGCGCTACCCGGCTGAGA-GG M.tuberculosis
 617 TGTGGGATTGATATGTCTCAGCTCTACCTGGCTGAGG-GG M.avium
 617 TGTGGGATTGATATGTCTCAGCTCTACCTGGCTGAGG-GG M.paratuberc.
 703 TGTGGGGCCTGTGTGTCCCATCGTCCGCCGGCGATGGCAG M.phlei
 629 TGTGGGATTGGTATGTCTCAAACTCTACCTGGTTGAGG-GG M.leprae
 404 TGTGGGATCGATAGGTCTCAGCTCTACCCGGCTGAGG-GG M.gastri
 347 TGTGGGATCGATAGGTCTCAGCTCTACCCGGCTGAGG-GG M.kansasii
2785 TGTGGGACCTATGTTTCCGGCCTCTACCGGCTGGGAGGG  M.smegmatis
```

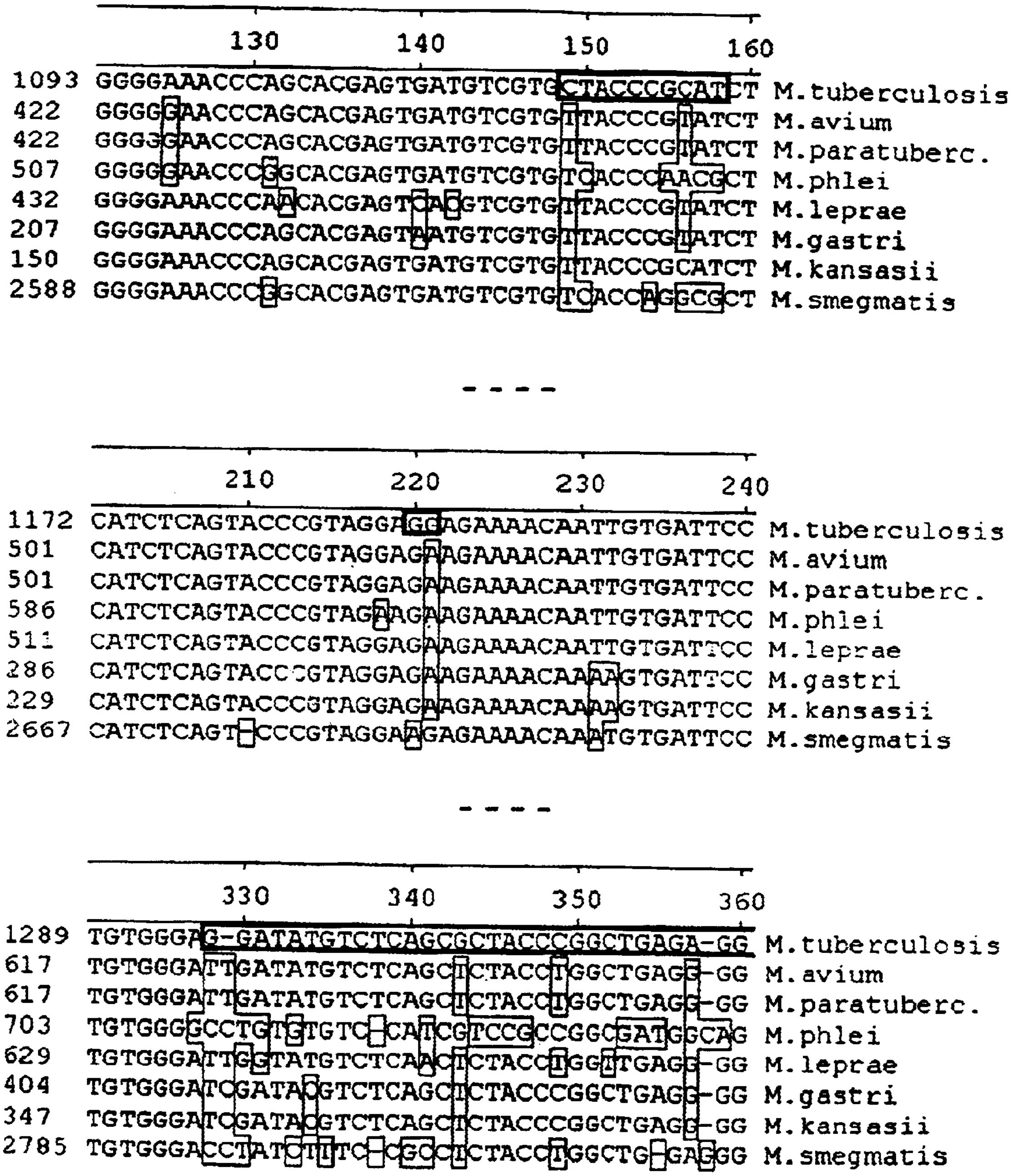

Figure 1A

```
          370       380       390       400
1327 CAGTCAGAAAGTGTCGTGGTTAGCGGAAGTGGCCTGGGAT M.tuberculosis
656  TAGTCAGAAAGTGTCGTGGTTAGCGGAAGTGGCCTGGGAC M.avium
656  TAGTCAGAAAGTGTCGTGGTTAGCGGAAGTGGCCTGGGAC M.paratuberc.
742  TAGTGATAAAGCAGTGTGGTTAGGTGAAGTGGCCTGGGAT M.phlei
668  TAGTCAGAAAGTGCCGTGGTTAGCGGAAATGGCCTGGGAT M.leprae
443  CAGTCAGAAAGTGTCGTGGTTAACGGAAGTGGCCTGGGAT M.gastri
386  CAGTCAGAAAGTGTCGTGGTTAACGGAAGTGGCCTGGGAT M.kansasii
2823 CAGTGAGAAAATGTTGTGGTTAGCGGAAATGGCTTGGGAT M.smegmatis
```

- - - -

```
          450       460       470       480
1406 CGGCACCTGCCTAGTATCAATTCCCGAGTAGCAGCGGGCC M.tuberculosis
735  CGGCACCTGCCTTATATCAACACCCGAGTAGCAGCGGGCC M.avium
735  CGGCACCTGCCTTATATCAACACCCGAGTAGCAGCGGGCC M.paratuberc.
820  TGCTGCC-GCTGTCACAGG--TCCCGAGTAGCAGCGGGCC M.phlei
747  TGGCACCTGCCTTGTATCAATTCCCGAGTAGCAGCGGGCC M.leprae
522  CGGCACCTGCCTTGTATCAATTCCCGAGTAGCAGCGGGCC M.gastri
465  CGGCACCTGCCTTGTATCAATTCCCGAGTAGCAGCGGGCC M.kansasii
2902 CGACGTCTGTCTTGATGGTGTTCCCGAGTAGCAGCGGGCC M.smegmatis
```

```
          490       500       510       520
1446 CGTGGAATCCGCTGTGAATCCGCCGGGACCACCCGGTAAG M.tuberculosis
775  CGTGGAATCTGCTGTGAATCTGCCGGGACCACCCGGTAAG M.avium
775  CGTGGAATCTGCTGTGAATCTGCCGGGACCACCCGGTAAG M.paratuberc.
857  CGTGGAATCTGCTGTGAATCTGCCGGGACCACCCGGTAAG M.phlei
787  CGTGGAATCTGCTGTGAATCTGCCGGGACCACCCGGTAAG M.leprae
562  CGTGGAATCTGCTGTGAATCTGCCGGGACCACCCGGTAAG M.gastri
505  CGTGGAATCTGCTGTGAATCTGCCGGGACCACCCGGTAAG M.kansasii
2942 CGTGGAATCTGCTGTGAATCTGCCGGGACCACCCGGTAAG M.smegmatis
```

Figure 1B

```
                  610       620       630       640
1566 GTACCTGAAACCGTGTGCCTACAATCCGTCAGAGCCTCCT M.tuberculosis
894  GTACCTGAAACCGTGTGCCTACAATCCGTCAGAGCCTCCT M.avium
894  GTACCTGAAACCGTGTGCCTACAATCCGTCAGAGCCTCCT M.paratuberc.
976  GTACCTGAAACCGTGTGCCTACAATCCGTCAAAGCCCTCT M.phlei
907  GTACCTGAAACCGTGTGCCTACAATCCGTCAGAGCCTCTT M.leprae
682  GTACCTGAAACCGTGTGCCTACAATCCGTCAGAGCCCCTT M.gastri
625  GTACCTGAAACCGTGTGCCTACAATCCGTCAGAGCCCTTT M.kansasii
3062 GTACCTGAAACCGTGCGCTTACAATCCGTCAGAGCCCTCG M.smegmatis

                  650       660       670       680
1606 TTTCCTCTCCGGAGGAGGGTGGTGATGGCGTGCCTTTTGA M.tuberculosis
934  C---------------GTGGGGTGATGGCGTGCCTTTTGA M.avium
934  C---------------GTGGGGTGATGGCGTGCCTTTTGA M.paratuberc.
1016 CTT----------GTAGTGGGGTGATGGCGTGCCTTTTGA M.phlei
947  T---------------GTGGGGTGATGGCGTGCTTTTTGA M.leprae
722  T---------------GTGGGGTGATGGCGTGCCTTTTGA M.gastri
665  C---------------GTGGGGTGATGGCGTGCCTTTTGA M.kansasii
3102 ACGTGT----------GTGGGGTGATGGCGTGCCTTTTGA M.smegmatis

                  690       700       710       720
1646 AGAATGAGCCTGCGAGTCAGGGACATGTCGCAAGGTTAAC M.tuberculosis
4    AGAATGAGCCTGCGAGTCAGGGACATGTCGCAAGGTTAAC M.bovis
959  AGAATGAGCCTGCGAGTCAGGGACACGTCGCGAGGTTAAC M.avium
23   AGAATGAGCCTGCGAGTCAGGGACACGTCGCGAGGTTAAC M.intracellular
959  AGAATGAGCCTGCGAGTCAGGGACACGTCGCGAGGTTAAC M.paratuberc.
1046 AGAATGAGCCTGCGAGTCAGGGACATGTCGCGAGGTTAAC M.phlei
972  AGAATGAGCCTGCGAGTCAGGGACATGTCGCGAGGTTAAC M.leprae
747  AGAATGAGCCTGCGAGTCAGGGACATGTCGCGAGGTTAAC M.gastri
690  AGAATGAGCCTGCGAGTCAGGGACATGTCGCGAGGTTAAC M.kansasii
3132 AGAATGAGCCTGCGAGTCAGGGACATGTCGCGAGGTTAAC M.smegmatis
```

Figure 1C

```
                770       780       790       800
1726 CGACCCACACGCGCATACGCGCGTGTGAATAGTGGCGTGT M.tuberculosis
84   CGACCCACACGCGCATACGCGCGTGTGAATAGTGGCGTGT M.bovis
1039 CG-----CATCCCCTTTGGGGTGT------AGTGGCGTGT M.avium
103  CG-----CATCCCCTTTGGGGTGT------AGTGGCGTGT M.intracellulai
1039 CG-----CATCCCTTTTGGGGTGT------AGTGGCGTGT M.paratuberc.
1126 CGTATCCAACCTGTTGGGGTTGGTGT----AGTGGTGTGT M.phlei
1052 CGTAT--CACGTGTGAGCGTGTGT------AGTGGCGTGT M.leprae
827  CGTAT--CACGCGTAAGCGTGTGT------AGTGGCGTGT M.gastri
770  CGTAT--CGCGCGCGAGCGTGTGT------AGTGGCGTGT M.kansasii
3212 CGTAT--CCACACAAGAGTGTGTGGTGT--AGTGGTGTGT M.smegmatis
```

- - - -

```
                970       980       990      1000
1926 ATTTAGGTGCAGCGTTGCGTGGTTCACCGCGGAGGTAGAG M.tuberculosis
1228 ATTTAGGTGCAGCGTTGCGTGGTTCACCACGGAGGTAGAG M.avium
1228 ATTTAGGTGCAGCGTTGCGTGGTTCACCACGGAGGTAGAG M.paratuberc.
1322 ATTTAGGTGCAGCGTCGCATGTTTCTTATCGGAGGTAGAG M.phlei
1244 ATTTAGGTGCAGCGTTGCGTGGTTCACCACGGAGGTAGAG M.leprae
1019 ATTTAGGTGCAGCGTTGCGTGTTTCACCACGGAGGTAGAG M.gastri
962  ATTTAGGTGCAGCGTTGCGTGTTTCACCACGGAGGTAGAG M.kansasii
3408 ATTTAGGTGCAGCGTCGCATGTTTCTTGCCGGAGGTAGAG M.smegmatis
```

- - - -

```
               1050      1060      1070      1080
2005 CAGCCAAACTCCGAATGCCG-TGGTG-TA-AAGCGTGGCA M.tuberculosis
1307 CAGCCAAACTCCGAATGCCG-TGGTG-TAAAAGCGTGGCA M.avium
1307 CAGCCAAACTCCGAATGCCG-TGGTG-TAAAAGCGTGGCA M.paratuberc.
1401 CAGCCAAACTCCGAATGCCGATAAG--TGAAAGTGTGGCA M.phlei
1323 CAGCCAAACTCCGAATGCCG-TGGTT-TAAAAGCGTGGCA M.leprae
1098 CAGCCAAACTCCGAATGCCG-TGGTG-TATA-GCGTGGCA M.gastri
1041 CAGCCAAACTCCGAATGCCG-TGGTG-TATA-GCGTGGCA M.kansasii
3486 CAGCCAAACTCCGAATGCCGGTAAGGCCAAGAGTGCGGAA M.smegmatis
```

Figure 1D

```
                1130      1140      1150      1160
2082 ACAGCCCAGATCGCCGGCTAAGGCCCCCAAGCGTGTGCTA M.tuberculosis
1385 ACAGCCCAGATCGCCGGCTAAGGCCCCTAAGCGTGTGCTA M.avium
1385 ACAGCCCAGATCGCCGGCTAAGGCCCCTAAGCGTGTGCTA M.paratuberc.
1479 ACAGCCCAGATCGCCGGCTAAGGCCCCTAAGCGTGTGCTA M.phlei
1401 ACAGCCCAGATCGCCGGCTAAGGCCCCTAAGCGTGTGCTA M.leprae
1175 ACAGCCCAGATCGCCGGCTAAGGCCCCAAAGCGTGTGCTA M.gastri
1118 ACAGCCCAGATCGCCGGCTAAGGCCCCAAAGCGTGTGCTA M.kansasii
3566 ACAGCCCAGATCGCCGGTTAAGGCCCCTAAGCGTTTGTTA M.smegmatis
```

- - - -

```
                1290      1300      1310      1320
2241 CTCAAGCACACCGCCGAAGCCGCGGCACATCCACCTTGT- M.tuberculosis
1544 CTCAAGCACACCGCCGAAGCCGCGGCACATTCATCTT-TA M.avium
1544 CTCAAGCACACCGCCGAAGCCGCGGCACATTCATCTT-TA M.paratuberc.
1638 CTCAAGCACACCGCCGAAGCCGCGGCA--ATCAGCGTTTG M.phlei
1560 CTCAAGCACACCGCCGAAGCCGCGGCACATTCACCTTCTA M.leprae
1334 CTCAAGCACACCGCCGAAGCCGCGACA-----ACCGC--A M.gastri
1277 CTCAAGCACACCGCCGAAGCCGCGACA-----ACCGC--A M.kansasii
3726 TTCAAGCACACCGCCGAAGCCGCGGAA--GCCAACGTTTG M.smegmatis

                1330      1340      1350      1360
2280 -GGTGGGTGTGGGTAGGGGAGCGTCCCTCATTCAGCGAAG M.tuberculosis
1583 CGGTGGATGTGGGTAGGGGAGCGTCCCCCATTCAGCGAAG M.avium
1583 CGGTGGATGTGGGTAGGGGAGCGTCCCCCATTCAGCGAAG M.paratuberc.
1676 TGGCTGGTGTGGGTAGGGGAGCGTCCTGCATCCGGTGAAG M.phlei
1600 GGGTGGATGTGGGTAGGGGAGCGTTCCTCATTCAGCGAAG M.leprae
1367 AGGT-----TGGGTAGGGGAGCGTCCCTCATTCAGCGAAG M.gastri
1310 AGGT-----TGGGTAGGGGAGCGTCCCTCATTCAGCGAAG M.kansasii
3764 TT-------TGGGTAGGGGAGCGTCCTG-ATCCGGTGAAG M.smegmatis
```

Figure 1E

```
                 1370      1380      1390      1400
2319 CCACCGGGTGACCGGTGGTGGAGGGTGGGGGAGTGAGAAT M.tuberculosis
1623 CT-CCGGGTGACCGGTGGTGGAGGGTGGGGGAGTGAGAAT M.avium
1623 CT-CCGGGTGATCGGTGGTGGAGGGTGGGGGAGTGAGAAT M.paratuberc.
1716 CCGCCGAGTGATCGGTGGTGGAGGGTGTGGGAGTGAGAAT M.phlei
1640 CCTCCGGGTAACCGGTGGTGGAGGGTGGGGAAGTGAGAAT M.leprae
1402 CCGCCGGGTGACCGGTGGTGGAGGATGGGGGAGTGAGAAT M.gastri
1345 CTGCCGGGTGACCGGTGGTGGAGGATGGGGGAGTGAGAAT M.kansasii
3796 CCGCCGAGTATCGAGTGGTGGAGGGTGTGGGAGTGAGAAT M.smegmatis

                 1410      1420      1430      1440
2359 GCAGGCATGAGTAGCGACAAGGCAAGTGAGAACCTTGCCC M.tuberculosis
1662 GCAGGCATGAGTAGCGATAAGGCAAGTGAGAACCTTGCCC M.avium
1662 GCAGGCATGAGTAGCGATAAGGCAAGTGAGAACCTTGCCC M.paratuberc.
1756 GCAGGCATGAGTAGCGATAAGGCAAGTGAGAACCTTTCCC M.phlei
1680 GCAGGCATGAGTAGCGATAAGGCAAGTGAGAACCTTGCCC M.leprae
1442 GCAGGCATGAGTAGCGATAAGGCAAGTGAGAACCTTGCCC M.gastri
1385 GCAGGCATGAGTAGCGATAAGGCAAGTGAGAACCTTGCCC M.kansasii
3836 GCAGGCATGAGTAGCGATTAGGCAAGTGAGAACCTTCCCC M.smegmatis

- - - -

                 1570      1580      1590      1600
2519 CGCCCGTGACGAATCA-GCGGTACTAACCACCCAAAACCG M.tuberculosis
1821 CGTCCCTGATGAATCA-GCGGTACTAACCACCCAAAACCG M.avium
1821 CGTCCCTGATGAATCA-GCGGTACTAACCACCCAAAACCG M.paratuberc.
1915 CGTCCCTGATGAATCTCATTCTGCTAACCACCCAAAACCT M.phlei
1840 CGCCCGTGATGAATCA-GCGGTACTCACCACCCAAAACCG M.leprae
1602 CGCCCGTGATGAATCA-GCGGTACTAACCACCCAAAACCG M.gastri
1545 CGCCCGTGATGAATCA-GCGGTACTAACCACCCAAAACCG M.kansasii
3996 CGTCCATGATGAATCA-GCGGTACTAACCATCCAAAACCA M.smegmatis
```

Figure 1F

```
                  1610      1620      1630      1640
2558 GAT-CGATCAC-TCCCCTTCGGGGG-TGTGGAGTTC-TGG M.tuberculosis
1860 GAT-CGACCAT-TCCCCTTCGGGGGC-GTGGCGATT-CGG M.avium
1860 GAT-CGACCAT-TCCCCTTCGGGGGC-GTGGCGATT-CGG M.paratuberc.
1955 GGC-CGATC--ATCC--TTCGGGG---GTGACGGTTG-GG M.phlei
1879 GAT-CGACCATATCCCCTTCGGGGGCTATGGAGGTT-CGG M.leprae
1641 GAT-CGATCAC-TCCCCTTCGGGGGA-GTGGAGGTC-TGG M.gastri
1584 GAT-CGATCAC-TCCCCTTCGGGGGC-GTGGAGGTC-TGG M.kansasii
4035 ACCGTGACCGCACCT--TTCGGGG--TGTGGCGTTGGTGG M.smegmatis

                  1650      1660      1670      1680
2594 GGCTGCGTGGGAACTTCGCTGGTAGTAGTCAAGCGAAGGG M.tuberculosis
1896 GGCTGCGTGGGACCTTCGCTGGTAGTAGTCAAGCAATGGG M.avium
1896 GGCTGCGTGGGACCTTCGCTGGTAGTAGTCAAGCAATGGG M.paratuberc.
1986 GGCTGCGTGGGACCCG-GTGGGTAGTAGTCAAGCGATGGG M.phlei
1917 GGCTGCGTGGGAACTTCGTTGGTAGTAGTCAAGCGATGGG M.leprae
1677 GGCTGCGTGGAGCCTTCGCTGGTAGTAGTCAAGCGATGGG M.gastri
1620 GGCTGCGTGGAGCCTTCGCTGGTAGTAGTCAAGCGATGGG M.kansasii
4071 GGCTGCATGGGACCTTCGTTGGTAGTAGTCAAGCGATGGG M.smegmatis

                  1690      1700      1710      1720
2634 -GTGACGCAGGAAGGTAGCCGTACCAGTCAGTGGTAACA- M.tuberculosis
1936 -GTGACGCAGGAAGGCAGCCGTACCAGTCAGTGGTAATA- M.avium
1936 -GTGACGCAGGAAGGCAGCCGTACCAGTCAGTGGTAATA- M.paratuberc.
2025 -GTGACGCAGGAAGGTAGCCGTACCAGTCAGTGGTAATA- M.phlei
1957 -GTGACGCAGGAAGGTAGCCGTACCAGTCAGTGGTAATA- M.leprae
1717 -GTGACGCAGGAAGGCAGCCGTACCAGTCAGTGGTAATA- M.gastri
1660 -GTGACGCAGGAAGGCAGCCGTACCAGTCAGTGGTAATA- M.kansasii
4111 -GTGACGCAGGAAGGTAGCCGTACCGGTCAGTGGTAATA- M.smegmatis
```

Figure 1G

```
           1730      1740      1750      1760
2672 -CTGGGGCAAGCCGGTAGGGAGAGCGATAGGCAAATCCGT M.tuberculosis
1974 -CTGGGGCAAGCCCGTAG--AGAGCGATAGGCAAATCCGT M.avium
1974 -CTGGGGCAAGCCCGTAG--AGAGCGATAGGCAAATCCGT M.paratuberc.
2063 -CCGGGGTAAACCTGTAGGGCGAGTGATAGGCAAATCCGT M.phlei
1995 -CTGGAGCAAGCCCGTAGGGAGAGCGATAGGCAAATCCGT M.leprae
1755 -CTGGGGCAAGCCAGTAGGGAGAGCGATAGGCAAATCCGT M.gastri
1698 -CTGGGGCAAGCCAGTAGGGAGAGCGATAGGCAAATCCGT M.kansasii
4149 -CCGGCGTAAGCCTGTAGGGAGTCAGATAGGTAAATCCGT M.smegmatis
```

- - - -

```
           1970      1980      1990      2000
2908 AGGGGGACCGGAATATCGTGAACACCCTTGCGGTGGGAGC M.tuberculosis
2208 AGGGGGCCCGGAATACCGTGAACACCCTTGCGGTGGGAGC M.avium
2208 AGGGGGCCCGGAATACCGTGAACACCCTTGCGGTGGGAGC M.paratuberc.
2298 AGGGGGACCCACGTACCGTGAGGGCTCTTGCGGCGGCAGC M.phlei
2231 AGGGGGGCCGGAATATCGTGAACACCCTTGCGGTGGGAGC M.leprae
1910                                          M.gastri
1934 AGGGGGACCGGAATACCGTGAACACCCTTGCGGTGGGAGC M.kansasii
4385 AGGGGGACCCACATGGCGTGTAAGCCTTTACGGCCCAAGC M.smegmatis
```

- - - -

```
           2410      2420      2430      2440
3345 ACCTCGACGCCAGTTGGGGCGGAGTCGTTGTTGAAATACC M.tuberculosis
284  ACCTCGACGCCAGTTGGGGCGGAGTCGTTGTTGAAATACC M.bovis
2645 GCACAGACGCCAGTTTGTGTGGAGTCGTTGTTGAAATACC M.avium
393  ATACAGACGCCAGTTTGTATGGAGTCGTTGTTGAAATACC M.intracellulare
2645 GCACAGACGCCAGTTTGTGTGGAGTCGTTGTTGAAATACC M.paratuberc.
2737 GCTCGGACGCCAGTTCGGGTGGAGTCGTTGTTGAAATACC M.phlei
2668 ACTTCGACGCTAGTTGGGGTGGAGTCGTTGTTGAAATACC M.leprae
1910                                          M.gastri
2372 ACCTCAACGCCAGTTGGGGTGGAGTCGTTGTTGAAATACC M.kansasii
4822 GCTCACACGCCAGTGTGGGTGGAGTCGTTGTTGAAATACC M.smegmatis
```

Figure 1H

```
               2450      2460      2470      2480
3385 ACTCTGATCGTATTGGGCATCTAACCTCGAACCCTGAATC M.tuberculosis
324  ACTCTGATCGTATTGGGCATCTAACCTCGAACCCTGAATC M.bovis
2685 ACTCTGATCGTATTGGACACCTAACGTCGAACCCT-TATC M.avium
433  ACTCTGATCGTATTGGACACCTAACGTCGAACCCT-TATC M.intracellulare
2685 ACTCTGATCGTATTGGACACCTAACGTCGAACCCT-TATC M.paratuberc.
2777 ACTCTGATCGTATTGGGCCTCTAACCTCGGACCGTGGATC M.phlei
2708 ACTCTGATTGTATTGAACATCTAACCTCGAACCGTATATC M.leprae
1910                                          M.gastri
2412 ACTCTGATCGTATTGGACACCTAACGTCGAACCCTGAATC M.kansasii
4862 ACTCTGATCGTATTGGGCCTCTAACCTCGGACCGTATATC M.smegmatis

               2490      2500      2510      2520
3425 GGGTTTAGGGACAGTGCCTGGCGGGTAGTTTAACTGGGGC M.tuberculosis
364  GGGTTTAGGGACAGTGCCTGGCGGGTAGTTTAACTGGGGC M.bovis
2724 GGGTTCACGGACAGTGCCTGGCGGGTAGTTTAACTGGGGC M.avium
472  GGGTTCACGGACAGTGCCTGGCGGGTAGTTTAACTGGGGC M.intracellulare
2724 GGGTTCACGGACAGTGCCTGGCGGGTAGTTTAACTGGGGC M.paratuberc.
2817 CGGTTCAGGGACAGTGCCTGGTGGGTAGTTTAACTGGGGC M.phlei
2748 CGGTTTAGGGACAGTGCCTGGCGGGTAGTTTAACTGGGGC M.leprae
1910                                          M.gastri
2452 GGGTTCACGGACAGTGCCTGGCGGGTAGTTTAACTGGGGC M.kansasii
4902 CGGTTCAGGGACAGTGCCTGGTGGGTAGTTTAACTGGGGC M.smegmatis

- - - -

               2930      2940      2950      2960
3864 AGTACGAGAGGACCGGGACGGACGAACCTCTGGTGCACCA M.tuberculosis
3163 AGTACGAGAGGACCGGGACGGACGAACCTCTGGTATACCA M.avium
3163 AGTACGAGAGGACCGGGACGGACGAACCTCTGGTATACCA M.paratuberc.
3256 AGTACGAGAGGACCGGGACGGACGAACCTCTGGTATACCA M.phlei
3187 AGTACGAGAGGACCGGGACGGACGAACCTCTGGTATACCA M.leprae
1910                                          M.gastri
2891 AGTACGAGAGGACCGGGACGGACGAACCTCTAGTGCACCA M.kansasii
5342 AGTACGAGAGGACCGGGACGGACGAACCTCTGGTATACCA M.smegmatis
```

Figure 1I

```
                 2970      2980      2990      3000
3904 GTTGTCCCGCCAGGGGCACCGCTGGATAGCCACGTTCGGT M.tuberculosis
3203 GTTGTCCCACCAGGGGCACGGCTGGATAGCCACGTTCGGA M.avium
3203 GTTGTCCCACCAGGGGCACGGCTGGATAGCCACGTTCGGA M.paratuberc.
3296 GTTGTCCCACCAGGGGCACCGCTGGATAGCCACGTTCGGA M.phlei
3227 GTTGTCTCACCAGGGGCACCGCTGGATAGCCACGTTCGGA M.leprae
1910                                          M.gastri
2931 GTTGTCCCACCAGGGGCACCGCTGGATAGCTACGTTCGGA M.kansasii
5382 GTTGTCCCACCAGGGGCACGGCTGGATAGCCACGTTCGGA M.smegmatis
```

```
                 3010      3020      3030      3040
3944 CAGGATAACCGCTGAAAGCATCTAAGCGGGAAACCTTCTC M.tuberculosis
3243 CAGGATAACCGCTGAAAGCATCTAAGCGGGAAACCTTCTC M.avium
3243 CAGGATAACCGCTGAAAGCATCTAAGCGGGAAACCTTCTC M.paratuberc.
3336 CAGGATAACCGCTGAAAGCATCTAAGCGGGAAACCTCTTC M.phlei
3267 CAAGATAACCGCTGAAAGCATCTAAGCGGGAAACCTTCTC M.leprae
1910                                          M.gastri
2971 CAGGATAACCGCTGAAAGCATCTAAGCGGGAAACCTTCTC M.kansasii
5422 CAGGATAACCGCTGAAAGCATCTAAGCGGGAAACCTCTTC M.smegmatis
```

- - - -

```
                 3090      3100      3110      3120
4023 CCCGC-AGAACACGGGTTCAATAGGTCAGACCTGGAAGCT M.tuberculosis
609  CCCGC-AGAACACGGGTTCAATAGGTCAGACCTGGAAGCT M.bovis
3322 CCCGC-AGACCACGGGATTGATAGGCCAGACCTGGAAGCT M.avium
677  CCCGC-AGACCACGGGTTCGATAGGCCAGACCTGGAAGCT M.intracellulare
3322 CCCGC-AGATCACGGGATTGATAGGCCAGACCTGGAAGCT M.paratuberc.
3415 CCCGC-AGACCACGGGATCGATAGACCAGACCTGCACGCA M.phlei
3309                                          M.leprae
1910                                          M.gastri
3050 CCCGC-AGAACACGGGTTCGATAGGCCAGACCTGGAAGCT M.kansasii
5501 CCCGC-AGACCACGGGATTGATAGACCAGACCTGGAAGCC M.smegmatis
```

Figure 1J

```
                50        60        70        80
2    GCGGCGTGCTTAACACATGCAAGTCGAACGGAAAGGTCTC M.tuberculosis
141  GCGGCGTGCTTAACACATGCAAGTCGAACGGAAAGGTCTC M.bovis
39   GCGGCGTACTTAACACATGCAAGTCGAACGGAAAGGCCTC M.avium
1    ---------TTAACACATGCAAGTAGAACGGAAAGACCCC M.intracellulare
39   GCGGCGTGCTTAACACATGCAAGTCGAACGGAAAGGCCTC M.paratuberc.
2    GCGGCGTGCTTAACAAATGCAAGTCGAACGGAAAGGCCCC M.scrofulaceum
40   GCGGCGTGCTTAACACATGCAAGTCGAACGGAAAGGTCTC M.leprae
2    -CGGCGTGCTTAACACATGCAAGTCGAACGGAAAGGTCTC M.kansasii
2    GCGGCGTGCTTAACACATGCAAGTCGAACGGAAAGGTCTC M.gastri
40   GCGGCGTGCTTAACACATGCAAGTCGAACGGTAAGGCTTC M.gordonae
1    -----GTGCTTAACACATGCAAGTCGAACGGAAAGGTCTC M.marinum

                90        100       110       120
42   T------------TCGGAGATACTCGAGTGGCGAACGGGT M.tuberculosis
181  T------------TCGGAGATACTCGAGTGGCGAACGGGT M.bovis
79   T------------TCGGAGGTACTCGAGTGGCGAACGGGT M.avium
32   T------------TCGGGG-TACTCGAGTGGCGAACGGGT M.intracellulare
79   T------------TCGGAGGTACTCGAGTGGCGAACGGGT M.paratuberc.
42   T------------TCGGGGGTACTCGAGTGGCGAACGGGT M.scrofulaceum
80   TAAAAAATCTTTTTTTAGAGATACTCGAGTGGCGAACGGGT M.leprae
41   T------------TCGGAGACACTCGAGTGGCGAACGGGT M.kansasii
42   T------------TCGGAGACACTCGAGTGGCGAACGGGT M.gastri
80   -------------------GGGGTACACGAGTGGCGAACGGGT M.gordonae
36   T------------TCGGAGATACTCGAATGGCGAACGGGT M.marinum

                130       140       150       160
70   GAGTAACACGTGGGTGATCTGCCCTGCACTTC-GGGATAA M.tuberculosis
209  GAGTAACACGTGGGTGATCTGCCCTGCACTTC-GGGATAA M.bovis
107  GAGTAACACGTGGGCAATCTGCCCTGCACTTC-GGGATAA M.avium
59   GAGTAACACGTGGGCAATCTGCCCTGCACTTC-GGGATAA M.intracellulare
107  GAGTAACACGTGGGCAATCTACCCTGCACTTC-GGGATAA M.paratuberc.
70   GAGTAACACGTGGGCAATCTGCCCTGCACTTC-GGGATAA M.scrofulaceum
120  GAGTAACACGTGGGTAATCTGCCCTGCACTTCAGGGATAA M.leprae
69   GAGTAACACGTGGGCAATCTGCCCTGCACACC-GGGATAA M.kansasii
70   GAGTAACACGTGGGCAATCTGCCCTGCACACC-GGGATAA M.gastri
104  GAGTAACACGTGGGTAATCTGCCCTGCACATC-GGGATAA M.gordonae
64   GAGTAACACGTGGGCGATCTGCCCTGCACTTC-GGGATAA M.marinum
```

Figure 2A

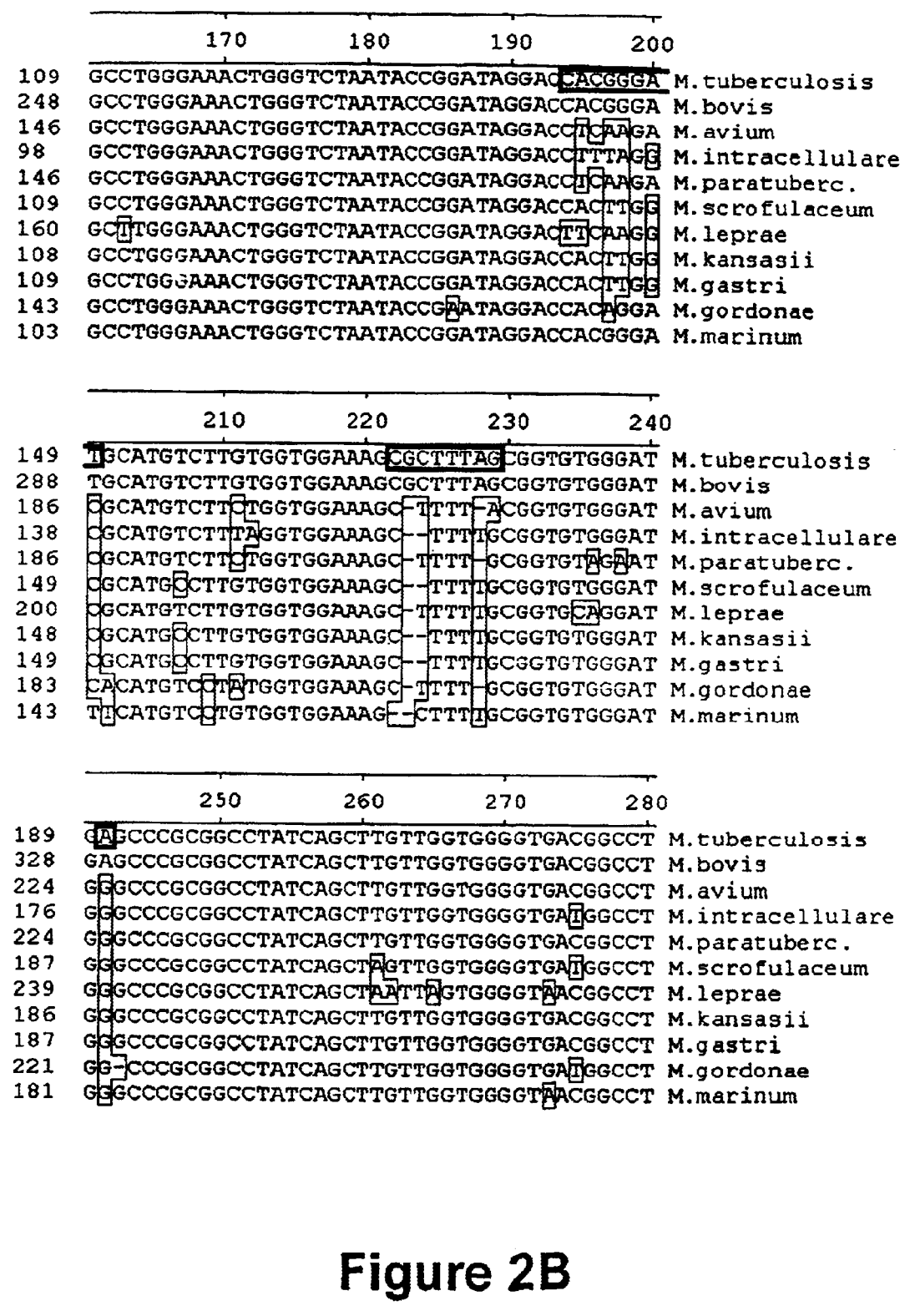

```
              170       180       190       200
109  GCCTGGGAAACTGGGTCTAATACCGGATAGGACCACGGGA M.tuberculosis
248  GCCTGGGAAACTGGGTCTAATACCGGATAGGACCACGGGA M.bovis
146  GCCTGGGAAACTGGGTCTAATACCGGATAGGACCTCAAGA M.avium
98   GCCTGGGAAACTGGGTCTAATACCGGATAGGACCTTTAGG M.intracellulare
146  GCCTGGGAAACTGGGTCTAATACCGGATAGGACCTCAAGA M.paratuberc.
109  GCCTGGGAAACTGGGTCTAATACCGGATAGGACCACTTGG M.scrofulaceum
160  GCTTGGGAAACTGGGTCTAATACCGGATAGGACTTCAAGG M.leprae
108  GCCTGGGAAACTGGGTCTAATACCGGATAGGACCACTTGG M.kansasii
109  GCCTGGGAAACTGGGTCTAATACCGGATAGGACCACTTGG M.gastri
143  GCCTGGGAAACTGGGTCTAATACCGAATAGGACCACAGGA M.gordonae
103  GCCTGGGAAACTGGGTCTAATACCGGATAGGACCACGGGA M.marinum

              210       220       230       240
149  TGCATGTCTTGTGGTGGAAAGCGCTTTAGCGGTGTGGGAT M.tuberculosis
288  TGCATGTCTTGTGGTGGAAAGCGCTTTAGCGGTGTGGGAT M.bovis
186  CGCATGTCTTCTGGTGGAAAGC-TTTT-ACGGTGTGGGAT M.avium
138  CGCATGTCTTTAGGTGGAAAGC--TTTTGCGGTGTGGGAT M.intracellulare
186  CGCATGTCTTCTGGTGGAAAGC-TTTT-GCGGTGTAGAAT M.paratuberc.
149  CGCATGCCTTGTGGTGGAAAGC--TTTTGCGGTGTGGGAT M.scrofulaceum
200  CGCATGTCTTGTGGTGGAAAGC-TTTTTGCGGTGCAGGAT M.leprae
148  CGCATGCCTTGTGGTGGAAAGC--TTTTGCGGTGTGGGAT M.kansasii
149  CGCATGCCTTGTGGTGGAAAGC--TTTTGCGGTGTGGGAT M.gastri
183  CACATGTCCTATGGTGGAAAGC-TTTT-GCGGTGTGGGAT M.gordonae
143  TTCATGTCCTGTGGTGGAAAG--CTTTTGCGGTGTGGGAT M.marinum

              250       260       270       280
189  GAGCCCGCGGCCTATCAGCTTGTTGGTGGGGTGACGGCCT M.tuberculosis
328  GAGCCCGCGGCCTATCAGCTTGTTGGTGGGGTGACGGCCT M.bovis
224  GGGCCCGCGGCCTATCAGCTTGTTGGTGGGGTGACGGCCT M.avium
176  GGGCCCGCGGCCTATCAGCTTGTTGGTGGGGTGATGGCCT M.intracellulare
224  GGGCCCGCGGCCTATCAGCTTGTTGGTGGGGTGACGGCCT M.paratuberc.
187  GGGCCCGCGGCCTATCAGCTAGTTGGTGGGGTGATGGCCT M.scrofulaceum
239  GGGCCCGCGGCCTATCAGCTAATTAGTGGGGTAACGGCCT M.leprae
186  GGGCCCGCGGCCTATCAGCTTGTTGGTGGGGTGACGGCCT M.kansasii
187  GGGCCCGCGGCCTATCAGCTTGTTGGTGGGGTGACGGCCT M.gastri
221  GG-CCCGCGGCCTATCAGCTTGTTGGTGGGGTGATGGCCT M.gordonae
181  GGGCCCGCGGCCTATCAGCTTGTTGGTGGGGTAACGGCCT M.marinum
```

Figure 2B

```
                 450       460       470       480
389  AAACCTCTTTCACCATCGACGAAGGTCCGGGTTCTCTCGG M.tuberculosis
528  AAACCTCTTTCACCATCGACGAAGGTCCGGGTTCTCTCGG M.bovis
424  AAACCTCTTTCACCATCGACGAAGGTCCGGGTTTTCTCGG M.avium
376  AAACCTCTTTCACCATCGACGAAGGTCCGGGTTTTCTCGG M.intracellulare
424  AAACCTCTTTCACCATCGACGAAGGTCCGGGTTTTCTAGG M.paratuberc.
387  AAACCTCTTTCACCATCGACGAAGGCTCA---CTTTGTGG M.scrofulaceum
439  AAACCTCTTTCACCATCGACGAAGGTCTGGGAATTCTCGG M.leprae
386  AAACCTCTTTCACCATCGACGAAGGTCCGGGTTCTCTCGG M.kansasii
387  AAACCTCTTTCACCATCGACGAAGGTCCGGGTTCTCTCGG M.gastri
420  AAACCTCTTTCACCATCGACGAAGGTCCGGGTTTTCTCGG M.gordonae
381  AAACCTCTTTCACCATCGACGAAGGTTCGGGTTTTCTCGG M.marinum
```

- - - -

```
                 1130      1140      1150      1160
1069 TCTCATGTTGCCAGCACGTAATGGTGGGGACTCGTGAGAG M.tuberculosis
1208 TCTCATGTTGCCAGCACGTAATGGTGGGGACTCGTGAGAG M.bovis
1104 TCTCATGTTGCCAGCGGGTAATGCCGGGGACTCGTGAGAG M.avium
1056 TCTCATGTTGCCAGCGGGTAATGCCGGGGACTCGTGAGAG M.intracellulare
1098 TCTCATGTTGCCAGCGGGTAATGCAGGGGACTCGTGAGAG M.paratuberc.
1064 TCTCATGTTGCCAGCGGGTAATGCCGGGGACTCGTGAGAG M.scrofulaceum
1119 TCTCATGTTGCCAGCACGTAATGGTGGGGACTCGTGAGAG M.leprae
1066 TCTCATGTTGCCAGCGGGTAATGCCGGGGACTCGTGAGAG M.kansasii
1067 TCTCATGTTGCCAGCGGGTAATGCCGGGGACTCGTGAGAG M.gastri
1100 TCTCATGTTGCCAGCGGGTAATGCCGGGGACTCGTGAGAG M.gordonae
1061 TCTCATGTTGCCAGCACGTAATGGTGGGGACTCGTGAGAG M.marinum
```

- - - -

```
                 1250      1260      1270      1280
1189 CAATGGCCGGTACAAAGGGCTGCGATGCCGCGAGGTTAAG M.tuberculosis
1328 CAATGGCCGGTACAAAGGGCTGCGATGCCGCGAGGTTAAG M.bovis
1224 CAATGGCCGGTACAAAGGGCTGCGATGCCGTAAGGTTAAG M.avium
1176 CAATGGCCGGTACAAAGGGCTGCGATGCCGCAAGGTTAAG M.intracellulare
1218 CAATGGCCGGTACAAAGGGCTGCGATGCCGTAAGGTTAAG M.paratuberc.
1184 CAATGGCCGGTACAAAGGGCTGCGATGCCGCAAGGTTAAG M.scrofulaceum
1239 CAATGGCCGGTACAAAGGGCTGCGATGCCGCAAGGTTAAG M.leprae
1186 CAATGGCCGGTACAAAGGGCTGCGATGCCGCGAGGTTAAG M.kansasii
1187 CAATGGCCGGTACAAAGGGCTGCGATGCCGCGAGGTTAAG M.gastri
1220 CAATGGCCGGTACAAAGGGCTGCGATGCCGCGAGGTTAAG M.gordonae
1181 CAATGGCCGGTACAAAGGGCTGCGATGCCGCGAGGTTAAG M.marinum
```

Figure 2C

```
                1290      1300      1310      1320
1229 CGAATCCTTA-AAAGCCGGTCTCAGTTCGGATCGGGGTCT M.tuberculosis
1368 CGAATCCTTA-AAAGCCGGTCTCAGTTCGGATCGGGGTCT M.bovis
1264 CGAATCCTTTTAAAGCCGGACTCAGTTCGGATTGGGGTCT M.avium
1216 CGAATCCTTTTAAAGCCGGTCTCAGTTCGGATTGGGGTCT M.intracellulare
1258 CGAATCCTTTTAAAGCCGGACTCAGTTCGGATTGGGGTCT M.paratuberc.
1224 CGAATCCTTTTAAAGCCGGTCTCAGTTCGGATCGGGGTCT M.scrofulaceum
1279 CGAATCCTTTTAAAGCCGGTCTCAGTTCGGATCGGGGTCT M.leprae
1226 CGAATCCTTTTAAAGCCGGTCTCAGTTCGGATCGGGGTCT M.kansasii
1227 CGAATCCTTTTAAAGCCGGTCTCAGTTCGGATCGGGGTCT M.gastri
1260 CGAATCCTTTTAAAGCCGGTCTCAGTTCGGATCGGGGTCT M.gordonae
1221 CGAATCCTTT-AAAGCCGGTCTCAGTTCGGATCGGGGTCT M.marinum

                1330      1340      1350      1360
1268 GCAACTCGACCCCGTGAAGTCGGAGTCGCTAGTAATCGCA M.tuberculosis
1407 GCAACTCGACCCCGTGAAGTCGGAGTCGCTAGTAATCGCA M.bovis
1304 GCAACTCGACCCCATGAAGTCGGAGTCGCTAGTAATCGCA M.avium
1256 GCAACTCGACCCCATGAAGTCGGAGTCGCTAGTAATCGCA M.intracellulare
1298 GCAACTAGACCCAATGAAGTCGGAGTCGCTAGTAATCGCA M.paratuberc.
1264 GCAACTCGACCCCGTGAAGTCGGAGTCGCTAGTAATCGCA M.scrofulaceum
1319 GCAACTCGACCCCGTGAAGTCGGAGTCGCTAGTAATCGCA M.leprae
1266 GCAACTCGACCCCGTGAAGTCGGAGTCGCTAGTAATCGCA M.kansasii
1267 GCAACTCGACCCCGTGAAGTCGGAGTCGCTAGTAATCGCA M.gastri
1300 GCAACTCGACCCCGTGAAGTCGGAGTCGCTAGTAATCGCA M.gordonae
1260 GCAACTCGACCCCGTGAAGTCGGAGTCGCTAGTAATCGCA M.marinum
```

Figure 2D

```
              50         60         70         80
128   TTCCGAACCCGGAAGCTAAGCCTGCCAGCGCCGATGATAC  M.tuberculosis
39    TGCCGAACCCGGAAGCTAAGCCTGCCAGCGCCGATGATAC  M.bovis
41    TCCCGAACCCGGAAGCTAAGCCTGCCAGCGCCAATGATAC  M.phlei
3559  TACCGAACCCGGAAGCTAAGCCTGTCAGCGCCGATGATAC  M.leprae
5743  TGCCGAACCCGGAAGCTAAGCCTGCCAGCCCCGATGATAC  M.smegmatis

              90        100        110        120
168   TGCCCCTCCGGG----TGGAAAAGTAGGACACCGCCGAAC  M.tuberculosis
79    TGCCCCTCCGGGG---TGGAAAAGTAGGGCACCGCCGAAC  M.bovis
81    TGCCCTCACGGGG---TGGAAAAGTAGGACACCGCCGAAC  M.phlei
3599  TGCCCATTCGGG----TGGAAAAGTAGGACACGGCCGAAC  M.leprae
5782  TGCCCTT-CGGGG---TGGAAAAGTAGGACACCGCCGAAC  M.smegmatis
```

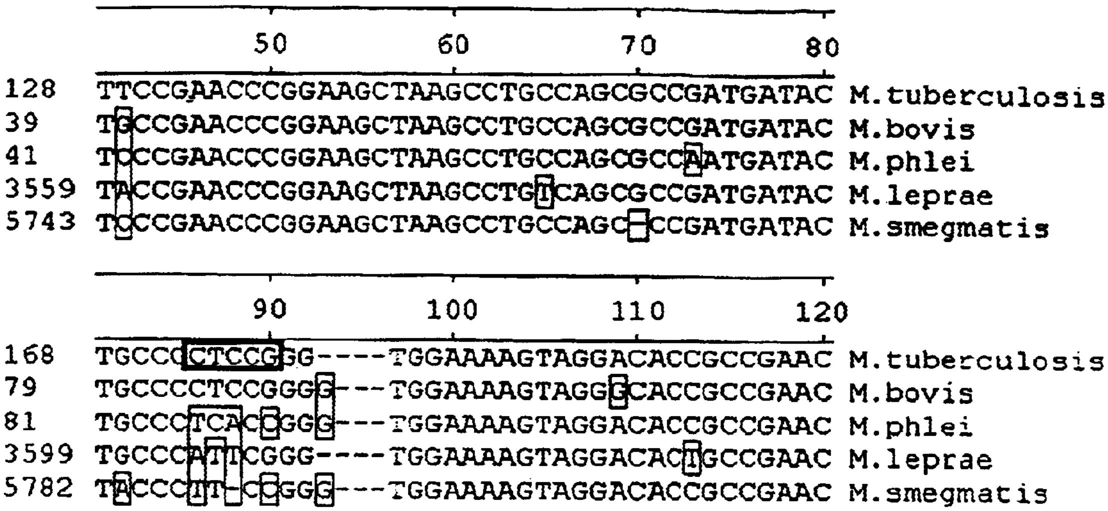

Figure 3

```
               90        100       110       120
382  GGGAGCTGTCAACCGAGCATTGATCCGAGGATTTCCGAAT M.avium
382  GGGAGCTGTCAACCGAGCATTGATCCGAGGATTTCCGAAT M.paratuberc.
1053 GGGAGCTGTCAACCGAGCGTGGATCCGAGGATTTCCGAAT M.tuberculosis
467  GGGAGCTGTCAACCGAGCGTGGATCCGAGGATTTCCGAAT M.phlei
392  GGGAGCTGTCAACCGAGCGTGGATCCGAGGATTTCCGAAT M.leprae
167  GGGAGCTGTCAACCGAGCGTGGATCCGAGGATTTCCGAAT M.gastri
110  GGGAGCTGTCAACCGAGCGTGGATCCGAGGATTTCCGAAT M.kansasii
2548 GGGAGCTGTCAACCGAGCGTTGATCCGAGGATGTCCGAAT M.smegmatis
```

- - - -

```
               170       180       190       200
462  GAATATATAGGGTGCG-GGAGGTAACGCGGGGAAGTGAAA M.avium
462  GAATATATAGGGTGCG-GGAGGTAACGCGGGGAAGTGAAA M.paratuberc.
1133 GAATATATAGGGTGCG-GGAGGGAACGCGGGGAAGTGAAA M.tuberculosis
547  GAATATATAGGCGTTG-GGGGGGAACGCGGGGAAGTGAAA M.phlei
472  GAATATATAGGGTTCG-GGAGGGAACGCGGGGAAGTGAAA M.leprae
247  GAATATATAGGGTGCG-GGAGGGAACGCGGGGAAGTGAAA M.gastri
190  GAATATATAGGGTGCG-GGAGGGAACGCGGGGAAGTGAAA M.kansasii
2628 GAATATATAGGCGTCT-GGGGGGAACGCGGCGAAGTGAAA M.smegmatis
```

- - - -

```
               250       260       270       280
541  -GTCAGTAGTGGCGAGCGAAC-CGGAACA-GGCTAAACCG M.avium
541  -GTCAGTAGTGGCGAGCGAAC-CGGAACA-GGCTAAACCG M.paratuberc.
1212 -GCAAGTAGTGGCGAGCGAACGCGGAACA-GGCTAAACCG M.tuberculosis
626  -GTGAGTAGTGGCGAGCGAA-AGGGAGGATGGCTAAACCG M.phlei
551  -GCAAGTAGTGGCGAGCGAACGTGGAATATGGCTAAACCG M.leprae
326  -GTCAGTAGTGGCGAGCGAACGCGGAACATGGCTAAACCG M.gastri
269  -GTAAGTAGTGGCGAGCGAACGCGGAACATGGCTAAACCG M.kansasii
2706 CGTGAGTAGTGGCGAGCGAACACGGAGGATGGCTAAAC-G M.smegmatis
```

Figure 4A

```
                 290       300       310       320
578   CATG-CATGGACAACCGGGTAGGGGTTGTGTGTGCGGGGT M.avium
578   CATG-CATGGACAACCGGGTAGGGGTTGTGTGTGCGGGGT M.paratuberc.
1250  CACG-CATGGGTAACCGGGTAGGGGTTGTGTGTGCGGGGT M.tuberculosis
664   CGTG-CATGTGATACCCGGTCGGGGTTGTGTGTGCGGTGT M.phlei
590   CACA-CATGTCTAACTAGGTAGGGGTTGTGTGTGCGGTGT M.leprae
365   CACG-CATGGGTGACCGGGTAGGGGTTGTGTGTGCGGGGT M.gastri
308   CACG-CATGGGTAACCGGGTAGGGGTTGTGTGTGCGGGGT M.kansasii
2745  TATGACATGTGATACCGGGTAGGGGTTGTGTGTGCGGGGT M.smegmatis

                 330       340       350       360
617   TGTGGGATTGATATGTCTCAGCTCTACCTGGCTGAGG-GG M.avium
617   TGTGGGATTGATATGTCTCAGCTCTACCTGGCTGAGG-GG M.paratuberc.
1289  TGTGGGAG-GATATGTCTCAGCGCTACCCGGCTGAGA-GG M.tuberculosis
703   TGTGGGGCCTGTGTGTC-CATCGTCCGCCGGCGATGGCAG M.phlei
629   TGTGGGATTGGTATGTCTCAACTCTACCTGGTTGAGG-GG M.leprae
404   TGTGGGATCGATACGTCTCAGCTCTACCCGGCTGAGG-GG M.gastri
347   TGTGGGATCGATACGTCTCAGCTCTACCCGGCTGAGG-GG M.kansasii
2785  TGTGGGACCTATCTTTC-CGCCTCTACCTGGCTG-GAGGG M.smegmatis

                 370       380       390       400
656   TAGTCAGAAAGTGTCGTGGTTAGCGGAAGTGGCCTGGGAC M.avium
656   TAGTCAGAAAGTGTCGTGGTTAGCGGAAGTGGCCTGGGAC M.paratuberc.
1327  CAGTCAGAAAGTGTCGTGGTTAGCGGAAGTGGCCTGGGAT M.tuberculosis
742   TAGTGATAAAGCAGTGTGGTTAGGTGAAGTGGCCTGGGAT M.phlei
668   TAGTCAGAAAGTGCCGTGGTTAGCGGAAATGGCCTGGGAT M.leprae
443   CAGTCAGAAAGTGTCGTGGTTAACGGAAGTGGCCTGGGAT M.gastri
386   CAGTCAGAAAGTGTCGTGGTTAACGGAAGTGGCCTGGGAT M.kansasii
2823  CAGTGAGAAAATGTTGTGGTTAGCGGAAATGGCTTGGGAT M.smegmatis
```

Figure 4B

```
                410       420       430       440
696  GGCCCGCCGTAGACGGTGAGAGCCCGGTACGCGAAA-ACC M.avium
696  GGCCCGCCGTAGACGGTGAGAGCCCGGTACGCGAAA-ACC M.paratuberc.
1367 GGTCTGCCGTAGACGGTGAGAGCCCGGTACGCGAAA-ACC M.tuberculosis
782  GGTCTGCCGTAGTGGGTGAGAGCCCGTAAC-CGAAA-ACA M.phlei
708  GGCCTGCCGTAGACGGTGAGAGCCCAGTACGCGAAA-GCC M.leprae
483  GGTCTGCCGTAGACGGTGAGAGCCCGGTACGTGAAA-ACC M.gastri
426  GGTCTGCCGTAGACGGTGAGAGCCCGGTACGTGAAA-ACC M.kansasii
2863 GGCCTCCCGTAGACGGTGAGAGCCCGGTACGTGAAA-ACC M.smegmatis

                450       460       470       480
735  CGGCACCTGCCTTATATCAACACCCGAGTAGCAGCGGGCC M.avium
735  CGGCACCTGCCTTATATCAACACCCGAGTAGCAGCGGGCC M.paratuberc.
1406 CGGCACCTGCCTAGTATCAATTCCCGAGTAGCAGCGGGCC M.tuberculosis
820  TGCTGCC-GCTGTCACAGG--TCCCGAGTAGCAGCGGGCC M.phlei
747  TGGCACCTGCCTTGTATCAATTCCCGAGTAGCAGCGGGCC M.leprae
522  CGGCACCTGCCTTGTATCAATTCCCGAGTAGCAGCGGGCC M.gastri
465  CGGCACCTGCCTTGTATCAATTCCCGAGTAGCAGCGGGCC M.kansasii
2902 CGACGTCTGTCTTGATGGTGTTCCCGAGTAGCAGCGGGCC M.smegmatis

- - - -

                570       580       590       600
855  GAGGGAATGGTGAAAAGTACCCCGGGAGGG-AGTGAAATA M.avium
855  GAGGGAATGGTGAAAAGTACCCCGGGAGGG-AGTGAAATA M.paratuberc.
1526 GAGGGAATGGTGAAAAGTACCCCGGGAGGGGAGTGAAAGA M.tuberculosis
937  GAGGGAATCGTGAAAAGTACCCCGGGAGGG-AGTGAAAGA M.phlei
867  GAGGGAATGGTGAAAAGTACCCCGGGAGGGGAGTGAAATA M.leprae
642  GAGGGAATGGTGAAAAGTACCCCGGGAGGGGAGTGAAAGA M.gastri
585  GAGGGAATGGTGAAAAGTACCCCGGGAGGGGAGTGAAAGA M.kansasii
3022 GAGGGAATGGTGAAAAGTACCCCGGGAGGGGAGTGAAAGA M.smegmatis
```

Figure 4C

```
                610       620       630       640
894  GTACCTGAAACCGTGTGCCTACAATCCGTCAGAGCCTCCT M.avium
894  GTACCTGAAACCGTGTGCCTACAATCCGTCAGAGCCTCCT M.paratuberc.
1566 GTACCTGAAACCGTGTGCCTACAATCCGTCAGAGCCTCCT M.tuberculosis
976  GTACCTGAAACCGTGTGCCTACAATCCGTCAAAGCCCTCT M.phlei
907  GTACCTGAAACCGTGTGCCTACAATCCGTCAGAGCCTCTT M.leprae
682  GTACCTGAAACCGTGTGCCTACAATCCGTCAGAGCCCCTT M.gastri
625  GTACCTGAAACCGTGTGCCTACAATCCGTCAGAGCCCTTT M.kansasii
3062 GTACCTGAAACCGTGCGCTTACAATCCGTCAGAGCCCTCG M.smegmatis
```

```
                650       660       670       680
934  C---------------GTGGGGTGATGGCGTGCCTTTTGA M.avium
934  C---------------GTGGGGTGATGGCGTGCCTTTTGA M.paratuberc.
1606 TTTCCTCTCCGGAGGAGCGTGGTGATGGCGTGCCTTTTGA M.tuberculosis
1016 CTT----------GTAGTGGGGTGATGGCGTGCCTTTTGA M.phlei
947  T---------------GTGGGGTGATGGCGTGCTTTTTGA M.leprae
722  T---------------GTGGGGTGATGGCGTGCCTTTTGA M.gastri
665  C---------------GTGGGGTGATGGCGTGCCTTTTGA M.kansasii
3102 ACGTGT----------GTGGGGTGATGGCGTGCCTTTTGA M.smegmatis
```

```
               690       700       710       720
959  AGAATGAGCCTGCGAGTCAGGGACACGTCGCGAGGTTAAC M.avium
23   AGAATGAGCCTGCGAGTCAGGGACACGTCGCGAGGTTAAC M.intracellulare
959  AGAATGAGCCTGCGAGTCAGGGACACGTCGCGAGGTTAAC M.paratuberc.
1646 AGAATGAGCCTGCGAGTCAGGGACATGTCGCAAGGTTAAC M.tuberculosis
4    AGAATGAGCCTGCGAGTCAGGGACATGTCGCAAGGTTAAC M.bovis
1046 AGAATGAGCCTGCGAGTCAGGGACATGTCGCGAGGTTAAC M.phlei
972  AGAATGAGCCTGCGAGTCAGGGACATGTCGCGAGGTTAAC M.leprae
747  AGAATGAGCCTGCGAGTCAGGGACATGTCGCGAGGTTAAC M.gastri
690  AGAATGAGCCTGCGAGTCAGGGACATGTCGCGAGGTTAAC M.kansasii
3132 AGAATGAGCCTGCGAGTCAGGGACATGTCGCGAGGTTAAC M.smegmatis
```

Figure 4D

```
           770       780       790       800
1039  CGCATCCCCTTTGGG-----------GTGTAGTGGCGTGT  M.avium
103   CGCATCCCCTTTGGG-----------GTGTAGTGGCGTGT  M.intracellulare
1039  CGCATCCCTTTTGGG-----------GTGTAGTGGCGTGT  M.paratuberc.
1726  CGACCCACACGCGCATACGCGCGTGTGAATAGTGGCGTGT  M.tuberculosis
84    CGACCCACACGCGCATACGCGCGTGTGAATAGTGGCGTGT  M.bovis
1126  CGTATCCAACCTGTT----GGGGTTGGTGTAGTGGTGTGT  M.phlei
1052  CGTATCACGTGTGAGCGT--------GTGTAGTGGCGTGT  M.leprae
827   CGTATCACGCGTAAGCGT--------GTGTAGTGGCGTGT  M.gastri
770   CGTATCGCGCGCGAGCGT--------GTGTAGTGGCGTGT  M.kansasii
3212  CGTATCCACACAAGAGTGTGTG----GTGTAGTGGTGTGT  M.smegmatis
```

----

```
          1050      1060      1070      1080
1307  CAGCCAAACTCCGAATGCCG-TGGTG-TAAAAGCGTGGCA  M.avium
1307  CAGCCAAACTCCGAATGCCG-TGGTG-TAAAAGCGTGGCA  M.paratuberc.
2005  CAGCCAAACTCCGAATGCCG-TGGTG-TA-AAGCGTGGCA  M.tuberculosis
1401  CAGCCAAACTCCGAATGCCGATAAG--TGAAAGTGTGGCA  M.phlei
1323  CAGCCAAACTCCGAATGCCG-TGGTT-TAAAAGCGTGGCA  M.leprae
1098  CAGCCAAACTCCGAATGCCG-TGGTG-TATA-GCGTGGCA  M.gastri
1041  CAGCCAAACTCCGAATGCCG-TGGTG-TATA-GCGTGGCA  M.kansasii
3486  CAGCCAAACTCCGAATGCCGGTAAGGCCAAGAGTGCGGAA  M.smegmatis
```

----

```
          1170      1180      1190      1200
1425  AGTGGAAAAGGATGTGTAGTCGCAGA-GACAACCAGGAGG  M.avium
1425  AGTGGAAAAGGATGTGTAGTCGCAGA-GACAACCAGGAGG  M.paratuberc.
2122  AGTGGGAAAGGATGTGCAGTCGCAAA-GACAACCAGGAGG  M.tuberculosis
1519  AGTGGAAAAGGATGTGCAGTCGC-GAAGACAACCAGGAGG  M.phlei
1441  AGTGGAAAAGGATGTGCAGTCGCAAA-GACAACCAGGAGG  M.leprae
1215  AGTGGGAAAGGATGTGCAGTCGCAGA-GACAACCAGGAGG  M.gastri
1158  AGTGGGAAAGGATGTGCAGTCGCAGA-GACAACCAGGAGG  M.kansasii
3606  AGTGGAAAAGGATGTGAAGTCGCAGAAGAAAACCAGGAGG  M.smegmatis
```

Figure 4E

```
                1250      1260      1270      1280
1504 CTCACTGGTCAAGTGATTATGCGCCGATAATGTAGCGGGG M.avium
1504 CTCACTGGTCAAGTGATTATGCGCCGATAATGTAGCGGGG M.paratuberc.
2201 CTCACTGGTCAAGTGATTGTGCGCCGATAATGTAGCGGGG M.tuberculosis
1598 CTCACTGGTCAAGTGATTGTGCGCTGATAATGTAGCGGGG M.phlei
1520 CTCACTGGTCAAGTGATTGTGCGCCGATAATGTAGCGGGG M.leprae
1294 CTCACTGGTCAAGTGATTGTGCGCCGATAATGTAGCGGGG M.gastri
1237 CTCACTGGTCAAGTGATTGTGCGCCGATAATGTAGCGGGG M.kansasii
3686 TTCACTGGTCAAGTGATTGTGCGCCGATATTGTGGCGGGG M.smegmatis

                1290      1300      1310      1320
1544 CTCAAGCACACCGCCGAAGCCGCGGCACATTCATCTT-TA M.avium
1544 CTCAAGCACACCGCCGAAGCCGCGGCACATTCATCTT-TA M.paratuberc.
2241 CTCAAGCACACCGCCGAAGCCGCGGCACATCCACCTTGT- M.tuberculosis
1638 CTCAAGCACACCGCCGAAGCCGCGGCA--ATCAGCCTTTG M.phlei
1560 CTCAAGCACACCGCCGAAGCCGCGGCACATTCACCTTCTA M.leprae
1334 CTCAAGCACACCGCCGAAGCCGCGACA-----ACCGC--A M.gastri
1277 CTCAAGCACACCGCCGAAGCCGCGACA-----ACCGC--A M.kansasii
3726 TTCAAGCACACCGCCGAAGCCGCGGAA--GCCAACGTTTG M.smegmatis

                1330      1340      1350      1360
1583 CGGTGGATGTGGGTAGGGGAGCGTCCCCCATTCAGCGAAG M.avium
1583 CGGTGGATGTGGGTAGGGGAGCGTCCCCCATTCAGCGAAG M.paratuberc.
2280 -GGTGGGTGTGGGTAGGGGAGCGTCCCTCATTCAGCGAAG M.tuberculosis
1676 TGGCTGGTGTGGGTAGGGGAGCGTCCTGCATCCGGTGAAG M.phlei
1600 GGGTGGATGTGGGTAGGGGAGCGTTCCTCATTCAGCGAAG M.leprae
1367 AGGT-----TGGGTAGGGGAGCGTCCCTCATTCAGCGAAG M.gastri
1310 AGGT-----TGGGTAGGGGAGCGTCCCTCATTCAGCGAAG M.kansasii
3764 TT-------TGGGTAGGGGAGCGTCCTG-ATCCGGTGAAG M.smegmatis
```

Figure 4F

```
          1370      1380      1390      1400
1623 CT-CCGGGTGACCGGTGGTGGAGGGTGGGGGAGTGAGAAT M.avium
1623 CT-CCGGGTGATCGGTGGTGGAGGGTGGGGGAGTGAGAAT M.paratuberc.
2319 CCACCGGGTGACCGGTGGTGGAGGGTGGGGGAGTGAGAAT M.tuberculosis
1716 CCGCCGAGTGATCGGTGGTGGAGGGTGTGGGAGTGAGAAT M.phlei
1640 CCTCCGGGTAACCGGTGGTGGAGGGTGGGGAAGTGAGAAT M.leprae
1402 CCGCCGGGTGACCGGTGGTGGAGGATGGGGGAGTGAGAAT M.gastri
1345 CTGCCGGGTGACCGGTGGTGGAGGATGGGGGAGTGAGAAT M.kansasii
3796 CCGCCGAGTATCGAGTGGTGGAGGGTGTGGGAGTGAGAAT M.smegmatis
```

- - - -

```
          1530      1540      1550      1560
1781 CGATGGACAACGGGTTGATATTCCCGTACCCGTGTATGGG M.avium
1781 CGATGGACAACGGGTTGATATTCCCGTACCCGTGTATGGG M.paratuberc.
2479 CGATGGACAACGGGTTGATATTCCCGTACCCGTGTGTGGG M.tuberculosis
1875 CGATGGACAACGGGTTGATATTCCCGTACCCGTGTATGAG M.phlei
1800 CGATGGACAACGGGTTGATATTCCCGTACCCGTGTGTGTG M.leprae
1562 CGATGGACAACGGGTTGATATTCCCGTACCCGTGTGTGGG M.gastri
1505 CGATGGACAACGGGTTGATATTCCCGTACCCGTGTGTGGG M.kansasii
3956 CGATGGACAACGGGTTGATATTCCCGTACCCGTGTATGTG M.smegmatis
```

```
          1570      1580      1590      1600
1821 CGTCCCTGATGAATCA-GCGGTACTAACCACCCAAAACCG M.avium
1821 CGTCCCTGATGAATCA-GCGGTACTAACCACCCAAAACCG M.paratuberc.
2519 CGCCCGTGACGAATCA-GCGGTACTAACCACCCAAAACCG M.tuberculosis
1915 CGTCCCTGATGAATCTCATTCTGCTAACCACCCAAAACCT M.phlei
1840 CGCCCGTGATGAATCA-GCGGTACTGACCACCCAAAACCG M.leprae
1602 CGCCCGTGATGAATCA-GCGGTACTAACCACCCAAAACCG M.gastri
1545 CGCCCGTGATGAATCA-GCGGTACTAACCACCCAAAACCG M.kansasii
3996 CGTCCATGATGAATCA-GCGGTACTAACCATCCAAAACCA M.smegmatis
```

Figure 4G

```
                 1610      1620      1630      1640
1860 GAT-CGACCAT-TCCCCTTCGGGGGC-GTGGCGATT-CGG M.avium
1860 GAT-CGACCAT-TCCCCTTCGGGGGC-GTGGCGATT-CGG M.paratuberc.
2558 GAT-CGATCAC-TCCCCTTCGGGGG-TGTGGAGTTC-TGG M.tuberculosis
1955 GGC-CGATC--ATCC--TTCGGGG--GTGACGGTTG-GG M.phlei
1879 GAT-CGACCATATCCCCTTCGGGGGCTATGGAGGTT-CGG M.leprae
1641 GAT-CGATCAC-TCCCCTTCGGGGGA-GTGGAGGTC-TGG M.gastri
1584 GAT-CGATCAC-TCCCCTTCGGGGGC-GTGGAGGTC-TGG M.kansasii
4035 ACCGTGACCGCACCT--TTCGGGG--TGTGGCGTTGGTGG M.smegmatis

                1650      1660      1670      1680
1896 GGCTGCGTGGGACCTTCGCTGGTAGTAGTCAAGCAATGGG M.avium
1896 GGCTGCGTGGGACCTTCGCTGGTAGTAGTCAAGCAATGGG M.paratuberc.
2594 GGCTGCGTGGGAACTTCGCTGGTAGTAGTCAAGCGAAGGG M.tuberculosis
1986 GGCTGCGTGGGACCCG-GTGGGTAGTAGTCAAGCGATGGG M.phlei
1917 GGCTGCGTGGGAACTTCGTTGGTAGTAGTCAAGCGATGGG M.leprae
1677 GGCTGCGTGGAGCCTTCGCTGGTAGTAGTCAAGCGATGGG M.gastri
1620 GGCTGCGTGGAGCCTTCGCTGGTAGTAGTCAAGCGATGGG M.kansasii
4071 GGCTGCATGGGACCTTCGTTGGTAGTAGTCAAGCGATGGG M.smegmatis

                1690      1700      1710      1720
1936 -GTGACGCAGGAAGGCAGCCGTACCAGTCAGTGGTAATA- M.avium
1936 -GTGACGCAGGAAGGCAGCCGTACCAGTCAGTGGTAATA- M.paratuberc.
2634 -GTGACGCAGGAAGGTAGCCGTACCAGTCAGTGGTAACA- M.tuberculosis
2025 -GTGACGCAGGAAGGTAGCCGTACCAGTCAGTGGTAATA- M.phlei
1957 -GTGACGCAGGAAGGTAGCCGTACCAGTCAGTGGTAATA- M.leprae
1717 -GTGACGCAGGAAGGCAGCCGTACCAGTCAGTGGTAATA- M.gastri
1660 -GTGACGCAGGAAGGCAGCCGTACCAGTCAGTGGTAATA- M.kansasii
4111 -GTGACGCAGGAAGGTAGCCGTACCGGTCAGTGGTAATA- M.smegmatis

                1730      1740      1750      1760
1974 -CTGGGGCAAGCCCGTAG--AGAGCGATAGGCAAATCCGT M.avium
1974 -CTGGGGCAAGCCCGTAG--AGAGCGATAGGCAAATCCGT M.paratuberc.
2672 -CTGGGGCAAGCCGGTAGGGAGAGCGATAGGCAAATCCGT M.tuberculosis
2063 -CCGGGGTAAACCTGTAGGGCGAGTGATAGGCAAATCCGT M.phlei
1995 -CTGGAGCAAGCCCGTAGGGAGAGCGATAGGCAAATCCGT M.leprae
1755 -CTGGGGCAAGCCAGTAGGGAGAGCGATAGGCAAATCCGT M.gastri
1698 -CTGGGGCAAGCCAGTAGGGAGAGCGATAGGCAAATCCGT M.kansasii
4149 -CCGGCGTAAGCCTGTAGGGAGTCAGATAGGTAAATCCGT M.smegmatis
```

Figure 4H

```
          1810      1820      1830      1840
2051 CG-AATTCGGTGATCCTCTGCTGCCAAGAAAAGCCTCTA- M.avium
2051 CG-AATTCGGTGATCCTCTGCTGCCAAGAAAAGCCTCTA- M.paratuberc.
2751 CG-AATTCGGTGATCCTCTGCTGCCAAGAAAAGCCTCTA- M.tuberculosis
2141 CG-AATTCGGTGATCCTATGCTGTCGAGAAAAGCCTCTA- M.phlei
2074 CG-AATTCGGTAAGCCTCTGCTGCCAAGAAAAGCCTCTA- M.leprae
1834 CG-AATTCGGTGATCCTCTGCTGCCAAGAAAAGCCTCTA- M.gastri
1777 CG-AATTCGGTGATCCTCTGCTGCCAAGAAAAGCCTCTA- M.kansasii
4228 CG-AATTCGGTGATCCTATGCTGCCGAGAAAAGCCTCTA- M.smegmatis

          1850      1860      1870      1880
2089 GCGAGCACATACACGGCCCGTACCCCAAACCAACACAGGT M.avium
2089 GCGAGCACATACACTGCCCGTACCCCAAACCAACACAGGT M.paratuberc.
2789 GCGAGCACACACACGGCCCGTACCCCAAACCGACACAGGT M.tuberculosis
2179 GCAAGCGCATACACGGCCCGTACCCCAAACCAACACAGGT M.phlei
2112 GCGAGCATACATGCGGCCCGTACCCCAAACCGACACAGGT M.leprae
1872 GCGAGCACACACACGGCCCGTACCCCAAACCGACACAGG  M.gastri
1815 GCGAGCACACACACGGCCCGTACCCCAAACCGACACAGGT M.kansasii
4266 GCGAGGACATACACGGCCCGTACCCCAAACCAACACAGGT M.smegmatis

- - - -

          1970      1980      1990      2000
2208 AGGGGGCCCGGAATACCGTGAACACCCTTGCGGTGGGAGC M.avium
2208 AGGGGGCCCGGAATACCGTGAACACCCTTGCGGTGGGAGC M.paratuberc.
2908 AGGGGGACCGGAATATCGTGAACACCCTTGCGGTGGGAGC M.tuberculosis
2298 AGGGGGACCCACGTACCGTGAGGGCTCTTGCGGCGGCAGC M.phlei
2231 AGGGGGGCCGGAATATCGTGAACACCCTTGCGGTGGGAGC M.leprae
1910                                          M.gastri
1934 AGGGGGACCGGAATACCGTGAACACCCTTGCGGTGGGAGC M.kansasii
4385 AGGGGGACCCACATGGCGTGTAAGCCTTTACGGCCCAAGC M.smegmatis

          2010      2020      2030      2040
2248 GGGATTCGGCCGCAGAAACCAGTGGGTAGCGACT-GTTTA M.avium
2248 GGGATTCGGCCGCAGAAACCAGTGGGTAGCGACT-GTTTA M.paratuberc.
2948 GGGATCCGGTCGCAGAAACCAGTGAGGAGCGACT-GTTTA M.tuberculosis
2338 GGGGGTGGGTGGCACAAACCAGTGAGGAGCGACT-GTTTA M.phlei
2271 GGGATCCGGTCGCAGAGACCAGTGAGAAGCGACT-GTTTA M.leprae
1910                                          M.gastri
1974 GGGATTCGGTCGCAGAAACCAGTGAGAAGCGACTTGTTTA M.kansasii
4425 GTGAGTGGGTGGCACAAACCAGTGAGAAGCGACT-GTTTA M.smegmatis
```

Figure 4I

```
                     2130      2140      2150      2160
2367 CCGTTAACCCGT--AAGGGTGAAGCGGAGAATTTAAGCCC M.avium
2367 CCGTTAACCCGT--AAGGGTGAAGCGGAGAATTTAAGCCC M.paratuberc.
3067 CCGTTAACCCGC--AAGGGTGAAGCGGAGAATTTAAGCCC M.tuberculosis
2457 CCGTTAACCCTTTCGGGGGTGAAGCGGAGAATTTAAGCCC M.phlei
2390 CTGTTAACCCGA--AAGGGTGAAGCGGAGAATTTAAGCCC M.leprae
1910                                          M.gastri
2094 CCGTTAACCCGC--AAGGGTGAAGCGGAGAATTTAAGCCC M.kansasii
4544 CCGTTAACCCCCTTGGGGGTGAAGCGGAGAATTTAAGCCC M.smegmatis
```

- - - -

```
                     2250      2260      2270      2280
2485 GTAACGACTTCCCAACTGTCTCAACCATAGACTCGGCGAA M.avium
2485 GTAACGACTTCCCAACTGTCTCAACCATAGACTCGGCGAA M.paratuberc.
3185 GTAACGACTTCTCAACTGTCTCAACCATAGACTCGGCGAA M.tuberculosis
2577 GTAACGACTTCTCAACTGTCTCAACCATAGACTCGGCGAA M.phlei
2508 GTAACGACTTCTCAACTGTCTCAACCATAGACTCGGCGAA M.leprae
1910                                          M.gastri
2212 GTAACGACTTCTCAACTGTCTCAACCATAGACTCGGCGAA M.kansasii
4663 GTAACGACTTCTCAACTGTCTCAAC-ATAGACTCGGCGAA M.smegmatis
```

- - - -

```
                     2370      2380      2390      2400
2605 GTTCGGTACGGTTTGTGTAGGATAGGTGGGAGACTTTGAA M.avium
2605 GTTCGGTACGGTTTGTGTAGGATAGGTGGGAGACTTTGAA M.paratuberc.
3305 GTTCGGTACGGTTTGTGTAGGATAGGTGGGAGACTGTGAA M.tuberculosis
2697 GCTCGATACGGTTTGTGTAGGATAGGTGGGAGACTGTGAA M.phlei
2628 GTTCGGTGCGGTTTGTGTAGGATAGGTGGGAGACTGTGAA M.leprae
1910                                          M.gastri
2332 GTTCGGTACGGTTTGTGTAGGATAGGTGGGAGACTGTGAA M.kansasii
4782 GCTCGATACGGTTTGTGTAGGATAGGTGGGAGACTGTGAA M.smegmatis
```

Figure 4J

```
                2410      2420      2430      2440
2645 GCACAGACGCCAGTTTGTGTGGAGTCGTTGTTGAAATACC M.avium
393  ATACAGACGCCAGTTTGTATGGAGTCGTTGTTGAAATACC M.intracellulare
2645 GCACAGACGCCAGTTTGTGTGGAGTCGTTGTTGAAATACC M.paratuberc.
3345 ACCTCGACGCCAGTTGGGGCGGAGTCGTTGTTGAAATACC M.tuberculosis
284  ACCTCGACGCCAGTTGGGGCGGAGTCGTTGTTGAAATACC M.bovis
2737 GCTCGGACGCCAGTTCGGGTGGAGTCGTTGTTGAAATACC M.phlei
2668 ACTTCGACGCTAGTTGGGGTGGAGTCGTTGTTGAAATACC M.leprae
1910                                          M.gastri
2372 ACCTCAACGCCAGTTGGGGTGGAGTCGTTGTTGAAATACC M.kansasii
4822 GCTCACACGCCAGTGTGGGTGGAGTCGTTGTTGAAATACC M.smegmatis

                2450      2460      2470      2480
2685 ACTCTGATCGTATTGGACACCTAACGTCGAACCCT-TATC M.avium
433  ACTCTGATCGTATTGGACACCTAACGTCGAACCCT-TATC M.intracellulare
2685 ACTCTGATCGTATTGGACACCTAACGTCGAACCCT-TATC M.paratuberc.
3385 ACTCTGATCGTATTGGGCATCTAACCTCGAACCCTGAATC M.tuberculosis
324  ACTCTGATCGTATTGGGCATCTAACCTCGAACCCTGAATC M.bovis
2777 ACTCTGATCGTATTGGGCCTCTAACCTCGGACCGTGGATC M.phlei
2708 ACTCTGATTGTATTGAACATCTAACCTCGAACCGTATATC M.leprae
1910                                          M.gastri
2412 ACTCTGATCGTATTGGACACCTAACGTCGAACCCTGAATC M.kansasii
4862 ACTCTGATCGTATTGGGCCTCTAACCTCGGACCGTATATC M.smegmatis

- - - -

                2690      2700      2710      2720
2924 GGTGTCACTCAACGGATAAAAGGTACCCCGGGGATAACGG M.avium
2924 GGTGTCACTCAACGGATAAAAGGTACCCCGGGGATAACAG M.paratuberc.
3625 GGTGTCGCTCAACGGATAAAAGGTACCCCGGGGATAACAG M.tuberculosis
3017 GGTGTCGCTCAACGGATAAAAGGTACCCCGGGGATAACAG M.phlei
2948 GGTGTCGCTCAACGGATAAAAGGTACCCCGGGGATAACAG M.leprae
1910                                          M.gastri
2652 GGTGTCGCTCAACGGATAAAAGGTACCCCGGGGATAACAG M.kansasii
5102 GGTGTCGCTCAACGGATAAAAGGTACCCCGGGGATAACAG M.smegmatis

                2730      2740      2750      2760
2964 GCTGATCTTCCCCAAGAGTCCATATCGACGGGATGGTTTG M.avium
2964 GCTGATCTTCCCCAAGAGTCCATATCGACGGGATGGTTTG M.paratuberc.
3665 GCTGATCTTCCCCAAGAGTCCATATCGACGGGATGGTTTG M.tuberculosis
3057 GCTGATCTTCCCCAAGAGTCCATATCGACGGGATGGTTTG M.phlei
2988 GCTGATCTTCCCCAAGAGTCCATATCGACGGGATGGTTTG M.leprae
1910                                          M.gastri
2692 GCTGATCTTCCCCAAGAGTCCATATCGACGGGATGGTTTG M.kansasii
5142 GCTGATCTTCCCCAAGAGTCCATATCGACGGGATGGTTTG M.smegmatis
```

Figure 4K

```
          2770      2780      2790      2800
3004 GCACCTCGATGTCGGCTCGTCGCATCCTGGGGCTGGAGCA M.avium
3004 GCACCTCGATGTCGGCTCGTCGCATCCTGGGGCTGGAGCA M.paratuberc.
3705 GCACCTCGATGTCGGCTCGTCGCATCCTGGGGCTGGAGCA M.tuberculosis
3097 GCACCTCGATGTCGGCTCGTCGCATCCTGGGGCTGGAGCA M.phlei
3028 GCACCTCGATGTCGGCTCGTCGCATCCTGGGGCTGAAGCA M.leprae
1910                                          M.gastri
2732 GCACCTCGATGTCGGCTCGTCGCATCCTGGGGCTGGAGCA M.kansasii
5182 GCACCTCGATGTCGGCTCGTCGCATCCTGGGGCTGGAGCA M.smegmatis

          2810      2820      2830      2840
3044 GGTCCCAAAGGTTGGGCTGTTCGCCC-ATTAAAGCGGCAC M.avium
3044 GGTCCCAAGGGTTGGGCTGTTCGCCC-ATTAAAGCGGCAC M.paratuberc.
3745 GGTCCCAAGGGTTGGGCTGTTCGCCC-ATTAAAGCGGCAC M.tuberculosis
3137 GGTCCCAAGGGTTGGGCTGTTCGCCC-ATTAAAGCGGCAC M.phlei
3068 GGTCCCAAGGGTTGGGCTGTTCGCCC-ATTAAAGCGGCAC M.leprae
1910                                          M.gastri
2772 GGTCCCAAGGGTTGGGCTGTTCGCCC-ATTAAAGCGGCAC M.kansasii
5222 GGTCCCAAGGGTTGGGCTGTTCGCCCCATTAAAGCGGCAC M.smegmatis

- - - -

          3050      3060      3070      3080
3283 CAAGATCAGGTTT-CTCACCCTTTTAGAGGGATAAGGCCC M.avium
638  CAAGATCAGGTTT-CTCACCCTTTTAGAGGGATAAGGCCC M.intracellulare
3283 CAAGATCAGGTTT-CTCACCCTTTTAGAGGGATAAGGCCC M.paratuberc.
3984 CAAGATCAGGTTT-CTCACCCACTTGGTGGGATAAGGCCC M.tuberculosis
570  CAAGATCAGGTTT-CTCACCCACTTGGTGGGATAAGGCCC M.bovis
3376 CAAGACCAGGCTT-CTCACCCTCTAGGAGGGATAAGGCCC M.phlei
3307 CAA                                      M.leprae
1910                                          M.gastri
3011 CAAGATCAGGCTT-CTCACCCACTTGGTGGGATAAGGCCC M.kansasii
5462 CAAGACCAGGCTT-CTCACCCTCTAGGAGGGATAAGGCCC M.smegmatis

          3090      3100      3110      3120
3322 CCCGC-AGACCACGGGATTGATAGGCCAGACCTGGAAGCT M.avium
677  CCCGC-AGACCACGGGTTCGATAGGCCAGACCTGGAAGCT M.intracellulare
3322 CCCGC-AGATCACGGGATTGATAGGCCAGACCTGGAAGCT M.paratuberc.
4023 CCCGC-AGAACACGGGTTCAATAGGTCAGACCTGGAAGCT M.tuberculosis
609  CCCGC-AGAACACGGGTTCAATAGGTCAGACCTGGAAGCT M.bovis
3415 CCCGC-AGACCACGGGATCGATAGACCAGACCTGCACGCA M.phlei
3309                                          M.leprae
1910                                          M.gastri
3050 CCCGC-AGAACACGGGTTCGATAGGCCAGACCTGGAAGCT M.kansasii
5501 CCCGC-AGACCACGGGATTGATAGACCAGACCTGGAAGCC M.smegmatis
```

Figure 4L

```
                     130        140        150        160
107  GAGTAACACGTGGGCAATCTGCCCTGCACTTC-GGGATAA M.avium
59   GAGTAACACGTGGGCAATCTGCCCTGCACTTC-GGGATAA M.intracellulare
107  GAGTAACACGTGGGCAATCTACCCTGCACTTC-GGGATAA M.paratuberc.
70   GAGTAACACGTGGGCAATCTGCCCTGCACTTC-GGGATAA M.scrofulaceum
70   GAGTAACACGTGGGTGATCTGCCCTGCACTTC-GGGATAA M.tuberculosis
209  GAGTAACACGTGGGTGATCTGCCCTGCACTTC-GGGATAA M.bovis
120  GAGTAACACGTGGGTAATCTGCCCTGCACTTCAGGGATAA M.leprae
69   GAGTAACACGTGGGCAATCTGCCCTGCACACC-GGGATAA M.kansasii
70   GAGTAACACGTGGGCAATCTGCCCTGCACACC-GGGATAA M.gastri
104  GAGTAACACGTGGGTAATCTGCCCTGCACATC-GGGATAA M.gordonae
64   GAGTAACACGTGGGCGATCTGCCCTGCACTTC-GGGATAA M.marinum

                                ----

                     450        460        470        480
424  AAACCTCTTTCACCATCGACGAAGGTCCGGGTTTTCTCGG M.avium
376  AAACCTCTTTCACCATCGACGAAGGTCCGGGTTTTCTCGG M.intracellulare
424  AAACCTCTTTCACCATCGACGAAGGTCCGGGTTTTCTAGG M.paratuberc.
387  AAACCTCTTTCACCATCGACGAAGGCTCA---CTTTGTGG M.scrofulaceum
389  AAACCTCTTTCACCATCGACGAAGGTCCGGGTTCTCTCGG M.tuberculosis
528  AAACCTCTTTCACCATCGACGAAGGTCCGGGTTCTCTCGG M.bovis
439  AAACCTCTTTCACCATCGACGAAGGTCTGGGAATTCTCGG M.leprae
386  AAACCTCTTTCACCATCGACGAAGGTCCGGGTTCTCTCGG M.kansasii
387  AAACCTCTTTCACCATCGACGAAGGTCCGGGTTCTCTCGG M.gastri
420  AAACCTCTTTCACCATCGACGAAGGTCCGGGTTTTCTCGG M.gordonae
381  AAACCTCTTTCACCATCGACGAAGGTTCGGGTTTTCTCGG M.marinum

                     490        500        510        520
429  ATTGACGGTAGGTGGAGAAGAAGCACCGGCCAACTACGTG M.tuberculosis
568  ATTGACGGTAGGTGGAGAAGAAGCACCGGCCAACTACGTG M.bovis
464  ATTGACGGTAGGTGGAGAAGAAGCACCGGCCAACTACGTG M.avium
416  ATTGACGGTAGGTGGAGAAGAAGCACCGGCCAACTACGTG M.intracellulare
464  ATTGACGGTAGGTGGAGAAGAAGCAC------ACTACGTG M.paratuberc.
424  GTTGACGGTAGGTGGAGAAGAAGCACCGGCCAACTACGTG M.scrofulaceum
479  ATTGACGGTAGGTGGAGAAGAAGCACCGGCCAACTACGTG M.leprae
426  ATTGACGGTAGGTGGAGAAGAAGCACCGGCCAACTACGTG M.kansasii
427  ATTGACGGTAGGTGGAGAAGAAGCACCGGCCAACTACGTG M.gastri
460  GCTGACGGTAGGTGGAGAAGAAGCACCGGCCAACTACGTG M.gordonae
421  ATTGACGGTAGGTGGAGAAGAAGCACCGGCCAACTACGTG M.marinum
```

Figure 5A

```
          1130      1140      1150      1160
1104 TCTCATGTTGCCAGCGGGTAATGCCGGGGACTCGTGAGAG M.avium
1056 TCTCATGTTGCCAGCGGGTAATGCCGGGGACTCGTGAGAG M.intracellulare
1098 TCTCATGTTGCCAGCGGGTAATGCAGGGGACTCGTGAGAG M.paratuberc.
1064 TCTCATGTTGCCAGCGGGTAATGCCGGGGACTCGTGAGAG M.scrofulaceum
1069 TCTCATGTTGCCAGCACGTAATGGTGGGGACTCGTGAGAG M.tuberculosis
1208 TCTCATGTTGCCAGCACGTAATGGTGGGGACTCGTGAGAG M.bovis
1119 TCTCATGTTGCCAGCACGTAATGGTGGGGACTCGTGAGAG M.leprae
1066 TCTCATGTTGCCAGCGGGTAATGCCGGGGACTCGTGAGAG M.kansasii
1067 TCTCATGTTGCCAGCGGGTAATGCCGGGGACTCGTGAGAG M.gastri
1100 TCTCATGTTGCCAGCGGGTAATGCCGGGGACTCGTGAGAG M.gordonae
1061 TCTCATGTTGCCAGCACGTAATGGTGGGGACTCGTGAGAG M.marinum
```

▪ ▪ ▪ ▪

```
          1290      1300      1310      1320
1264 CGAATCCTTTTAAAGCCGGACTCAGTTCGGATTGGGGTCT M.avium
1216 CGAATCCTTTTAAAGCCGGTCTCAGTTCGGATTGGGGTCT M.intracellulare
1258 CGAATCCTTTTAAAGCCGGACTCAGTTCGGATTGGGGTCT M.paratuberc.
1224 CGAATCCTTTTAAAGCCGGTCTCAGTTCGGATCGGGGTCT M.scrofulaceum
1229 CGAATCCTTA-AAAGCCGGTCTCAGTTCGGATCGGGGTCT M.tuberculosis
1368 CGAATCCTTA-AAAGCCGGTCTCAGTTCGGATCGGGGTCT M.bovis
1279 CGAATCCTTTTAAAGCCGGTCTCAGTTCGGATCGGGGTCT M.leprae
1226 CGAATCCTTTTAAAGCCGGTCTCAGTTCGGATCGGGGTCT M.kansasii
1227 CGAATCCTTTTAAAGCCGGTCTCAGTTCGGATCGGGGTCT M.gastri
1260 CGAATCCTTTTAAAGCCGGTCTCAGTTCGGATCGGGGTCT M.gordonae
1221 CGAATCCTTT-AAAGCCGGTCTCAGTTCGGATCGGGGTCT M.marinum
```

```
          1330      1340      1350      1360
1304 GCAACTCGACCCCATGAAGTCGGAGTCGCTAGTAATCGCA M.avium
1256 GCAACTCGACCCCATGAAGTCGGAGTCGCTAGTAATCGCA M.intracellulare
1298 GCAACTAGACCCAATGAAGTCGGAGTCGCTAGTAATCGCA M.paratuberc.
1264 GCAACTCGACCCCGTGAAGTCGGAGTCGCTAGTAATCGCA M.scrofulaceum
1268 GCAACTCGACCCCGTGAAGTCGGAGTCGCTAGTAATCGCA M.tuberculosis
1407 GCAACTCGACCCCGTGAAGTCGGAGTCGCTAGTAATCGCA M.bovis
1319 GCAACTCGACCCCGTGAAGTCGGAGTCGCTAGTAATCGCA M.leprae
1266 GCAACTCGACCCCGTGAAGTCGGAGTCGCTAGTAATCGCA M.kansasii
1267 GCAACTCGACCCCGTGAAGTCGGAGTCGCTAGTAATCGCA M.gastri
1300 GCAACTCGACCCCGTGAAGTCGGAGTCGCTAGTAATCGCA M.gordonae
1260 GCAACTCGACCCCGTGAAGTCGGAGTCGCTAGTAATCGCA M.marinum
```

Figure 5B 2550 2568 2569 2589

M.avium 23S: TTACGCGCGGCAGGACGAAAAGACCCCGGGACCTTCACTA

Figure 6

PROBES FOR THE DETECTION OF MYCOBACTERIA

This a divisional of Ser. No. 08/943,777, filed Oct. 3, 1997 now abandoned.

The present application claims priority under 35 USC 119(e) (1) from Provisional Application Nos. 60/028,392 filed on Oct. 15, 1996, 60/029,595 filed on Oct. 23, 1996 and 60/045,962, filed on May 8, 1997.

The present invention relates to novel probes and to mixtures of such probes, in addition to the design, construction and use of such novel probes or mixtures thereof for detecting a target sequence of one or more mycobacteria, which probes are capable of detecting such organism(s) optionally present in a test sample, e.g. sputum, laryngeal swabs, gastric lavage, bronchial washings, biopsies, aspirates, expectorates, body fluids (spinal, pleural, pericardial, synovial, blood, pus, bone marrow), urine, tissue sections as well as food samples, soil, air and water samples and cultures thereof. The invention relates in particular to novel probes and mixtures thereof for detecting the presence of one or more mycobacteria of the *Mycobacterium tuberculosis* Complex (MTC) and for detecting the presence of one or more mycobacteria other than mycobacteria of the *Mycobacterium tuberculosis* Complex (MOTT). The invention further relates to diagnostic kits comprising one or more of such probes. The probes of the present invention are surprisingly able to penetrate the cell wall of the mycobacteria, thus making possible the development of fast an easy-performed in situ protocols.

BACKGROUND OF THE INVENTION

Tuberculosis is a very life-threatening and highly epidemic disease which is caused by infection with *Mycobacterium tuberculosis.* Tuberculosis is presently the predominant infectious cause of morbidity and mortality worldwide, and is estimated to kill about three million people annually. WHO estimates that the annual number of new cases of tuberculosis will increase from 7.5 million in 1990 to 10.2 million in 2000, an escalation that will result in approximately 90 million new cases during this decade. It is furthermore estimated that 30 million people will die from tuberculosis during the 1990s, which equals one quarter of preventable deaths among adults.

The prevalence of tuberculosis has been very high in the poorer parts of the world such as Asia, Africa and South-America, but in recent years an increase has also been observed in industrialised countries. This appears to be due to an interaction of various factors including i.a. patterns of migration, poorly organised tuberculosis programmes and nutrition problems. Furthermore, a serious threat will arise from the emergence of new strains that are drug resistant or worse, multi-drug resistant.

Mycobacteria are often divided into *tuberculous* mycobacteria, i.e. mycobacteria of the *Mycobacterium tuberculosis* Complex (MTC), and non-tuberculous mycobacteria, i.e. mycobacteria other than those of the *Mycobacterium tuberculosis* Complex (MOTT). The MTC group comprises apart from *M. tuberculosis, M. bovis, M. africanum* and *M. microti.* Mycobacteria of the MOTT group are not normally pathogenic to healthy individuals but may cause disease in immunocompromised individuals, e.g. individuals infected with HIV. Clinical relevant mycobacteria of the MOTT group are in particular *M. avium, M. intracellulare, M. kansasii* and *M. gordonae,* but also *M. scrofulaceum, M. xenopi* and *M. fortuitum.*

*M. avium* and *M. intracellulare* together with *M. paratuberculosis* and *M. lepraemurium* constitute the *Mycobacterium avium* Complex (MAC). Extended with *M. scrofulaceum,* the group is named *Mycobacterium avium-intracellulare-scrofulaceum* Complex (MAIS).

It is well-known that treatment of mycobacterial infections with antibiotics may lead to the emergence of drug resistant strains. Many antibiotic drugs excert their effects by interfering with protein synthesis or with transcription. Studies of the molecular mechanisms underlying certain antibiotic resistance phenotypes in clinical mycobacterium isolates have revealed mutations in rRNA genes. The development of resistance because of mutation(s) located in the rRNA gene is likely to occur since slow-growing mycobacteria have only a single rRNA operon. All mycobacteria populations comprise a minority of drug resistant mutants that have arisen by spontaneous mutation. These mutated mycobacteria do normally not survive particularly well, but, when single-drug therapy is offered as treatment, the drug susceptible bacteria are killed, and only the resistant mutants will survive and multiply, and, thus at some point, constitute the majority of the mycobacteria population. The selection of drug resistant bacteria due to inadequate drug therapy leads to a state of so-called “acquired drug-resistance”. In contrast, “primary drug-resistance” is used to characterise a situation where drug-resistant mycobacteria can be isolated from a patient who has never been treated for mycobacterial infection, and has infected with drug-resistant mycobacteria from an individual suffering from infection with an acquired drug resistant bacterium.

Today, drug-resistance is determined primarily phenotypically by culturing clinical samples, in which presence of mycobacteria have been demonstrated, in the presence of the individual drugs. This is unfortunately a very slow and time-consuming procedure as the result of the drug-resistance studies depends on the growth rate of the mycobacteria, which are well-known to be slow. Thus, the result is not available until after several weeks.

Although the incidence of drug-resistance is, at least not yet, very common, it is nevertheless very important that resistant strains are identified and eradicated. Therefore, it is of major importance to find a reliable and rapidly performed method of diagnosing drug-resistance.

Presently, the detection of mycobacteria by microscopy is the most prevalent method for diagnosis. The sample (e.g. an expectorate) is stained for the presence of acid-fast bacilli using e.g. Ziehl-Neelsen staining. However, staining for acid-last bacilli does not provide the necessary information about the type of infection, only whether acid fast bacilli are present in the sample, and this is in itself not sufficient information for establishing a diagnosis. Samples positive for acid fast bacilli may subsequently be cultured in order to be able to perform species identification.

Since Ziehl-Neelsen staining cannot be used to determine whether the infection is caused by mycobacteria of the MTC group or mycobacteria other than mycobacteria of the MTC group, a positive staining frequently leads to very costly isolation of all the patients with suspected *M. tuberculosis* infection as well as treatment with medicaments to which the patient may not even respond.

Since the sensitivity of acid fast staining is only approximately $10^4$–$10^5$ per ml smear negative samples should also be cultured as culture-based tests are sensitive, and as it may be possible to detect 10–100 organisms per sample, but the result is not available before up to 8 weeks of culturing. Likewise, information about drug susceptibility is not available until after 1–3 weeks of further testing.

Different solid or liquid media (Loewenstein Jensen slants and Dubos broth) have traditionally been used for culturing of mycobacteria-containing samples. Newer media include ESP Myco Culture System (Difco), MB/BacT (Organon Teknika), BacTec (Becton Dickinson) and MGIT (Becton Dickinson). These test media are based on colourmetric or fluorometric detection of carbon dioxide or oxygen produced by mycobacterial metabolism, and adapted to automated systems for large scale testing.

Species identification is presently carried out following culturing using traditional biochemical methods or probe hybridisation assays (e.g. AccuProbe by Gen-Probe Inc, USA). There is, therefore, an increasing need for means allowing a more rapid distinction between mycobacteria of the MTC group and mycobacteria other than those of the MTC group, and for further species identification of those especially mycobacteria other than those of the MTC group.

A number of new attempts to replace the culture-based methods relies on molecular amplification technology. Several methods have emerged, among them the polymerase chain reaction (PCR), the ligase chain reaction and transcription mediated amplification. The basic principle of amplification methods is that a specific nucleic acid sequence of the mycobacteria is amplified to increase the copy number of the specific sequence to a level where the amplicon may be detectable. In principle, the methods offers the possibility of detecting only one target sequence, thus, in principle, making detection of mycobacteria present at low levels possible. However, it has become dear that the target amplification methods cannot replace culture-based methods as only samples which are positive by staining for acid fast bacilli (AFB) give a satisfactory sensitivity. Furthermore, specific problems exist for each method. The PCR method may give false negative results due to the presence of inhibitors such as hemoglobin. Another problem arises from cross-contamination of negative specimens and/or reagents with amplified nucleic acid present in the laboratory environment leading to false positive results. A disadvantage is that costly reagents are needed for performing these tests. Furthermore, specialised instrumentation is required, making these tests mainly useful in large specialised laboratories, and generally not applicable in smaller clinical laboratories.

Nucleic acid probes for detecting rRNA of mycobacteria have been described in for example U.S. Pat. No. 5,547,842, EP-A 0 572 120 and U.S. Pat. No. 5,422,242.

Considering the perspective and impact the disease has, the development of rapid and preferably easy-performed and further economic feasible diagnostic detection tests are of utmost importance and would be a very valuable tool in the fight against the spread of tuberculosis.

Peptide nucleic acids are pseudo-peptides with DNA-binding capability. The compounds were first reported in the early nineties in connection with a series of attempts to design nucleotide analogues capable of hybridising, in a sequence-specific fashion, to DNA and RNA, cf. WO 92/20702.

Hybridisation of peptide nucleic acid probes to DNA and to RNA has been shown to obey the Watson-Crick base pairing rules, and peptide nucleic acid probes have been found to hybridise to a DNA or a RNA target with higher affinity and specificity than the nucleic acid counterparts. These properties are ascribed to the uncharged, as opposed to the charged, structure of the peptide nucleic acid and DNA or RNA backbones, respectively, and to the high conformational flexibility of the peptide nucleic acid molecules. These features—together with the documented stability of peptide nucleic acid towards a variety of naturally occurring nucleases and proteases that usually degrade DNA, RNA or proteins—invite for use of peptide nucleic acid probes as antisense therapeutic agents and opens potentially important applications in diagnostics.

SUMMARY OF THE INVENTION

The present invention relates to novel peptide nuclic acid probes and to mixtures of such probes for detecting a target sequence of one or more mycobacteria optionally present in a sample.

In a first aspect, the present invention relates to peptide nucleic acid probes for detecting a target sequence of one or more mycobacteria optionally present in a sample, said probes being capable of hybridising to a target sequence of mycobacterial rDNA, precursor rRNA or rRNA forming detectable hybrids. In another aspect, the invention relates to peptide nucleic acid probes, said probe being capable of hybridising to a target sequence of mycobacterial rDNA, precursor rRNA, or 23S, 16S or 5S rRNA forming detectable hybrids.

The peptide nucleic acid probes according to the present invention are capable of hybridising to a target sequence of mycobacterial rDNA, precursor rRNA, or 23S, 16S or 5S rRNA forming detectable hybrids, said target sequence being obtainable by (a) comparing the nucleobase sequences of said mycobacterial rRNA or rDNA of one or more mycobacteria to be detected with the corresponding nucleobase sequence of organism(s), in particular other mycobacteria, from which said one or more mycobacteria are to be distinguished, (b) selecting a target sequence of said rRNA or rDNA which includes at least one nucleobase differing from the corresponding nucleobase of the organism(s), in particular other mycobacteria, from which said one or more mycobacteria are to be distinguished, and (c) determining the capability of said probe to hybridise to the selected target sequence to form detectable hybrids.

Furthermore, the peptide nucleic acid probes according to the invention are capable of hybridising to a target sequence of mycobacterial rDNA, precursor rRNA or 23S, 16S or 5S rRNA forming detectable hybrids, said probe being obtainable by (a) comparing the nucleobase sequences of said mycobacterial rRRA or rDNA of one or more mycobacteria to be detected with the corresponding nucleobase sequence of organism(s), in particular other mycobacteria, in particular other mycobacteria, from which said one or more mycobacteria are to be distinguished, (b) selecting a target sequence of said rRNA or rDNA which includes at least one nucleobase differing from the corresponding nucleobase of the organism(s), in particular other mycobacteria, from which said one or more mycobacteria are to be distinguished, (c) synthesising said probe, and (d) determining the capability of said probe to hybridise to the selected target sequence to form detectable hybrids.

In a further aspect, the invention relates to novel peptide nucleic acid probes for detecting a target sequence of one or more mycobacteria of the *Mycobacteruim tuberculosis* Complex (MTC), or for detecting a target sequence of one or more mycobacteria other than mycobacteria of the *Mycobacterium tuberculosis* Complex (MOTT) optionally present in a sample, which probes comprises from 6 to 30 polymerised peptide nucleic acid moieties, said probe being capable of hybridising to a target sequence of mycobacterial rDNA, precursor rRNA or 23S, 16S or 5S rRNA forming detectable hybrids. Suitable probes are those of formula (I) comprising from 10 to 30 polymerised moieties of formula (I)

(I)

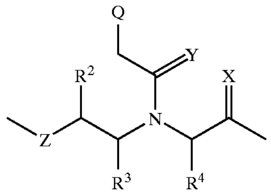

wherein each X and Y independently designate O or S, each Z independently designates O, S, $NR^1$, or $C(R^1)_2$, wherein each $R^1$ independently designate H, $C_{1-6}$ alkyl, $C_{1-6}$ alkenyl, $C_{1-6}$ alkynyl, each $R^2$, $R^3$ and $R^4$ designate independently H, the side chain of a naturally occurring amino acid, the side chain of a non-naturally occurring amino acid, $C_{1-4}$ alkyl, $C_{1-4}$ alkenyl or $C_{1-4}$ alkynyl, or a functional group, each Q independently designates a naturally occurring nucleobase, a non-naturally occurring nucleobase, an intercelator, a nucleobase-binding group, a label or H, with the proviso that the probe comprising such subsequence is capable of forming detectable hybrids with the target sequence of said mycobacterial rDNA, precursor rRNA or 23S, 16S or 5S rRNA.

Suitable probes for detecting a target sequence of 23S rRNA of one or more mycobacteria of the *Mycobacterium tuberculosis* Complex (MTC) optionally present in a sample comprise from 10 to 30 polymerised moieties of formula (I) as defined above, with the proviso that the Qs of adjacent moieties are selected so as to form a sequence of which a subsequence includes at least one nucleobase that is complementary to a nucleobase of *M. tuberculosis* 23S rRNA differing from the corresponding nucleobase of at least *M. avium* located within the following domains Positions 149–158 in FIG. 1A,
Positions 220–221 in FIG. 1A,
Positions 328–361 in FIG. 1A and FIG. 1B,
Positions 453–455 in FIG. 1B,
Positions 490–501 in FIG. 1B,
Positions 637–660 in FIG. 1C,
Positions 706–712 in FIG. 1D,
Positions 762–789 in FIG. 1D,
Position 989 In FIG. 1D,
Positions 1068–1072 in FIG. 1D,
Position 1148 in FIG. 1E,
Positions 1311–1329 in FIG. 1E,
Positions 1361–1364 in FIG. 1F,
Position 1418 in FIG. 1F,
Positions 1563–1570 in FIG. 1F,
Positions 1627–1638 in FIG. 1G,
Positions 1675–1677 in FIG. 1G,
Position 1718 in FIG. 1G,
Positions 1734–1740 in FIG. 1H,
Positions 1967–1976 in FIG. 1H,
Positions 2403–2420 in FIG. 1H,
Positions 2457–2488 in FIG. 1I,
Positions 2952–2956 in FIG. 1I,
Positions 2966–2969 in FIG. 1J,
Positions 3000–3003 in FIG. 1J or
Positions 3097–3106 in FIG. 1J, and further with the proviso that the probe comprising such subsequence is capable of forming detectable hybrids with a target sequence of said mycobacterial 23S rRNA.

Suitable probes for detecting a target sequence of 16S rRNA of one or more mycobacteria of the *Mycobacterium tuberculosis* Complex (MTC) optionally present in a sample comprise from 10 to 30 polymerised moieties of formula (I) as defined above, with the proviso that the Qs of adjacent moieties are selected so as to form a sequence of which a subsequence includes at least one nucleobase that is complementary to a nucleobase of *M. tuberculosis* 16S rRNA differing from the corresponding nucleobase of at least *M. avium* located within the following domains Positions 76–79 in FIG. 2A,
Positions 98–101 in FIG. 2A,
Positions 135–136 in FIG. 2A,
Positions 194–201 in FIG. 2B,
Positions 222–229 in FIG. 2B,
Position 242 in FIG. 2B,
Position 474 in FIG. 2C,
Positions 1136–1145 in FIG. 2C,
Positions 1271–1272 in FIG. 2C,
Positions 1287–1292 in FIG. 2D,
Position 1313 in FIG. 2D, or
Position 1334 in FIG. 2D, and further with the proviso that the probe comprising such subsequence is capable of forming detectable hybrids with a target sequence of said mycobacterial 16S rRNA.

Suitable probes for detecting a target sequence of 5S rRNA of one or more mycobacteria of the *Mycobacterium tuberculosis* Complex (MTC) optionally present in a sample comprise from 10 to 30 polymerised moieties of formula (I) as defined above, with the proviso that the Qs of adjacent moieties are selected so as to form a sequence of which a subsequence includes at least one nucleobase that is complementary to a nucleobase of *M. tuberculosis* 5S rRNA differing from the corresponding nucleobase of at least *M. avium* located within the following domain Positions 86–90 in FIG. 3 and further with the proviso that the probe comprising such subsequence is capable of forming detectable hybrids with a target sequence of said mycobacterial 5S rRNA.

In a preferred aspect, the invention relates to peptide nucleic acid probes for detecting a target sequence of 23S or 16S rRNA of one or more mycobacteria of the *Mycobacterium tuberculosis* Complex (MTC) optionally present in a sample comprising from 10 to 30 polymerised moieties of formula (I) as defined above, with the proviso that the Qs of adjacent moieties are selected so as to form a sequence of which a subsequence includes at least one nucleobase that is complementary to a nucleobase of *M. tuberculosis* 23S or 16S rRNA differing from the corresponding nucleobase of at least *M. avium* located within the following domains Positions 149–158 in FIG. 1A,
Positions 328–361 in FIG. 1A and FIG. 1B, Positions 490–501 in FIG. 1B,
Positions 637–660 in FIG. 1C,
Positions 762–789 in FIG. 1D,
Positions 1068–1072 in FIG. 1D,
Positions 1311–1329 in FIG. 1E,
Positions 1361–1364 in FIG. 1F,
Positions 1563–1570 in FIG. 1F,
Positions 1627–1638 in FIG. 1G,
Positions 1734–1740 in FIG. 1H,
Positions 2457–2488 in FIG. 1I,
Positions 2952–2956 in FIG. 1I,
Positions 3097–3106 in FIG. 1J,
Positions 135–136 in FIG. 2A, or
Positions 1287–1292 in FIG. 2D, and further with the proviso that the probe comprising such subsequence is capable of forming detectable hybrids with a target sequence of said mycobacterial 23S or 16S rRNA.

In a further embodiment, the present invention relates to peptide nucleic acid probes for detecting a target sequence of 23S rRNA of one or more mycobacteria other than mycobacteria of the *Mycobacterium tuberculosis* Complex (MOTT) optionally present in a sample comprising from 10 to 30 polymerised moieties of formula (I) as defined above, with the proviso that the Qs of adjacent moieties are selected so as to form a sequence of which a subsequence includes at least one nucleobase that is complementary to a nucleobase of *M. avium* 23S rRNA differing from the corresponding nucleobase of at least *M. tuberculosis* located within the following domains Positions 99–101 in FIG. 4A,
Position 183 in FIG. 4A,
Positions 261–271 in FIG. 4A,
Positions 281–284 in FIG. 4B,
Positions 290–293 in FIG. 4B,
Positions 327–335 in FIG. 4B,
Positions 343–357 in FIG. 4B,
Positions 400–405 in FIG. 4B and FIG. 4C,
Positions 453–462 in FIG. 4C,
Positions 587–599 in FIG. 4C,
Positions 637–660 in FIG. 4D,
Positions 704–712 in FIG. 4D,
Positions 763–789 in FIG. 4E,
Positions 1060–1074 in FIG. 4E,
Positions 1177–1185 in FIG. 4E,
Positions 1259–1265 in FIG. 4F,
Positions 1311–1327 in FIG. 4F,
Positions 1345–1348 in FIG. 4F,
Positions 1361–1364 in FIG. 4G,
Positions 1556–1570 in FIG. 4G,
Positions 1608–1613 in FIG. 4H,
Positions 1626–1638 in FIG. 4H,
Positions 1651–1659 in FIG. 4H,
Positions 1675–1677 in FIG. 4H,
Positions 1734–1741 in FIG. 4H,
Positions 1847–1853 in FIG. 4I,
Positions 1967–1976 in FIG. 4I,
Positions 2006–2010 in FIG. 4I,
Positions 2025–2027 in FIG. 4I,
Positions 2131–2132 in FIG. 4J,
Positions 2252–2255 in FIG. 4J,
Positions 2396–2405 in FIG. 4J and FIG. 4K,
Positions 2416–2420 in FIG. 4K,
Positions 2474–2478 in FIG. 4K,
Position 2687 in FIG. 4K,
Position 2719 in FIG. 4K,
Position 2809 in FIG. 4L,
Positions 3062–2068 in FIG. 4L, or
Positions 3097–3106 in FIG. 4L, and further with the proviso that the probe comprising such subsequence is capable of forming detectable hybrids with a target sequence of said mycobacterial 23S rRNA.

The invention further relates to peptide nucleic acid probes for detecting a target sequence of 16S rRNA of one or more mycobacteria other than mycobacteria of the *Mycobacterium tuberculosis* Complex (MOTT) optionally present in a sample comprising from 10 to 30 polymerised moieties of formula (I) as defined above, with the proviso that the Qs of adjacent moieties are selected so as to form a sequence of which a subsequence includes at least one nucleobase that is complementary to a nucleobase of *M. avium* 16S rRNA differing from the corresponding nucleobase of at least *M. tuberculosis* located within the following domains Positions 135–136 in FIG. 5A,
Positions 472–475 in FIG. 5A,
Positions 1136–1144 in FIG. 5A,
Positions 1287–1292 in FIG. 5B,
Position 1313 in FIG. 5B, or
Position 1334 in FIG. 5B, and further with the proviso that the probe comprising such subsequence is capable of forming detectable hybrids with a target sequence of said mycobacterial 16S rRNA.

In a preferred embodiment, the invention relates to peptide nucleic acid probes for detecting a target sequence of 23S or 16S rRNA of one or more mycobacteria other than mycobacteria of the *Mycobacterium tuberculosis* Complex (MOTT) optionally present in a sample, which probes comprise from 10 to 30 polymerised moieties of formula (I) as defined above, with the proviso that the Qs of adjacent moieties are selected so as to form a sequence of which a subsequence includes at least one nucleobase that is complementary to a nucleobase of *M. avium* 23S or 16S rRNA differing from the corresponding nucleobase of at least *M. tuberculosis* located within the following domains Positions 99–101 in FIG. 4A,
Positions 290–293 in FIG. 4B,
Positions 400–405 in FIG. 4B and FIG. 4C,
Positions 453–462 in FIG. 4C,
Positions 637–660 in FIG. 4D,
Positions 763–789 in FIG. 4E,
Positions 1311–1327 in FIG. 4F,
Positions 1361–1364 in FIG. 4G,
Positions 1734–1741 in FIG. 4H,
Positions 2025–2027 in FIG. 4I,
Positions 2474–2478 in FIG. 4K,
Positions 3062–2068 in FIG. 4L, or
Positions 1287–1292 in FIG. 5B, and further with the proviso that the probe comprising such subsequence is capable of forming detectable hybrids with a target sequence of said mycobacterial 23S or 16S rRNA.

In another embodiment, the present invention relates to peptide nucleic acid probes for detecting a target sequence of 23S, 16S or 5S rRNA of one or more mycobacteria of the *Mycobacterium tuberculosis* Complex (MTC) or for detecting a target sequence of 23S, 16S or 5S rRNA of one or more mycobacteria other than mycobacteria of the *Mycobacterium tuberculosis* Complex (MOTT), in particular drug resistant mycobacteria, optionally present in a sample, which probes comprise from 10 to 30 polymerised moieties of formula (I) as defined above, with the proviso that the Qs of adjacent moieties are selected so as to form a sequence of which a subsequence includes at least one nucleobase that is complementary to a nucleobase that differs from the corresponding nucleobase of 23S, 16S or 5S rRNA of said one or more mycobacteria located within the following domains Positions 2568–2569 in FIG. 6,
Position 452 in FIG. 7,
Positions 473–477 in FIG. 7, or
Positions 865–866 in FIG. 7, and further with the proviso that the probe comprising such subsequence is capable of forming detectable hybrids with the target sequence of said mycobacterial 23S, 16S or 5S rRNA.

In preferred embodiments, the peptide nucleic acid probes according to the invention are those of formula (II), (III), or (IV)

(II)

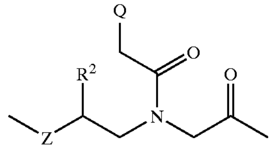

(III)

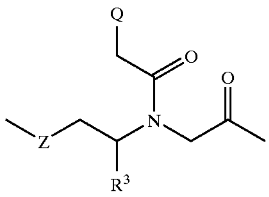

(IV)

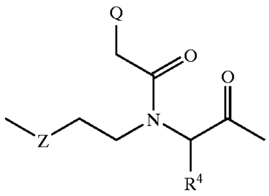

wherein Z, $R^2$, $R^3$, and $R^4$, and Q is as defined above, and further with the provisos defined above. In may especially be preferred that Z is NH, $NCH_3$ or O, each $R^2$, $R^3$ and $R^4$ independently designate H or the side chain of a naturally occurring amino acid, the side chain of a non-naturally occurring amino acid, or $C_{1-4}$ alkyl, and each Q is a naturally occurring nucleobase or a non-naturally occurring nucleobase. In a further preferred embodiment, Z is NH or O, and $R^2$ is H or the side chain of Ala, Asp, Cys, Glu, His, HomoCys, Lys, Orn, Ser or Thr, and Q is a nucleobase selected from thymine, adenine, cytosine, guanine, uracil, iso-C and 2,6-diaminopurine. The peptide nucleic acid probes may suitably be those of formula (V)

(V)

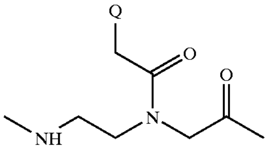

wherein $R^4$ is H or the side chain of Ala, Asp, Cys, Glu, His, HomoCys, Lys, Orn, Ser or Thr, and Q is as defined above, and with the provisos defined above.

Such peptide nucleic acid probes may further comprise one or more labels and a mixture of such probes, which labels may be mutually identical or different, which probes optionally may comprise one or more linkers, and which probes may be mutually identical or different with the provisos defined above.

For many applications, it is preferred that the nucleobase sequence of the peptide nucleic acid probes is substantially complementary to the nucleobase sequence of the target sequence. In preferred embodiments, the nucleobase sequence of said probe is complementary to the nucleobase sequence of said target sequence.

Peptide nucleic acid probes for detecting a target sequence of one or more mycobacteria of the *Mycobacterium tuberculosis* Complex (MTC) or for deflecting a target sequence of one or more mycobacteria other than mycobacteria of the *Mycobacterium tuberculosis* Complex (MOTT) are suitably those wherein the Qs of adjacent moieties are selected so as to form the following subsequences

| | |
|---|---|
| AGA TGC GGG TAG CAC (selected from positions 149–158 in FIG. 1A), | (Seq ID no 1) |
| TGT TTT CTC CTC CTA (selected from positions 220–221 in FIG. 1A), | (Seq ID no 2) |
| ACT GCC TCT CAG CCG (selected from positions 328–361 in FIG. 1A and FIG. 1B), | (Seq ID no 3) |
| TGA TAC TAG GCA GGT (selected from positions 453–455 in FIG. 1B), | (Seq ID no 4) |
| CGG ATT CAC AGC GGA (selected from positions 490–501 in FIG. 1B), | (Seq ID no 5) |
| TCA CCA CCC TCC TCC (selected from positions 637–660 in FIG. 1C), | (Seq ID no 6) |
| CCA CCC TCC TCC (selected from positions 637–660 in FIG. 1C), | (modified Seq ID no 6) |
| TTA ACC TTG CGA CAT (selected from positions 706–712 in FIG. 1C), | (Seq ID no 7) |
| ACT ATT CAC ACG CGC (selected from positions 762–789 in FIG. 1D), | (Seq ID no 8) |
| CTC CGC GGT GAA CCA (selected from position 989 in FIG. 1D), | (Seq ID no 9) |
| GCT TTA CAC CAC GGC (selected from positions 1068–1072 in FIG. 1D), | (Seq ID no 10) |
| ACG CTT GGG GGC CTT (selected from position 1148 in FIG. 1E), | (Seq ID no 11) |
| CCA CAC CCA CCA CAA (selected from positions 1311–1329 in FIG. 1E), | (Seq ID no 12) |
| CCG GTG GCT TCG CTG (selected from positions 1361–1364 in FIG. 1F), | (Seq ID no 13) |
| ACT TGC CTT GTC GCT (selected from position 1418 in FIG. 1F), | (Seq ID no 14) |
| GAT TCG TCA CGG GCG (selected from positions 1563–1570 in FIG. 1F), | (Seq ID no 15) |
| AAC TCC ACA CCC CCG (selected from positions 1627–1638 in FIG. 1G), | (Seq ID no 16) |
| ACT CCA CAC CCC CGA (selected from positions 1627–1638 in FIG. 1G), | (Seq ID no 17) |
| ACC CCT TCG CTT GAC (selected from positions 1675–1677 in FIG. 1G), | (Seq ID no 18) |
| CTT GCC CCA GTG TTA (selected from position 1718 in FIG. 1G), | (Seq ID no 19) |

-continued

| | |
|---|---|
| CTC TCC CTA CCG GCT (selected from positions 1734–1740 in FIG. 1H), | (Seq ID no 20) |
| GAT ATT CCG GTC CCC (selected from positions 1967–1976 in FIG. 1H), | (Seq ID no 21) |
| ACT CCG CCC CAA CTG (selected from positions 2403–2420 in FIG. 1H), | (Seq ID no 22) |
| CTG TCC CTA AAC CCG (selected from positions 2457–2488 in FIG. 1I), | (Seq ID no 23) |
| TTC GAG GTT AGA TGC (selected from positions 2457–2488 in FIG. 1I), | (Seq ID no 24) |
| GTC CCT AAA CCC GAT (selected from positions 2457–2488 in FIG. 1I), | (Seq ID no 25) |
| GGT GCA CCA GAG GTT (selected from positions 2952–2956 in FIG. 1I), | (Seq ID no 26) |
| CTG GCG GGA CAA CTG (selected from positions 2966–2969 in FIG. 1J), | (Seq ID no 27) |
| TTA TCC TGA CCG AAC (selected from positions 3000–3003 in FIG. 1J), | (Seq ID no 28) |
| GAC CTA TTG AAC CCG (selected from positions 3097–3106 in FIG. 1J), | (Seq ID no 29) |
| GAA GAG ACC TTT CCG (selected from positions 76–79 in FIG. 2A), | (Seq ID no 30) |
| CAC TCG AGT ATC TCC (selected from positions 98–101 in FIG. 2A), | (Seq ID no 31) |
| ATC ACC CAC GTG TTA (selected from positions 136–136 in FIG. 2A), | (Seq ID no 32) |
| GCA TCC CGT GGT CCT (selected from positions 194–201 in FIG. 2B), | (Seq ID no 33) |
| CAC AAG ACA TGC ATC (selected from positions 194–201 in FIG. 2B), | (Seq ID no 34) |
| TAA AGC GCT TTC CAC (selected from positions 222–229 in FIG. 2B), | (Seq ID no 35) |
| GCT CAT CCC ACA CCG (selected from position 242 in FIG. 2B), | (Seq ID no 36) |
| CCG AGA GAA CCC GGA (selected from position 474 in FIG. 2C), | (Seq ID no 37) |
| AGT CCC CAC CAT TAC (selected from positions 1136–1145 in FIG. 2C), | (Seq ID no 38) |
| AAC CTC GCG GCA TCG (selected from positions 1271–1272 in FIG. 2C), | (Seq ID no 39) |
| GGC TTT TAA GGA TTC (selected from positions 1287–1292 in FIG. 2D), | (Seq ID no 40) |
| GAC CCC GAT CCG AAC (selected from position 1313 in FIG. 2D), | (Seq ID no 41) |
| CCG ACT TCA CGG GGT (selected from position 1334 in FIG. 2D), | (Seq ID no 42) |
| CGG AGG GGC AGT ATC (selected from positions 86–90 in FIG. 3), | (Seq ID no 43) |
| GAT CAA TGC TCG GTT (selected from positions 99–101 in FIG. 4A), | (Seq ID no 44) |
| TTC CCC GCG TTA CCT (selected from position 183 in FIG. 4A), | (Seq ID no 45) |
| TTA GCC TGT TCC GGT (selected from positions 261–271 in FIG. 4A), | (Seq ID no 46) |
| GCA TGC GGT TTA GCC (selected from positions 281–284 in FIG. 4B), | (Seq ID no 47) |
| TAC CCG GTT GTC CAT (selected from positions 290–293 in FIG. 4B), | (Seq ID no 48) |
| GTA GAG CTG AGA CAT (selected from positions 327–335 and 343–357 in FIG. 4B), | (Seq ID no 49) |
| GCC GTC CCA GGC CAC (selected from positions 400–405 in FIG. 4B and FIG. 4C), | (Seq ID no 50) |
| CTC GGG TGT TGA TAT (selected from positions 453–462 in FIG. 4C), | (Seq ID no 51) |
| ACT ATT TCA CTC CCT (selected from positions 587–599 FIG. 4C), | (Seq ID no 52) |
| ACG CCA TCA CCC CAC (selected from positions 637–680 in FIG. 4D), | (Seq ID no 53) |
| CGA CGT GTC CCT GAC (selected from positions 704–712 in FIG. 4D), | (Seq ID no 54) |
| ACT ACA CCC CAA AGG (selected from positions 763–789 in FIG. 4E), | (Seq ID no 55) |
| CAC GCT TTT ACA CCA (selected from positions 1060–1074 in FIG. 4E), | (Seq ID no 56) |
| GCG ACT ACA CAT CCT (selected from positions 1177–1185 in FIG. 4E), | (Seq ID no 57) |
| CGG CGC ATA ATC ACT (selected from positions 1259–1265 in FIG. 4F), | (Seq ID no 58) |

-continued

| | |
|---|---|
| CCA CAT CCA CCG TAA (selected from positions 1311–1327 in FIG. 4F), | (Seq ID no 59) |
| CGC TGA ATG GGG GAC (selected from positions 1345–1348 in FIG. 4F), | (Seq ID no 60) |
| GGA GCT TCG CTG AAT (selected from positions 1361–1364 in FIG. 4G), | (Seq ID no 61) |
| CGG TCA CCC GGA GCT (selected from positions 1361–1364 in FIG. 4G), | (Seq ID no 62) |
| GGA CGC CCA TAC ACG (selected from positions 1556–1570 in FIG. 4G), | (Seq ID no 63) |
| GAA GGG GAA TGG TCG (selected from positions 1608–1613 in FIG. 4H), | (Seq ID no 64) |
| AAT CGC CAC GCC CCC (selected from positions 1626–1638 in FIG. 4H), | (Seq ID no 65) |
| CAG CGA AGG TCC CAC (selected from positions 1651–1659 in FIG. 4H), | (Seq ID no 66) |
| GTC ACC CCA TTG CTT (selected from positions 1675–1677 in FIG. 4H), | (Seq ID no 67) |
| ATC GCT CTC TAC GGG (selected from positions 1734–1741 in FIG. 4H), | (Seq ID no 68) |
| GTG TAT GTG CTC GCT (selected from positions 1847–1853 in FIG. 4I), | (Seq ID no 69) |
| ACG GTA TTC CGG GCC (selected from positions 1967–1976 in FIG. 4I), | (Seq ID no 70) |
| GGC CGA ATC CCG CTC (selected from positions 2006–2010 in FIG. 4I), | (Seq ID no 71) |
| AAA CAG TCG CTA CCC (selected from positions 2025–2027 in FIG. 4I), | (Seq ID no 72) |
| CCT TAC GGG TTA ACG (selected from positions 2131–2132 in FIG. 4J), | (Seq ID no 73) |
| GAG ACA GTT GGG AAG (selected from positions 2252–2255 in FIG. 4J), | (Seq ID no 74) |
| TGG CGT CTG TGC TTC (selected from positions 2396–2405 in FIG. 4J and FIG. 4K), | (Seq ID no 75) |
| CGA CTC CAC ACA AAC (selected from positions 2416–2420 in FIG. 4K), | (Seq ID no 76) |
| GAT AAG GGT TCG ACG (selected from positions 2474–2478 in FIG. 4K), | (Seq ID no 77) |
| ATC CGT TGA GTG ACA (selected from position 2687 in FIG. 4K), | (Seq ID no 78) |
| CAG CCC GTT ATC CCC (selected from position 2719 in FIG. 4K), | (Seq ID no 79) |
| AAC CTT TGG GAC CTG (selected from position 2809 in FIG. 4L), | (Seq ID no 80) |
| TAA AAG GGT GAG AAA (selected from positions 3062–3068 in FIG. 4L), | (Seq ID no 81) |
| GTC TGG CCT ATC AAT (selected from positions 3097–3106 in FIG. 4L), | (Seq ID no 82) |
| AGA TTG CCC ACG TGT (selected from positions 135–136 in FIG. 5A), | (Seq ID no 83) |
| AAT CCG AGA AAA CCC (selected from positions 472–475 in FIG. 5A), | (Seq ID no 84) |
| GCA TTA CCC GCT GGC (selected from positions 1136–1144 in FIG. 5B), | (Seq ID no 85) |
| TTA AAA GGA TTC GCT (selected from positions 1287–1292 in FIG. 5B), | (Seq ID no 86) |
| AGA CCC CAA TCC GAA (selected from position 1313 in FIG. 5B), | (Seq ID no 87) |
| GAC TCC GAC TTC ATG (selected from position 1334 in FIG. 5B), | (Seq ID no 88) |
| GTC TTT TCG TCC TGC (selected from positions 2588–2589 in FIG. 6), | (Seq ID no 89) |
| GTC TTA TCG TCC TGC (selected from positions 2588 in FIG. 6), | (Seq ID no 90) |
| GTC TTC TCG TCC TGC (selected from positions 2568 in FIG. 6), | (Seq ID no 91) |
| GTC TTG TCG TCC TGC (selected from positions 2568 in FIG. 6), | (Seq ID ne 92) |
| GTC TAT TCG TCC TGC (selected from positions 2568 in FIG. 6), | (Seq ID no 93) |
| GTC TCT TCG TCC TGC (selected from positions 2568 in FIG. 6), | (Seq ID no 94) |
| GTC TGT TCG TCC TGC (selected from positions 2568 in FIG. 6), | (Seq ID no 95) |
| TTG GCC GGT GCT TCT (selected from positions 452 in FIG. 7), | (Seq ID no 98) |
| TTG GCC GGT ACT TCT (selected from positions 452 in FIG. 7), | (Seq ID no 97) |

-continued

| | |
|---|---|
| TTG GCC GGT CCT TCT (selected from positions 452 in FIG. 7), | (Seq ID no 98) |
| TTG GCC GGT TCT TCT (selected from positions 452 in FIG. 7), | (Seq ID no 99) |
| ACC GCG GCT GCT GGC (selected from positions 473–477 in FIG. 7), | (Seq ID no 100) |
| ACC GCG GCT ACT GGC (selected from positions 473 in FIG. 7), | (Seq ID no 101) |
| ACC GCG GCT CCT GGC (selected from positions 473 in FIG. 7), or | (Seq ID no 102) |
| ACC GCG GCT TCT GGC (selected from positions 473 in FIG. 7), | (Seq ID no 103) |
| CGG CAG CTG GCA CGT (selected from positions 474 in FIG. 7), | (Seq ID no 104) |
| CGG CCG CTG GCA CGT (selected from positions 474 in FIG. 7), | (Seq ID no 105) |
| CGG CTG CTG GCA CGT (selected from positions 474 in FIG. 7), | (Seq ID no 106) |
| CGT ATT ACC GCA GCT (selected from positions 477 in FIG. 7), | (Seq ID no 107) |
| CGT ATT ACC GCC GCT (selected from positions 477 in FIG. 7), | (Seq ID no 107) |
| CGT ATT ACC GCT GCT (selected from positions 477 in FIG. 7), | (Seq ID no 109) |
| TTC CTT TGA GTT TTA (selected from positions 865–866 in FIG.7), | (Seq ID no 110) |
| TTC CTT TAA GTT TTA (selected from positions 865 in FIG. 7), | (Seq ID no 111) |
| TTC CTT TCA GTT TTA (selected from positions 865 in FIG. 7), | (Seq ID no 112) |
| TTC CTT TTA GTT TTA (selected from positions 865 in FIG. 7), | (Seq ID no 113) |
| TTC CTT AGA GTT TTA (selected from positions 866 in FIG. 7), | (Seq ID no 114) |
| TTC CTT CGA GTT TTA (selected from positions 866 in FIG. 7), | (Seq ID no 115) |
| TTC CTT GGA GTT TTA (selected from positions 866 in FIG. 7), | (Seq ID no 116) |
| CAT GTG TCC TGT GGT | (Seq ID no 117) |
| CGT CAG CCC GAG AAA | (Seq ID no 118) |
| CAC TAC ACA CGC TCG | (Seq ID no 119) |
| TGG CGT TGA GGT TTC and | (Seq ID no 120) |
| AAC ACT CCC TTT GGA | (Seq ID no 123). |

In a preferred embodiment, such probes are those wherein the Qs of adjacent moieties are selected so as to form the following subsequences

| | |
|---|---|
| TCA CCA CCC TCC TCC | (Seq to no 6) |
| CCA CCC TCC TCC | (modified Seq ID no 6) |
| ACT ATT CAC ACG CGC | (Seq ID no 8) |
| CCA CAC CCA CCA CAA | (Seq ID no 12) |
| AAC TCC ACA CCC CCG | (Seq ID no 16) |
| ACT CCA CAC CCC CGA | (Seq ID no 17) |
| ACT CCG CCC CAA CTG | (Seq ID no 22) |
| CTG TCC CTA AAC CCG | (Seq ID no 23) |
| TTC GAG GTT AGA TGC | (Seq ID no 24) |
| GTC CCT AAA CCC GAT | (Seq ID no 25) |
| GAC CTA TTG AAC CCG | (Seq ID no 29) |
| GCA TCC CGT GGT CCT | (Seq ID no 33) |
| CAC AAG ACA TGC ATC | (Seq ID no 34) |
| GGC TTT TAA GGA TTC | (Seq ID no 40) |
| GAT CAA TGC TCG GTT | (Seq ID no 44) |
| CGA CTC CAC ACA AAC | (Seq ID no 76) |
| GCA TTA CCC GCT GGC | (Seq ID no 85) |
| GTC TTA TCG TCC TGC | (Seq ID no 90) |
| GTC TTC TCG TCC TGC | (Seq ID no 91) |
| GTC TTG TCG TCC TGC | (Seq ID no 92) |
| GTC TAT TCG TCC TGC | (Seq ID no 93) |
| GTC TCT TCG TCC TGC | (Seq ID no 94) |
| GTC TGT TCG TCC TGC | (Seq ID no 95) |
| AAC ACT CCC TTT GGA | (Seq ID no 123) |
| CAT GTG TCC TGT GGT | (Seq ID no 117) |
| CGT CAG CCC GAG AAA | (Seq ID no 118) |
| CAC TAC ACA CGC TCG | (Seq ID no 119) |
| TGG CGT TGA GGT TTC | (Seq ID no 120) |

In accordance herewith, the present invention relates to peptide nucleic acid probes selected from

| | |
|---|---|
| Lys(Flu)-Lys(Flu)-TCA CCA CCC TCC TCC-$NH_2$ | (OK 446/ modified Seq ID no 6) |
| Lys(Flu)-Lys(Flu)-CCA CCC TCC TCC-$NH_2$ | (OK 575/ modified Seq ID no 6) |
| Lys(Flu)-Lys(Flu)-ACT ATT CAC ACG CGC-$NH_2$ | (OK 447/ modified Seq ID no 8) |
| Lys(Flu)-ACT ATT CAC ACG CGC-$NH_2$ | (OK 688/ modified Seq ID no 8) |
| Lys(Flu)-Lys(Flu)-CCA CAC CCA CCA CAA-$NH_2$ | (OK 448/ modified Seq ID no 12) |
| Lys(Flu)-Lys(Flu)-AAC TCC ACA CCC CCG-$NH_2$ | (OK 449/ modified Seq ID no 16) |
| Lys(Flu)-Lys(Flu)-ACT CCA CAC CCC CGA-$NH_2$ | (OK 309/ modified Seq ID no 17) |
| Lys(Flu)-Lys(Flu)-ACT CCG CCC CAA CTG-$NH_2$ | (OK 450/ modified Seq ID no 22) |
| Lys(Flu)-Lys(Flu)-CTG TCC CTA AAC CCG-$NH_2$ | (OK 305/ modified Seq ID no 23) |
| Lys(Flu)-Lys(Flu)-TTC GAG GTT AGA TGC-$NH_2$ | (OK 306/ modified Seq ID no 24) |
| Lys(Flu)-TTC GAG GTT AGA TGC-$NH_2$ | (OK 682/ modified Seq ID no 24) |
| Lys(Flu)-Lys(Flu)-GTC CCT AAA CCC GAT-$NH_2$ | (OK 307/ modified Seq ID no 25) |
| Lys(Flu)-GTC CCT AAA CCC GAT-$NH_2$ | (OK 654/ modified Seq ID no 25) |
| Lys(Flu)-GAC CTA TTG AAC CCG-$NH_2$ | (OK 680/ modified Seq ID no 29) |
| Lys(Flu)-Lys(Flu)-Gly-GCA TCC CGT GGT CCT-$NH_2$ | (OK 223/ modified Seq ID no 33) |
| Lys(Flu)-Lys(Flu)-CAC AAG ACA TGC ATC-$NH_2$ | (OK 310/ modified Seq ID no 34) |
| Lys(Flu)-CAC AAG ACA TGC ATC-$NH_2$ | (OK 655/ modified Seq ID no. 34) |
| Lys(Flu)-GGC TTT TAA GGA TTC-$NH_2$ | (OK 689/ modified Seq ID no 40) |
| Lys(Rho)-GGC TTT TAA GGA TTC-$NH_2$ | (OK 689/ modified Seq ID no 40) |
| Flu-β-Ala-β-Ala-GAT CAA TGC TCG GTT-$NH_2$ | (OK 624/ modified Seq ID no 44) |
| Flu-β-Ala-β-Ala-CGA CTC CAC ACA AAC-$NH_2$ | (OK 612/ modified Seq ID no 76) |
| Flu-β-Ala-β-Ala-GCA TTA CCC GCT GGC-$NH_2$ | (OK 623/ modified Seq ID no 85) |
| Lys(Flu)-GTC TTT TCG TCC TGC-$NH_2$ | (OK 745/ modified Seq ID no 89) |
| Lys(Rho)-GTC TTA TCG TCC TGC-$NH_2$ | (OK 746/ modified Seq ID no 90) |
| Lys(Rho)-GTC TTC TCG TCC TGC-$NH_2$ | (OK 746/ modified Seq ID no 91) |

-continued

| | |
|---|---|
| Lys(Rho)-GTC TTG TCG TCC TGC-$NH_2$ | (OK 746/ modified Seq ID no 92) |
| Lys(Rho)-GTC TAT TCG TCC TGC-$NH_2$ | (OK 747/ modified Seq ID no 93) |
| Lys(Rho)-GTC TCT TCG TCC TGC-$NH_2$ | (OK 747/ modified Seq ID no 94) |
| Lys(Rho)-GTC TGT TCG TCC TGC-$NH_2$ | (OK 747/ modified Seq ID no 95) |
| Lys(Flu)-AAC ACT CCC TTT GGA-$NH_2$ | (OK 749/ modified Seq ID no 123) |

wherein Flu denotes a 5-(and 6)-carboxyfluoroescein label and Rho denotes a rhodamine label.

In a further aspect, the invention relates to the use of peptide nucleic acid probes as defined above or a mixture thereof for detecting a target sequence of one or more mycobacteria optionally present in a sample. In particular, the invention relates to the use of a peptide nucleic acid probe or a mixture thereof for detecting a target sequence of one or more mycobacteria of the *Mycobacterium tuberculosis* Complex (MTC), in particular a target sequence of *M. tuberculosis*, and further to the use of peptide nucleic acid probes or a mixture thereof for detecting a target sequence of one or more mycobacteria other than mycobacteria of the *Mycobacterium tuberculosis* Complex (MOTT), in particular a target sequence of one or more mycobacteria of the *Mycobacterium avium* Complex.

The invention further relates to a method for detecting a target sequence of one or more mycobacteria optionally present in a sample comprising (1) contacting any rRNA or rDNA present in said sample with one or more peptide nucleic acid probes as defined above or a mixture thereof under conditions, whereby hybridisation takes place between said probe(s) and said rRNA or rDNA, and (2) observing or measuring any formed detectable hybrids, and relating said observation or measurement to the presence of a target sequence of one or more mycobacteria in said sample.

In particular, the invention relates to a method for detecting a target sequence of one or more mycobacteria of the *Mycobacterium tuberculosis* Complex (MTC), in particular a target sequence of *M. tuberculosis*, or to a method for detecting a target sequence of one or more mycobacteria other than mycobacteria of the *Mycobacterium tuberculosis* Complex (MOTT). In preferred embodiments, the hybridisation takes place in situ, or takes place in vitro. In an embodiment, a signal amplifying system is used for measuring the resulting hybridisation. It is further preferred that the sample is a sputum sample.

Furthermore, the invention relates to kits for detecting a target sequence of one or more mycobacteria, in particular a target sequence of one or more mycobacteria of the *Mycobacterium tuberculosis* Complex (MTC), and in particular a target sequence of *M. tuberculosis,* and/or for detecting a target sequence of one or more mycobacteria other than mycobacteria of the *Mycobacterium tuberculosis* Complex (MOTT), in particular a target sequence of one or more mycobacteria of the *Mycobacterium avium* Complex (MAC), which kit comprise at least one peptide nucleic acid probe as defined above, and optionally a detection system with at least one detecting reagent in one embodiment thereof, the kit further comprises a solid phase capture system.

BRIEF DESCRIPTION OF THE FIGURES

Alignments of rDNA sequences of *M. tuberculosis* (as a representative of the MTC group) and important closely related species thereto, including *M. avium* (as a representative of the mycobacteria other than those of the MTC group) and important closely related species thereto for the 23S, 16S and/or 5S rRNA genes have been made (FIGS. 1A–1J, 2A–2D, 3, 4A–4L and 5A–B). The alignment for *M. bovis* and *M. intracellulare* are partly based on public available sequences and partly on sequences obtained by sequencing performed at DAKO A/S.

Alignment for the MTC gmp (23S rDNA)

FIGS. 1A–1J show alignments of 23S rDNA sequences of *M. tuberculosis* (GenBank entry GB:MTCY130, accession number Z73902), *M. avium* (GenBank entry GB:MA23SRNA, accession number X74494), *M. paratuberculosis* (GenBank entry GB:MPARRNA, accession number X74495), *M. phlei* (GenBank entry GB:MP23SRNA accession number X74493), *M. leprae* (GenBank entry GB:ML5S23S, accession number X56657), *M. gastri* (GenBank entry GB:MG23SRRNA, accession number Z17211), *M. kansasii* (GenBank entry GB:MK23SRRNA, accession number Z17212), and *M. smegmatis* (GB:MS16S23S5, accession number Y08453). Preferred peptide nucleic acid probes should enclose at least one nucleobase complementary to a nucleobase of *M. tuberculosis* 23S rRNA within positions 149–158, 220–221, 328–361, 453–455, 490–501, 637–660, 706–712, 762–789, 989, 1068–1072, 1148, 1311–1329, 1361–1364, 1418, 1563–1570, 1627–1638, 1675–1677, 1718, 1734–1740, 1967–1976, 2403–2420, 2457–2488, 2952–2956, 2966–2969, 3000–3003, and 3097–3106 of the alignment (indicated by heavy frames). Differences between the sequences of *M. avium, M. phlei, M. leprae. M. paratuberculosis, M. gastri* and *M. kansasii* and that of *M. tuberculosis* in the alignment are indicated by light frames.

Figure 7:
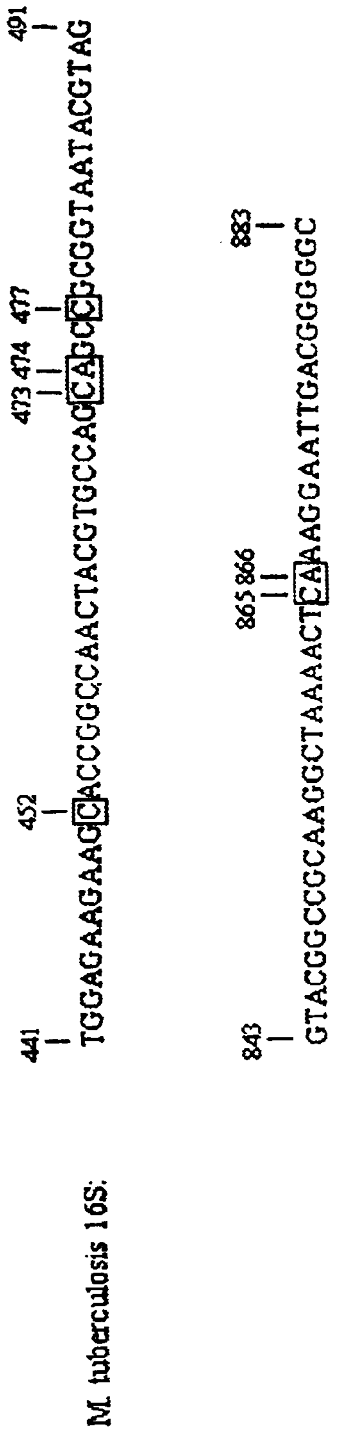

Alignment for the MTC group (16S rDNA)

FIGS. 2A–2D show alignments of 16S rDNA sequences of *M. tuberculosis* (GenBank entry GB:MTU16SRN, accession number X52917), *M. bovis* (GenBank entry GB:MSGTGDA, accession number M20940), *M. avium* (GenBank entry GB: MSGRRDA, accession number M61673), *M. intracellulare* (GenBank entry GB:MIN16SRN, accession number X52927), *M. paratuberculosis* (GenBank entry GB:MSGRRDH, accession number M61680), *M. scrofulaceum* (GenBank entry GB:MSC16SRN, accession number X52924), *M. leprae* (GenBank entry GB:MLEP16S1, accession number X55587), *M. kansasii* (GenBank entry GB:MKRRN16, accession number X15916), *M. gastri* (GenBank entry GB:MGA16SRN, accession number X52919), *M. gordonae* (GenBank entry GB:MSGRR16SI, accession number M29563) and *M. marinum* (GenBank entry GB:MMA16SRN, accession number X52920). Preferred peptide nucleic acid probes should enclose at least one nucleobase complementary to a nucleobase of *M. tuberculosis* 16S rRNA within positions 76–79, 98–101, 135–136, 194–201, 222–229, 242, 474, 1136–1145, 1271–1272, 1287–1292, 1313, and 1334 of the alignment (indicated by heavy frames).Differences between the sequences of *M. bovis, M. avium, M. intracellulare, M. paratuberculosis, M. scrofulaceum, M. leprae, M. kansasii, M. gastri, M. gordonae* and *M. marinum,* and that of *M. tuberculosis* in the alignment are indicated by light frames.

Alignment for the MTC group (5S rDNA)

FIG. 3 shows alignments of 5S rDNA sequences of *M. tuberculosis* (GenBank entry GB:MTDNA16S accession number x75601), *M. bovis* (GenBank entry GB:MBRRN5S, accession number X05526), *M. phlei* (GenBank entry GB:MP5SRRNA, accession number X55259), *M. leprae* (GenBank entry GB:ML5S23S, accession number X56657), and *M. smegmatis* (GenBank entry GB:MS16S23S5, accession number Y08453). Preferred peptide nucleic acid probes should enclose at least one nucleobase complementary to a nucleobase of *M. tuberculosis* 5S rRNA within positions 86–90 of the alignment (indicated by heavy frame). Differences between the sequences of *M. bovis, M. phlei, M. leprae, M. smegmatis* and *M. luteus* and that of *M. tuberculosis* in the alignment are indicated by light frames.

Alignment for Mycobacteria other than those of the MTC group (23S rDNA)

FIGS. 4A–4L show alignments of 23S rDNA sequences of *M. avium* (GenBank entry GB:MA23SRNA, accession number X74494), *M. paratuberculosis* (GenBank entry GB:MPARRNA, accession number X74495), *M. tuberculosis* (GenBank entry GB:MTCY130, accession number Z73902). *M. phlei* (GenBank entry GB:MP23SRNA, accession number X74493), *M. leprae* (GenBank entry GB:ML5S23S, accession number X56657). *M. gastri* (GenBank entry GB:MG23SRRNA, accession number Z1721 1), *M. kansasii* (GenBank entry GB:MK23SRRNA, accession number Z17212), and *M. smegmatis* (GB:MS16S23S5, accession number Y08453). Preferred peptide nucleic acid probes should enclose at least one nucleobase complementary to a nucleobase of *M. avium* 23S rRNA within positions 99–101, 183, 261–271, 281–284, 290–293, 327–335, 343–357, 400–405, 453–462, 587–599, 637–660, 704–712, 763–789, 1060–1074, 1177–1185, 1259–1265, 1311–1327,1345–1348, 1361–1364, 1556–1570, 1608–1613, 1826–1638, 1651–1659, 1675–1677, 1734–1741, 1847–1853, 1967–1976, 2006–2010, 2025–2027, 2131–2232, 2252–2255, 2396–2405, 2416–2420, 2474–2478, 2687, 2719, 2809, 3062–3068, and 3097–3106 of the alignment (indicated by heavy frames). Differences between the sequences of *M. paratuberculosis, M. tuberculosis, M. phlei, M. leprae, M. gastri, M. kansasii*, and *M. smegmatis* and that of *M. avium* in the alignment are indicated by light frame.

Alignment for Mycobacteria other than those of the MTC group (16S rDNA)

FIGS. 5A–5B show alignments of 16S rDNA sequences of *M. avium* (GenBank entry GB:MSGRRDA, accession number M61673), *M. intracellulare* (GenBank entry GB:MIN16SRN, accession number X52927),*M. paratuberculosis* (GenBank entry GB:MSGRRDH, accession number M61680), *M. scrofulaceum* (GenBank entry GB: MSC16SRN, accession number X52924), *M. tuberculosis* (GenBank entry GB:MTU16SRN, accession number X52917), *M. bovis* (GenBank entry GB:MSGTGDA, accession number M20940), *M. leprae* (GenBank entry GB:MLEP16S1, accession number X55587), *M. kansasii* (GenBank entry GB:MKRRN16, accession number X15916), and *M. gastri* (GenBank entry GB:MGA16SRN, accession number X52919), *M gordonae* (GenBank entry GB:MSGRR16SI, accession number M29563), and *M. marinum* (GenBank entry GB:MMA16SRN, accession number X52920). Preferred peptide nucleic acid probes should enclose at least one nucleobase complementary to a nucleobase of *M. avium* 16S rRNA within positions 135–136, 472–475, 1136–1144, 1287–1292, 1313, and 1334 of the alignment (indicated by heavy frames). Differences between the sequences of *M. intracellulare, M. paratuberculosis, M. scrofulaceum, M. tuberculosis, M. bovis, M. leprae, M. kansasii*, and *M. gastri* and that of *M. avium* in the alignment are indicated by light frames.

Drug-resistance

FIG. 6 shows a partial *M. avium* 23S rDNA sequence including positions 2550 to 2589 of GenBank entry X74494. Bases in positions where deviations from the wild-type sequence have been correlated with macrollde-resistance are framed. Positions 2568 and 2569 in the figure correspond to positions 2058 and 2059, respectively, of *E.coli* 23S rRNA.

FIG. 7 shows a partial *M. tuberculosis* 16S rDNA sequence including positions 441 to 491 and 843 to 883 of GenBank entry X52917. Bases in positions where deviations from the wild-type sequence have been correlated with resistance to streptomycin are framed. Positions 452, 473, 474, 477, 865, and 866 in the figure correspond to positions 501, 522, 523, 526, 912, and 913, respectively, of *E.coli* 16S rRNA.

SPECIFIC DESCRIPTION

Mycobacteria are characterised by a complex cell wall which contains myolic acids, complex waxes and unique glycolipids. It is generally recognised by those skilled in the art that this wall provides mycobacteria with extreme resistance to chemical and physical stress as compared to other bacteria, and, accordingly, makes them very difficult to penetrate and lyse. The low permeability of the cell wall is considered to be the main reason for the fact that only very few drugs are effective in the treatment of tuberculosis and other mycobacterial infections. As described in U.S. Pat. No. 5,582,985, the wall appears further to prevent penetration by nucleic acid probes. Even with short probes (shorter than 30 nucleic acids), specific staining is low or often non-existent. Protocols that allow DNA probes to be used for in situ hybridisation to mycobacterial species are described in U.S. Pat. No. 5,582,985. However, these protocols require dewaxing of the mycobacterial cell wall with xylene and further enzymatic treatment prior to the hybridisation step in order to make the mycobacterial cell wall permeable to the DNA probes.

The problems set forth above have surprisingly been completely solved by the use of peptide nucleic acid probes. It has, surprisingly, been found that the peptide nucleic acid probes are able to penetrate the cell wall of the mycobacteria, and furthermore that this is taking place rapidly. The person skilled in the art would arrive at the conviction that it would be necessary to heavily treat the mycobacteria before hybridisation is carried out. Thus, based on the available prior art, there is a strong prejudice against carrying out hybridisation without prior destruction of the mycobacterial cell wall. The inventors have shown that this is indeed and unexpectedly possible. It has been demonstrated that the probes of the present invention are able to hybridise to mycobacterial precursor rRNA and rRNA without harsh treatment of the mycobacterial cells, thus avoiding a risk of interfering with the morphology of the cells. Using the present probes, specific and easy detection and, subsequently, diagnosis of tuberculosis and other mycobacterial infections are thus possible.

The present invention provides novel probes for use in rapid and specific, sensitive hybridisation based assays for detecting a target sequence of one or more mycobacteria, which target sequence is located in the mycobacterial rDNA, precursor rRNA, or in the 23S, 16S or 5S rRNA. The probes to be used in accordance with the present invention are peptide nucleic acid probes. Peptide nucleic acids are non-naturally occurring polyamides or polythioamides which can bind to nucleic acids (DNA and RNA). Such compounds are described in e.g. WO 92/20702.

We have identified suitable variable regions of the target nucleic acid by comparative analysis of generally available rDNA sequences and sequences obtained by sequencing as described above. Computers and computer programs, which have been used for the purposes disclosed herein, are commercially available. From such alignments, possibly suitable probes can be identified. The alignments are thus a useful guideline for designing probes with desired characteristics.

When designing the probes, due regard should be taken to the assay conditions under which the probes are to be used. Stringency is chosen so as to maximise the difference in stability between the hybrid formed with the target nucleic acid and that formed with the non-target nucleic acid. It will typically be necessary to choose high stringency conditions for probes where the specificity depends on only one mismatch to non-target sequences. The more mismatches to non-target sequences, the less demand for high stringency conditions.

Furthermore, probes should be designed so as to minimise the stability of probe-non-target nucleic acid hybrids. This may be accomplished by minimising the degree of complementarity to non-target nucleic acid, i.e. by designing the probe to span as many destabilising mismatches as possible, and/or to include as many additions/deletions relative to the target sequence as possible. Whether a probe is useful for detecting a particular mycobacterial species depends to some degree on the difference between the thermal stability of probe-target hybrids and probe:non-target hybrids. For rRNA targets, however, the secondary structure of the region of the rRNA molecule in which the target sequence is located may also be of importance. The secondary structure of a probe should also be taken into consideration. Probes should be designed so as to minimise their proclivity to form hairpins, self-dimers, and pair-dimers if a mixture of two or more probes is used.

Mismatching bases in hybrids formed between peptide nucleic acid probes and nucleic acids result in a higher thermal instability than mismatching bases in nucleic acid duplexes of the same sequences. Thus, the peptide nucleic acid probes exhibit a greater specificity for a given target nucleic acid sequence than a traditional nucleic acid probe, which is seen as a greater difference in $T_m$ values for probe-target hybrids and probe-non-target hybrids. The sensitivity and specificity of a peptide nucleic acid probe will also depend on the hybridisation conditions used.

The primary concern regarding the length of the peptide nucleic acid probes is the warranted specificity, i.e. which length provides sufficient specificity for a particular application. The optimal length of a peptide nucleic acid probe comprising a particular site with differences in base composition, e.g. among selected regions of mycobacterial rRNA, is a compromise between the general pattern that longer probes ensure specificity and shorter probes ensure that the destabilising differences in base composition constitute a greater portion of the probe. Also, due regard must be paid to the conditions under which the probes are to be used.

Peptide nucleic acid sequences are written from the N-terminal end of the sequence towards the C-terminal end. A free (unsubstituted) N-terminal end or an N-terminal end terminating with an amino acid is indicated as H, and a free C-terminal end is indicated as $NH_2$ (a carboxamide group). Peptide nucleic acids are capable of hybridising to nucleic acid sequences in two orientations, namely in antiparallel orientation and in parallel orientation. The peptide nucleic acid is said to hybridise in the antiparallel orientation when the N-terminal end of the peptide nucleic acid is facing the 3' end of the nucleic acid sequence, and to hybridise in the parallel orientation when the C-terminal end of the peptide nucleic acid is facing the 5' end of the nucleic acid sequence. In most applications, hybridisation in the antiparallel orientation is preferred as the hybridisation in the parallel orientation takes place rather slowly and as the formed duplexes are not as stable as the duplexes having antiparallel strands. Triplex formation with a stoichiometry of two peptide nucleic acid strands and one nucleic acid strand may occur if the peptide nucleic acid has a high pyrimidine content. Such triplexes are very stable, and probes capable of forming triplexes may thus be suitable for certain applications.

Mainly because the peptide nucleic acid strand is uncharged, a peptide nucleic acid-nucleic acid-duplex will have a higher $T_m$ than the corresponding nucleic acid-nucleic acid-duplex. Typically there will be an increase in $T_m$ of about 1° C. per base pair at 100 mM NaCl depending on the sequence (Egholm et al. (1993), Nature, 365, 566–568).

In contrast to DNA-DNA-duplex formation, no salt is necessary to facilitate and stabilise the formation of a peptide nucleic acid-DNA or a peptide nucleic acid-RNA duplex. The $T_m$ of the peptide nucleic acid-DNA-duplex changes only little with increasing ionic strength. Typically for a 15mer, the $T_m$ will drop only 5° C. when the salt concentration is raised from 10 mM NaCl to 1 M NaCl. At low ionic strength (e.g. 10 mM phosphate buffer with no salt added), hybridisation of a peptide nucleic acid to a target sequence is possible under conditions where no stable DNA-DNA-duplex formation occurs. Furthermore, target sites that normally are inaccessible can be made more readily accessible for hybridisation with peptide nucleic acid probes at low salt concentration as the secondary and tertiary structure of nucleic acids are destabilised under such conditions. Using peptide nucleic acid probes, a separate destabilising step or use of destabilising probes may not be necessary to perform.

The rRNAs are essential for proper function of the ribosomes and thus the synthesis of proteins. The genes encoding the rRNAs are in eubacteria located in an operon in which the small subunit RNA gene, the 16S rRNA gene, is located nearest the 5' end of the operon, the gene for the large subunit RNA, the 23S rRNA gene, is located distal to the 16S rRNA gene and the 5S rRNA gene is located nearest the 3' end of the operon. The three genes are separated by spacer regions in which rRNA genes may be found, however, there are none in *M. tuberculosis*. The primary transcript of the eubacterial rRNA operon is cleaved by RNaseIII. This cleavage results in separation of the 16S, the 23S and the 5S rRNA into precursor rRNA molecules (pre-rRNA molecules) which besides the rRNA species also contain leader and tail sequences. The primary RNase III cleavage is normally a rapid process, whereas the subsequent maturation is substantially slower. Precursor rRNA is typically more abundant than even strongly expressed mRNA species. Thus, for certain applications, precursor rRNA may be an attractive diagnostic target in order to specifically detect precursor rRNA, a target probe should be directed against sequences comprising at least part of the leader or tail sequences. A target probe may further be directed against sequences of which both part of the leader/tail and mature rRNA sequences are constituents.

Usually, patients having contracted a mycobacterial infection are treated with medicaments until no mycobacteria can be found in the sputum. Except for culturing, the presently available methods do not allow for clear distinguishing between living and dead mycobacteria. This means that a patient may often be treated with medicaments for a longer period of time than actually necessary. A way of determining the progress of treatment would be a very valuable tool in the fight of tuberculosis and other mycobacterial diseases.

As transcription and maturation of rRNA is a measure of viability, detection of precursor rRNA is a suitable and direct measure of viability of the bacteria. Furthermore, precursor rRNA may be used for identification of antibiotic drugs which reduce or inhibit rRNA transcription. One such example is rifampicin. A transcriptional inhibitor will in susceptible bacteria eliminate new synthesis of rRNA and thus the pool of precursor rRNA will be depleted. However, in resistant cells, primary transcripts as well as precursor rRNAs will continue to be produced.

Although it is preferred to use peptide nucleic acid probes targeting specific sequences of rRNA, it will readily be understood that peptide nucleic acid probes complementary to rRNA targeting probes will be useful for the detection of the genes coding for said sequence specific rRNA (rDNA), and peptide nucleic acid probes for the detecting rDNA is hence contemplated by the present invention. Although it is preferred to choose the sequence of the probe so as to enable the probe to hybridise to its target sequence in antiparallel orientation, it is to be understood that probes capable of hybridising in parallel orientation can be constructed from the same information. The present invention is intended to cover both types of probes.

In the broadest aspect, the present invention relates to peptide nucleic acid probes for detecting a target sequence of one or more mycobacteria optionally present in a test sample, said probe being capable of hybridising to a target sequence of mycobacterial rDNA, precursor rRNA or rRNA.

The probes of the invention may suitably be directed to rDNA, precursor rRNA, or to 23S, 16S or 5S rRNA.

The target sequences, to which the peptide nucleic acid probe(s) are capable of hybridising to, are obtainable by (a) comparing the nucleobase sequences of said mycobacterial rRNA or rDNA of one or more mycobacteria to be detected with the corresponding nucleobase sequence of organism(s), in particular other mycobacteria, in particular other mycobacteria, from which said one or more mycobacteria are to be distinguished, (b) selecting a target sequence of said rRNA or rDNA which includes at least one nucleobase differing from the corresponding nucleobase of the organisms in particular other mycobacteria, from which said one or more mycobacteria are to be distinguished, and (c) determining the capability of said probe to hybridise to the selected target sequence to form detectable hybrids.

Peptide nucleic acid probes are obtainable by (a) comparing the nucleobase sequences of said mycobacterial rRNA or rDNA of one or more mycobacteria to be detected with the corresponding nucleobase sequence of organism(s), in particular other mycobacteria, in particular other mycobacteria, from which said one or more mycobacteria are to be distinguished, (b) selecting a target sequence of said rRNA or rDNA which includes at least one nucleobase differing from the corresponding nucleobase of the organism(s), in particular other mycobacteria, from which said one or more mycobacteria are to be distinguished, (c) synthesising said probe, and (4) determining the capability of said probe to hybridise to the selected target sequence to form detectable hybrids.

The probes are in particular suitable for detecting a target sequence of one or more mycobacteria of the *Mycobacterium tuberculosis* Complex (MTC) or for detecting a target sequence of one or more mycobacteria other than mycobacteria of the *Mycobacterium tuberculosis* Complex (MOTT) optionally present in a sample, which probe comprises from 6 to 30 polymerised peptide nucleic acid moieties, said probe being capable of hybridising to a target sequence of mycobacterial rDNA, precursor rRNA or 23S, 16S or 5S rRNA forming detectable hybrids. Such probes may comprise peptide nucleic acid moieties of formula (I)

(I)

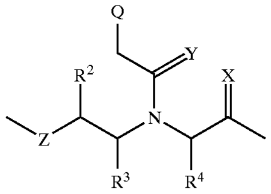

wherein each X and Y independents designate O or S, each Z independently designates O, S, $NR^1$, or $C(R^1)_2$, wherein each $R^1$ independently designate H, $C_{1-6}$ alkyl, $C_{1-6}$ alkenyl, $C_{1-6}$ alkynyl, each $R^2$, $R^3$ and $R^4$ designate independently H, the side chain of a naturally occurring amino acid, the side chain of a non-naturally occurring amino acid, $C_{1-4}$ alkyl, $C_{1-4}$ alkenyl or $C_{1-4}$ alkynyl, or a functional group, each Q independently designates a naturally occurring nucleobase, a non-naturally occurring nucleobase, an intercelator, a nucleobase-binding group, a label or H, with the proviso indicated above.

The probes nay suitably be used for detecting a species specific mycobacterial target sequence, or target sequences of a group of mycobacteria like MTC, MOTT, MAC or MAIS. The probes may further be designed so as to be capable of hybridising to one or more drug resistant mycobacteria, or, alternatively, to the wild-type corresponding thereto. In the design of the probes, sequences between different mycobacteria (one or more) may be taken into account as may sequences from other related or non-related organisms (one or more).

As mentioned above, drug-resistance is an increasing threat to the fight of mycobacterial infection. Monotherapy with macrolides such as clarithromycin and azithromycin often leads to clinically significant drug-resistance. Clarithromycin and azithromycin are important drugs in the treatment of infections by especially *M. avium*. Comparison between 23S rRNA sequences from isolates of *M. avium* and *M. intracellulare* with acquired resistance to clarithromycin and azithromycin and 23S rRNA sequences from non-resistant strains has revealed that the majority of resistant strains have single-point mutations in the 23S rRNA in positions corresponding to 2058 and 2059 in *E. coli* 23S rRNA. In the *M. avium* 23S rRNA sequence (GenBank accession number X74494), the corresponding bases are in position 2568 and 2569, respectively, as shown in FIG. 6. Most susceptible strains have an A residue in one of these positions whereas the resistant strains have a C, G or T in position 2058 (*E. coil* numbering corresponding to 2568 in *M. avium* with GenBank accession number X74494), or G or C in position 2059 (*E. coli* numbering corresponding to 2569 in *M. avium* with GenBank accession number X74494).

Single-point mutations in rRNA apparently also account to some degree for streptomycin resistance. Steptomycin, the first successful antibiotic drug against tuberculosis, is an aminocyclitol glycoside that perturbs protein synthesis at the ribosomal level. The genetic basis for streptomycin resistance has not yet been completely solved. However, some streptomycin resistant strains of *M. tuberculosis* have single-point mutations in 16S rRNA. These mutations are located in positions corresponding to bases 501, 522, 523, 526, 912 and 913 in *E. coli* 168 rRNA which correspond to bases with numbers 452, 473, 474, 477, 865 and 866, respectively, of *M. tuberculosis* 16S rRNA (GenBank accession number X52917) as shown in FIG. 7. Most of these mutated nucleotides are involved in structural interactions within the 530 loop of 16S rRNA which is one of the most conserved regions in the entire 16S rRNA gene.

Mutations in an 81 bp region of the gene (rpoB) encoding the beta subunit of RNA polymerase are the cause of 96% of the cases of rifampicin resistance in *M. tuberculosis* and *M. leprae*. rRNA precursor molecules have terminal domains (tails) which are removed during late steps In precursor rRNA processing to yield the mature rRNA molecules. Transcriptional inhibitors such as rifampicin can deplete precursor rRNA in sensitive cells by inhibiting de novo precursor rRNA synthesis while allowing maturation to proceed. Thus, precursor rRNA is depleted in susceptible mycobacterium cells while it remains produced in resistant mycobacterium cells when the cells are expose to rifampicin during culturing.

Peptide nucleic acid probes for detecting a target sequence of one or more mycobacteria of the *Mycobacterium tuberculosis* Complex are defined above. Peptide nucleic acid probes for detecting a target sequence of one or more mycobacteria other than mycobacteria of the *Mycobacterium tuberculosis* Complex are defined above. Peptide nucleic acid probes for detecting a target sequence of one or more drug resistant mycobacteria of the *Mycobacterium tuberculosis* complex or of one or more drug resistant mycobacteria other than mycobacteria of the *Mycobacterium tuberculosis* Complex are defined above.

In the present context and the claims, the term "naturally occurring nucleobases" includes the four main DNA bases (i.e. thymine (T), cytosine (C), adenine (A) and guanine (G)) as well as other naturally occurring nucleobases (e.g. uracil (U) and hypoxanthine).

The term "non-naturally occurring nucleobases" comprises i.a. modified naturally occurring nucleobases. Such non-naturally occurring nucleobases may be modified by substitution by e.g. one or more $C_{1-8}$ alkyl $C_{1-8}$ alkenyl or $C_{1-8}$ alkynyl groups or labels. Examples of non-naturally occurring nucleobases are purine, 2,6-diamino purine, 5-propynylcytosine (C propynyl), isocytosine (iso-C), 5-methyl-isocytosine (iso$^{Me}$C) (see e.g. Tetrahedron Letters Vol 36, No 12, 2033–2036 (1995) or Tetrahedron Letters Vol 36, No 21, 3601–3604 (1995)), 7-deazaadenine, 7-deazaguanine, $N^4$-ethanocytosine, $N^6$-ethano-2,6-diaminopurine, 5-($C_{3-6}$)-alkenyluracil, 5-($C_{3-6}$)-alkynylcytosine, 5-fluorouracil and pseudocytosine.

Examples of useful intercalators are e.g. acridin, antraquinone, psoralen and pyrene.

Examples of useful nucleobase-binding groups are e.g. groups containing cyclic or heterocyclic rings. Non-limiting examples are 3-nitro pyrrole and 5-nitro indole.

It is to be understood that alkyl, alkenyl and alkynyl groups may be branched or non-branched, cyclic or non-cyclic, and may further be interrupted by one or more heteroatoms, or may be unsubstituted or substituted by or may contain one or more functional groups. Non-limiting examples of such functional groups are acetyl groups, acyl groups, amino groups, carbamido groups, carbamoyl groups, carbamyl groups, carbonyl groups, carboxy groups, cyano groups, dithio groups, formyl groups, guanidino groups, halogens, hydrazino groups, hydrazo groups, hydroxamino groups, hydroxy groups, keto groups, mercapto groups, nitro groups, phospho groups, phosphono groups, phospho ester groups, sulfo groups, thiocyanato groups, cyclic, aromatic and heterocyclic groups.

$C_{1-4}$ groups contain from 1 to 4 carbon atoms, $C_{1-6}$ groups contain from 1 to 6 carbon atoms, and $C_{1-15}$ groups contain from 1 to 15 carbon atoms, not including optional substituents, heteroatoms and/or functional groups. Non-limiting examples of such groups are $—CH_3$, $—CF_3$, $—CH_2—$, $—CH_2CH_3$, $—CH_2CH_2—$, $—CH(CH_3)_2$, $—OCH_3$, $—OCH_2—$, $—OCH_2CH_3$, $—OCH_2CH_2—$, $—OCH(CH_3)_2$, $—OC(O)CH_3$, $—OC(O)CH_2—$, $—C(O)H$, $—C(O)—$, $—C(O)CH_3$, $—C(O)OH$, $—C(O)O—$, $—CH_2NH_2$, $—CH_2NH—$, $—CH_2OCH_3$, $—CH_2OCH_2—$, $—CH_2OC(O)OH$, $—CH_2OC(O)O—$, $—CH_2C(O)CH_3$, $—CH_2C(O)CH_2—$, $—C(O)NH_2$, $—CH{=}CH_2$, $—CH{=}CH—$, $—CH{=}CHCH_2C(O)OH$, $—CH{=}CHCH_2C(O)O—$, $—C{\equiv}CH$, $—C{\equiv}C—$, $—CH_2C{\equiv}CH$, $—CH_2C{\equiv}C—$, $—CH_2C{\equiv}CCH_3$, $—OCH_2C{\equiv}CH$, $—OCH_2C{\equiv}CH—$, $—OCH_2C{\equiv}CCH_3$, $—NHCH_2C(O)—$, $—NHCH_2CH_2C(O)—$, $—NH(CH_2CH_2O)_2CH_2C(O)—$, and $HO(O)CCH_2C(O)(NH—(CH_2CH_2O)_2CH_2C(O))_2—$, phenyl, benzyl, naphthyl, oxazolyl, pyridinyl, thiadiazolyl, triazolyl, and thienyl.

Within the present context, the expression "naturally occurring amino acid" is intended to comprise D- and L-forms of amino acids commonly found in nature, e.g. D- and L-forms of Ala (alanine), Arg (arginine), Asn (aspargine), Asp (aspartic acid), Cys (cysteine), Gln (glutamine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine) and Val (valine).

In the present context, the expression "non-naturally occurring amino add" is intended to comprise D- and L-forms of amino adds other than those commonly found in nature as well as modified naturally occurring amino acids. Examples of useful non-naturally occurring amino acids are D- and L-forms of βAla (β-alanine) Cha (cyclohexylalanine), Cit (citruline), Hcl (homocitrulline), HomoCys (homocystein), Hse (homoserine), Nle (norleucine), Nva (norvaline), Orn (ornithine), Sar (sarcosine) and Thi (thienylalanine).

In the present context the term "sample" is intended to cover all types of samples suitable for the purpose of the invention. Examples of such samples are sputum, laryngeal swabs, gastric lavage, bronchial washings, biopsies, aspirates, expectorates, body fluids (spinal, pleural, pericardial, synovial, blood, pus, bone marrow), urine, tissue sections as well as food samples, soil, air and water samples. Analysis of samples originating from the before-mentioned samples (e.g. cultures and treated samples) are also within the scope of the invention.

In the present context the term "hybrids" is intended to include complexes between a probe and a nucleic acid to be determined. Such hybrids may be made up of two or more strands.

The strength of the binding between the probe and the target nucleic acid sequence may be influenced by the ligand Q. When Q designates a nucleobase, Hoogsteen and/or Watson-Crick base pairing assist(s) in the formation of hybrids between a nucleic acid sequence to be detected and a probe. It is contemplated that one or more of the ligands may be a group which contribute little or none to the binding of the nucleic acid such as hydrogen. It is contemplated that suitable probes to be used comprise less than 25% by weight of peptide nucleic acid moieties, wherein Q designates such groups. One or more of the ligands Q may be groups that stabilise nucleobase stacking such as intercalators or nucleobase-binding groups.

In the above-indicated probes, one or more of the Q-groups may designate a label. Examples of suitable labels are given below. Moieties wherein Q denotes a label may preferably be located in one or both of the terminating moieties of the probe. Moieties wherein Q denotes a label may, however, also be located internally.

The peptide nucleic acid probes may comprise moieties, wherein all X groups are O (polyamides) or wherein all X groups are S (polythioamides). It is to be understood that the probes may also comprise mixed moieties (comprising both amide and thioamide moieties).

In another aspect, the present invention relates to peptide nucleic acid probes of formula (II), (III) and (IV) as well as mixtures of such probes defined above.

In a preferred embodiment, the peptide nucleic acid probes or mixtures thereof according to the invention are of formulas (I)–(IV) as defined above with Z being NH, $NCH_3$ or O, each $R^2$, $R^3$ and $R^4$ independently being H or the side chain of a naturally occurring amino acid, the side chain of a non-naturally occurring amino acid, or $C_{1-4}$ alkyl and each Q being a naturally occurring nucleobase or a non-naturally occurring nucleobase with the provisos defined above.

Peptide nucleic acid probes or mixtures of such probes according to the invention are preferably those of formula (I)–(IV) as defined above with Z being NH or O, and $R^2$ being H or the side chain of Ala, Asp, Cys, Glu, His, HomoCys, Lys, Orn, Ser or Thr, and Q being a nucleobase selected from thymine, adenine, cytosine, guanine, uracil, Iso-C, and 2,6-diaminopurine with the provisos defined above.

Peptide nucleic acid probes or mixtures thereof, which are of major interest for detecting mycobacteria of the MTC group or one or more mycobacteria other than mycobacteria of the MTC group, are probes of formula (V) as defined above, wherein $R^4$ is H or the side chain of Ala, Asp, Cys, Glu, His, HomoCys, Lys, Orn, Ser or Thr, Q is as defined above and with the provisos indicated above.

The peptide nucleic acid probe comprises polymerised moieties as defined above and in the claims. From the formula, it is to be understood that the probe may comprise polymerised moieties which structure may be mutually different or identical. In some cases, it may be advantageous that at least one moiety of the probe, preferably one (or both) of the moieties terminating the probe, are of a different structure. Such terminating moieties may suitably be a moiety of formula (VI)

(VI)

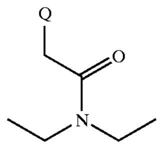

where Q is as defined above. Such moiety may suitably be connected to a peptide nucleic acid moiety through an amide bond.

The peptide nucleic acid probe according to the invention comprises from 6 to 30 polymerised moieties of formulas (I) to (IV), and, in addition, optionally one or two terminating moieties of formula (VI) as defined above. The preferred length of the probe will depend on the sample material and whether labeled probes are used. It is contemplated that especially interesting probes comprise from 10 to 30 polymerised moieties of formulas (I) to (V), and, in addition, optionally one or two terminating moieties of formula (VI) as defined above. Probes of the invention may suitably comprise from 12 to 25 polymerised moieties of formulas (I) to (V), more suitably from 14 to 22 polymerised moieties of formulas (I) to V, most suitably from 15 to 20 polymerised moieties of formulas (I) to (V), and, in addition, optionally one or two terminating moieties of formula (VI).

As mentioned above, the polymerised moieties of the probes may be mutually different or identical. In some embodiments, the polymerised moieties of formulas (V) constitute at least 75% by weight (calculated by excluding labels and linkers), preferably at least 80% by weight and most preferably at least 90% by weight of the probe.

The ends on the moieties terminating the probe may be substituted by suitable substituents which in the following will be named "linkers". A terminating end may suitably be substituted by from 1 to 5 linkers, more suitably from 1 to 3 linkers. Such linkers may suitably be selected among $C_{1-15}$ alkyl, $C_{1-15}$ alkenyl and $C_{1-15}$ alkynyl groups as defined above. The linkers may be substituted or unsubstituted, branched or non-branched, or be interrupted by heteroatoms, or be substituted or contain functional groups as described above. This may depend on the chemical nature of the terminating moiety (i.e. whether the moiety is terminated by a carbon, oxygen or nitrogen atom). A terminating end or a linker on a terminating end may further be substituted by one or more labels, which labels may be incorporated end to end, i.e. so as to form a non-branched labeled end, or may be incorporated so as to form a branched labelled end ("zipper"). The linkers may be attached directly to a terminating end, may be attached to a label or between labels on a terminating end, or be attached to a terminating end before a label is attached to a terminating end. It should be understood that two terminating ends may carry different or identical substituents, linkers and for labels. It should further be understood that the term "a label" is intended to comprise one or more labels as the term "linkers" is to comprise one or more linkers. For certain applications, it may be advantageous that one or more linkers are incorporated between the peptide nucleic acid moieties. Such applications may in particular be those based on triplex formation.

Examples of suitable linkers are $—NH(CH_2CH_2O)_n CH_2C(O)—$, $—NH(CHOH)_nC(O)—$, $—(O)C(CH_2OCH_2)_n C(O)—$ and $—NH(CH_2)_nC(O)—$, $NH_2(CH_2CH_2O)_nCH_2C(O)—$, $NH_2(CHOH)_nC(O)—$, $HO(O)C(CH_2OCH_2)_nC(O)—$, $NH_2(CH_2)_nC(O)—$, $—NH(CH_2CH_2O)_nCH_2C(O)OH$, $—NH(CHOH)_nC(O)OH$, $—(O)C(CH_2OCH_2)_nC(O)OH$ and $—NH(CH_2)_nC(O)OH$, wherein n is 0 or an integer from 1 to 8, preferably from 1 to 3. Examples of very interesting linkers are $—NHCH_2C(O)—$, $—NHCH_2CH_2C(O)—$,$—NH(CH_2CH_2O)_2CH_2C(O)—$, and $HO(O)CCH_2CH_2C(O)(NH(CH_2CH_2O)_2CH_2C(O))_2—$.

In the present context, the term "label" refers to a substituent which is useful for detection or visualisation. Suitable labels comprise fluorophores, biotin, dinitro benzoic acid, digoxigenin, radioisotope labels, peptide or enzyme labels, chemiluminiscence labels, fluorescent particles, hapten, antigen or antibody labels.

The expression "peptide label" is intended to mean a label comprising from 1 to 20 naturally occurring or non-naturally occurring amino acids, preferably from 1 to 10 naturally occurring or non-naturally occurring amino acids , more preferably from 1 to 8 naturally occurring or non-naturally occurring amino acids, most preferably from 1 to 4 naturally occurring or non-naturally occurring amino acids, linked together end to end in a non-branched or branched ("zipper") fashion. Such peptide label may be composed of amino acids which are mutually identical or different. In a preferred embodiment, such a non-branched or branched end comprises one or more, preferably from 1 to 8 labels, more preferably from 1 to 4, most preferably 1 or 2, further labels other than a peptide label. Such further labels may suitably terminate a non-branched end or a branched end. One or more linkers may suitably be attached to the terminating end before a peptide label and/or a further label is attached. Such linker units may also be attached between a peptide label and a further label. Furthermore, such peptide labels may be incorporated between the peptide nucleic acid moieties.

The probe as such may also comprise one or more labels such as from 1 to 8, preferably from 1 to 4, most preferably 1 or 2, labels and/or one or more linker units, which may be attached internally, i.e. to the backbone of the probe. The linker units and labels may mutually be attached as described above.

Examples of particular interesting labels are biotin, fluorescein labels, e.g. 5-(and 6)-carboxy-fluorescein, 5- or 6-carboxyfluorescein, 6-(fluorescein)-5-(and 6)-carboxamido hexanoic acid and fluorescein isothiocyanate, peptide labels consisting of from 1 to 20 naturally occurring amino acids or non-naturally occurring amino acids, enzyme labels such as peroxidases like horse radish peroxidase (HRP), alkaline phosphatase, and soya bean peroxidase, dinitro benzoic acid, rhodamine, tetramethylrhodamine, cyanine dyes such as Cy2, Cy3 and Cy5, coumarin, R-phycoerythrin (RPE), allophycoerythrin, Texas Red, Princeton Red, and Oregon Green as well as conjugates of R-phycoerythrin and, e.g. Cy5 or Texas Red.

Examples of preferred labels are biotin, fluorescent labels, peptide labels, enzyme labels and dinitro benzoic acid. Peptide labels may preferably be composed of from 1 to 10, more preferably of from 1 to 8, most preferably of from 1 to 4, naturally occurring or non-naturally occurring amino acids. It may be particularly advantageous to incorporate one or more other labels as well as a peptide label such as from 1 to 8 or from 1 to 4 other labels, preferably 1 or 2 other labels.

Suitable peptide labels may preferably be composed of cysteine, glycine, lysine or omithine.

In a further embodiment, the Q substituent as defined above may be labelled. Suitable labels are as defined above. Between Q and such a label, a linker as defined above may be incorporated. It is preferred that such labelled ligands Q are selected from thymine and uracil labelled in the 5-position and 7-deazaguanine and 7deazaadenine labelled in the 7-position.

A mixture of peptide nucleic acid probes is also part of the present invention. Such mixture may comprise more than one probe capable of hybridising to 23S rRNA, and/or more than one probe capable of hybridising to 16S rRRA, and/or or more than one probe capable of hybridising to 5S rRNA. A mixture of probes may further comprise probe(s) directed to precursor rRNA and/or rDNA. The mixture may also comprise peptide nucleic acids for detecting more than one mycobacteria in the same assay.

In a preferred embodiment the nucleobase sequence of the peptide nucleic acid probe is selected so as to be substantially complementary to the nucleobase sequence of the target sequence in question. In an especially preferred embodiment, the nucleobase sequence of the peptide nucleic acid probe is selected so as to be complementary to the nucleobase sequence of the target sequence in question. By "complementary" is meant that the nucleobases are selected so as to enable perfect match between the nucleobases of the probe and the nucleobases of the target, i.e. A to T or G to C. By substantially complementary is meant that the peptide nucleic acid probe is capable of hybridising to the target sequence, however, the probe does not necessarily have to be perfectly complementary to the target. For example, probes comprising one or more bases not complementary to the target sequence and non-target sequences, especially base(s) located at the end of the probe, where the effect on the stability of probe-target nucleic acid hybrids is low. Another example is probes comprising other naturally occurring bases. Thus provided that the probe is capable of hybridising to the target sequence, the nucleobase difference(s) between target sequences and non-target sequences ensures that the stability of probe-non-target nucleic acid hybrids are lower than the stability of probe-target nucleic acid hybrids and therefore make such substantially complementary probes applicable for detection of mycobacteria.

The probes may be synthesised according to the procedures described in "PNA Information Package" obtained from Millipore Corporation (Bedford, Mass., USA), or may be synthesised on an Expedite Nucleic Acid Synthesis System (PerSeptive BioSystems, USA).

If using the Fmoc strategy for elongation of the probe with linkers or amino acids, it is possible to retain side chain amino groups protected with acid sensitive protection groups such as the Boc or Mtt group. This method allows introduction of a linker containing several Boc protected amino groups which can all be cleaved and labelled in the same synthesis cycle.

One way of labelling a probe is to use a fluorescent label, such as 5-(and 6)-carboxyfluorescein, 5- or 6-carboxyfluorescein, or 6-(fluorescein)-5-(and 6)-carboxamido hexanoic acid. The acid group is activated with HATU (O-(7-azabenzotriazol-1-yl)-1,1,3,3-tetarmethyluronium hexafluorophosphate) or HBTU (2-(1H-benzotriazol-1-yl)-1,1,3,3-tetramethyluronium hexafluorophosphate) and reacted with the N-terminal amino group of the peptide nucleic acid. The same technique can be applied to other labelling groups containing an acid function.

Alternatively, the succinimidyl ester of the above-mentioned labels may suitably be used or fluorescein isothiocyanate may be used directly.

After synthesis, probes can be cleaved from the resin using standard procedures as described by Millipore Corporation or PerSeptive BioSystems. The probes are subsequently purified and analysed using reversed phase HPLC techniques at 50° C. and were characterised by matrix-assisted laser desorption/ionisation time of flight mass spectrometry (MALDI-TOFMS), plasma desorption mass spedrometry (PDMS), electron spray mass spectometry (ESMS), or fast atom bombardment (FAB-MS).

Generally, probes such as probes comprising polymerised moieties of formula (IV) and (V) may also be prepared as described in, e.g., Angewandte Chemie, International Edition In English 35, 1939–1942 (1996) and Bioorganic & Medical Chemistry Letters, Vol 4, No 8, 1077–1080 (i994). Chemical properties of some probes are described in, e.g., Nature, 365, 566–568 (1993).

The method as claimed can be used for the detection of a target sequence of one or more mycobacteria optionally present in a sample. The method and the probes provide a valuable tool for analysing samples for the presence of such target sequences, hence providing information for establishing a diagnosis.

In the assay method according to the invention, the sample to be analysed for the presence of mycobacteria is brought into contact with one or more probes or a mixture of such probes according to the invention under conditions by which hybridisation between the probe(s) and any sample rRNA or rDNA originating from mycobacteria can occur, and the formed hybrids, if any, are observed or measured, and the observation or measurement is related to the presence of a target sequence of one or more mycobacteria. The observation or measurement may be accomplished visually or by means of instrumentation.

Prior to contact with probe(s) according to the invention, the samples may undergo various types of sample processing which include purification, decontamination and/or concentration. The sample may suitably be decontaminated by treatment with sodium hypochlorite and subsequently centrifuged for concentration of the mycobacteria. Samples e.g. sputum samples may be treated with a mucolytic agent such as N-Acetyl-L-cystein which reduces the viscosity of the sample as well as be treated with sodium hydroxide which decontaminates the sample, and subsequently centrifuged. Other well-known decontamination and concentration procedures include the Zephiran-trisodium phosphate method, Petroff's sodium hydroxide method, the oxalic acid method as well as the cetylpyridinium chloride-sodium chloride method. Samples may also be purified and concentrated by applying sample preparation methods such as filtration, immunocapture, two-phase separation either alone or in combination. The sample preparation methods may also be used together with the centrifugation and decontamination methods mentioned above.

Samples may, either directly or after having undergone one or more processing steps, be analysed in primarily two major types of assays, in situ-based assays and in vitro-based assays. In this context, in situ-based assays are to be understood as assays, in which the target nucleic acids remain within the bacterial cell during the hybridisation process. Examples to are in situ hybridisation (ISH) assays on smears and biopsies as well as hybridisation to whole cells which may be in suspension and which subsequently may be analysed by e.g. flow cytometry optionally after capture of the bacteria onto particles (with same or different type and size), or by image analysis after spreading of the bacteria onto a solid medium, filter membrane or another substantially planar surface.

In vitro-based assays are to be understood as assays, in which the target nucleic acids are released from the bacterial cell before hybridisation. Examples of such assays are microtiter plate-based assays. Many other assay types, in which the released target nucleic acids by some means are captured onto a solid phase and subsequently analysed via a detector probe, are feasible and within the scope of the present invention. Even further, in vitro-based assays include assays, in which the target nucleic acids are not captured onto a solid phase, but in which the hybridisation and signal generation take place entirely in solution.

Samples for in situ-based assays may suitably be applied and optionally be immobilised to a support. Techniques for applying of a sample onto a solid support depend on the type of sample in question and include smearing and cytocentrifugation for liquid or liquified samples and sectioning of tissues for biopsy materials. The solid support may take a wide variety of forms well-known in the art, such as a microscope slide, a filter membrane, a polymer membrane or a plate of various materials.

In the case of in vitro-based assays, the target nucleic acid may be released from the mycobacterial cells in various ways. Most methods for releasing the nucleic acids cause bursting of the cell wall (lysis) followed by extraction of the nucleic acids into a buffered solution. As mycobacteria have complex cell walls containing covalently associated peptidoglycans, arabinogalactans and in particular mycolic acids, they cannot easily be disrupted by standard methods used for the rapid lysis of other bacteria. Possible methods which are known to give successful lysis of the mycobacterial cell wall include methods which involve treatment with organic solvents, treatment with strong chaotropic reagents such as high concentrations of guanidine thiocyanate, enzyme treatment, bead beating, heat treatment, sonication and/or application of a French press.

Samples to be analysed by in situ assays may be fixed prior to hybridisation. The person skilled in the art will readily recognise that the appropriate procedure will depend on the type of sample to be examined. Fixation and/or immobilisation should preferably preserve the morphological integrity of the cellular matrix and of the nucleic acids. Examples of methods for fixation are flame fixation, heat fixation, chemical fixation and freezing. Flame fixation may be accomplished by passing the slide through the blue cone of a Bunsen burner 3 or 4 times; heat fixation may be accomplished by heating the sample to 80° C. for 2 hours; chemical fixation may be accomplished by immersion of the sample in a fixative (e.g. formamide, methanol or ethanol). Freezing is particularly relevant for biopsies and tissue sections and is usually carried out in liquid nitrogen.

In one in situ hybridisation assay embodiment, the sample to be analysed is smeared onto a substantially planar solid support which may be a microscope slide, a filter membrane, a polymer membrane or another type of solid support with a planar surface. The preferred solid support is a microscope slide. After the smear has been prepared, it may optionally undergo further pre-treatment like treatment with bactericidal agents or additional fixation by immersion in e.g. ethanol. The sample may also be pretreated with enzyme(s) which as primary function permeabilise the cells and or reduce the viscosity of the sample. It may further be advantageous to perform a pre-hybridisation step in order to block sites which might otherwise give raise to non-specific binding. For this purpose, blocking agents like skim milk, and non-target probes may suitably be used. The components of the pre-hybridisation mixture should be selected so as to obtain an effective saturation of sites in the sample that might otherwise bind the probe non-specifically. The pre-hybridisation buffer may suitably comprise an appropriate buffer, blocking agent(s), and detergents.

During the in situ hybridisation, one or more probes according to the present invention are brought into contact with any target rRNA or rDNA inside the cells in a hybridisation solution under suitable stringency conditions. The concentration of the applied probe may vary depending on the chemical nature of the probe and the conditions under which hybridisation is carried out. Typically a probe concentration between 1 nM and 1 $\mu$M is suitable. The hybridisation solution may comprise a denaturing agent which allows hybridisation to take place at a lower temperature than would be the case without the agent. The denaturing agent should be present in an amount effective to increase the ratio between specific binding and non-specific binding.

The effective amount of denaturing agent depends on the type used and on the probe or combination of probes. Examples of denaturing agents are formamide, ethylene glycol and glycerol, and these may preferably be used in a concentration above 10% and less than 70%. The preferred denaturing agent is formamide which is used more preferably in concentrations from 20% to 60%, most preferably from 30% to 50%. It should be noted that in several instances it may not be necessary or advantageous to include a denaturing agent.

Prior to hybridisation or during hybridisation, a mixture of random probes (probes with random, non-selected sequences of optionally different length) ray be added in excess to reduce non-specific binding. Also, one or more non-sense probes (probes with a defined nucleobase sequence and length differing from the nucleobase sequence of the target sequence) may be added in excess in order to reduce non-specific binding. Also, non-specific binding of detectable probes to one or more non-target nucleic acid sequences can be suppressed by addition of one or more unlabelled or independently detectable probes, which probes have a sequence that is complementary to the non-target sequence(s). It is particularly advantageous to add such blocking probes when the non-target sequence differs from the target sequence by only one mismatch.

It may be advantageous to include inert polymers which are believed to increase the effective concentration of the probe(s) in the hybridisation solution. One such macromolecule is dextran sulphate which may be used in concentrations of from 2.5% to 15%. The preferred concentration range is from 8% to 12%. In the case of dextran sulphate. Other useful macromolecules are polyvinylpyrrolidone and ficoll, which typically are used at lower concentrations, e.g. 0.2%. It may further be advantageous to add one or more detergents which may reduce the degree of non-specific binding of the peptide nucleic acid probes. Examples of useful detergents are sodium dodecyl sulphate. Tween 20® or Triton X-100®. Detergents are usually used in concentrations between 0.05% and 1.0%, preferably between 0.05% and 0.25%. The hybridisation solution may furthermore contain salt. Although it is not necessary to include salt in order to obtain proper hybridisation, it may be advantageous to include salt in concentrations from 2 to 500 mM, or suitably from 5 to 100 mM.

During hybridisation, other important parameters are hybridisation temperature, concentration of the probe and hybridisation time. The person skilled in the art will readily recognise that optimal conditions must be determined for each of the above-mentioned parameters according to the specific situation, e.g. choice of probe(s) and type and concentration of the components of the hybridisation buffer, in particular the concentration of denaturing agent. Presence of volume excluders may also have an effect.

Following hybridisation, the sample is washed to remove any unbound and any non-specifically bound probe, and consequently, appropriate stringency conditions should be used. By stringency is meant the degree to which the reaction conditions favour the dissociation of the formed hybrids. The stringency may be increased typically by increasing the washing temperature and/or washing time. Typically, washing times from 5 to 40 minutes may be sufficient. Two or more washing periods of shorter time may also give good results. A range of buffers may be used, including biological buffers, phosphate buffers and standard citrate buffers. The demand for low salt concentration in the buffers is not as pertinent as for DNA probe assays due to the difference response to salt concentration. In some cases, it is advantageous to increase the pH of the washing buffer as it may give an increased signal-to noise ratio (see WO 97/18325). This is conceivably due to a significant reduction of the non-specific binding. Thus, it may be advantageous to use a washing solution with a pH value form 8 to 10.5, preferably from 9 to 10.

Visualisation of bound probe(s) must be carried out with due regard to the type of label chosen. There are a wide range of useful probe labels, in particular various fluorescent labels such as fluorescein, rhodamine and derivatives thereof. Furthermore, labels like enzymes (e.g. peroxidases and phosphatases) and haptens (e.g. biotin, digoxigenin, dinitro benzoic acid) may suitably be applied. In the case of fluorescent labels, the hybrids formed may be visualised using a microscope with a magnification of at least ×250, preferably ×1000. The visualisation may further be carried out using a CCD (charge coupled device) camera optionally controlled by a computer. When haptens are used as labels, the hybrids may be detected using an antibody conjugated with an enzyme. In these cases, the detection step may be based on colorimetry fluorescence or luminescence.

The probes may alternatively be labelled with fluorescent particles having the fluorescent label embedded in the particles (e.g. Estapor K coulored microspheres), located on the surface of the particles and/or coupled to the surfaces of the particles. As the particles have to come into contact with the target nucleic acids within the cells, the use of fluorescent particles may necessitate pretreatment of the bacteria. Relatively small particles e.g. about 20 nm may suitable be used.

In another in situ hybridisation embodiment, frozen tissue or biopsy samples are cut into thin sections and transferred to a substantially planar surface, preferably microscope slides. Prior to hybridisation, the tissue or biopsy may be treated with a fixative, preferably a precipitating fixative such as acetone, or the sample is incubated in a solution of buffered formaldehyde. Alternatively, the biopsy or tissue section can be transferred to a fixative such as buffered formaldehyde for 12 to 24 hours and following fixation, the tissue may be embedded in paraffin forming a block from which thin sections can be cut. Prior to hybridisation, the tissue section is dewaxed and rehydrated using standard procedures. Permeabilisation (e.g. treatment with proteases, diluted acids, detergents, alcohol and/or heat) may in some cases be advantageous. The selected method for permeabilisation depends on several factors, for instance on the fixative used, the extent of fixation, the type and size of sample, and on the applied probe. For these types of samples, sample processing, prehybridisation, hybridisation, washing and visualisation may be carried out using same or adjusted conditions as described above.

In a further embodiment of the in situ assays, the bacterial cells are kept in suspension during fixation, prehybridisation, hybridisation and washing are carried out under the same or similar conditions as described above. The preferred type of label for this embodiment is fluorescent labels. This allows detection of hybridised cells by flow cytometry, recording the intensity of fluorescence per cell. Bacterial cells in suspension may further be coupled to particles, preferably with a size of from 20 nm to 10 $\mu$m. The particles may be made of materials well-known in the art like latex, dextran, cellulose and/or agarose, and may optionally be paramagnetic or contain a fluorescent label. Normally, bacterial cells are coupled to particles using antibodies against the target bacteria, but other means like molecular imprinting may also be used. Coupling of the bacterial cells to particles may be advantageous in sample handling and/or during detection.

In the embodiments of in situ hybridisation described above, the probes according to the invention are used for detecting a target sequence of one or more mycobacteria. In a preferred embodiment, the probes are suitable for detecting a target sequence of mycobacteria of the *Mycobacterium tuberculosis* Complex (MTC), mycobacteria other than the *Mycobacterium tuberculosis* Complex (MOTT), or mycobacteria of the *Mycobacterium avium* Complex (MAC). The probes are further suitable for detecting simultaneously different target sequences originating from the same mycobacteria.

Samples to be analysed using in vitro-based assays need to undergo a treatment by which the nucleic acids are released from the bacterial cells. Nucleic acids may be released using organic solvents, strong chaotropic reagents such as high concentrations of guanidine thiocyanate, enzymes, bead beating, heating, sonication and/or application of a French press. The obtained nucleic acids may undergo additional purification prior to hybridisation.

In one in vitro hybridisation embodiment, the sample comprising the target nucleic acid is added to a container comprising immobilised capture probe(s) and one or more probe(s) labelled to function as detector probe(s). The hybridisation should be performed under suitable stringency conditions. The hybridisation solution may further comprise a denaturing agent blocking probes, inert polymers, detergents and salt as described for the in situ-type assays. Likewise, the hybridisation temperature, probe concentration and hybridisation time are important parameters that need to be controlled according to the specific conditions of the assay, e.g. choice of peptide nucleic acid probe(s) and concentration of some of the ingredients of the hybridisation buffer. If hybridisation of the target nucleic acid to the capture probe(s) and detector probe(s), respectively, is performed in two separate steps, different parameters, in particular different stringency conditions, may be used in these steps. The concentration of the capture probe may be higher for in situ assays as hybridisation may be controlled better and washing can be performed more efficiently.

The capture probes may be immobilised onto a solid support by any means, e.g. by a coupling reaction between a carboxylic acid on a linker and an amino derivatised support. The capture probe may further be coupled onto the solid support by photochemical activation of photoreactive groups which have been attached absorptively to the solid support prior to photochemical activation. Such photoreactive groups are described in the U.S. Pat. No. 5,316,784 A. The capture probes may further be coupled to a hapten which allows an affinity based immobilisation to the solid support. One such example is coupling of a biotin to the probe(s) and immobilisation via binding to a steptavidin-coated surface.

The solid support may take a wide variety of forms well-known in the art, such as a microtiter plate having one or more wells, a filter membrane, a polymer membrane, a tube, a dip stick, a strip and particles. Filter membranes may be made of cellulose, celluloseacetate, polyvinylidene fluoride or any other materials well-known in the art. The polymer membranes may be of polystyrene, nylon, polypropylene or any other materials well known in the art. Particles may be paramagnetic beads, beads made of polystyrene, polypropylene, polyethylene, dextran, nylon, amyloses, celluloses, polacrylamides and agarose. When the solid support has the form of a filter, a membrane, a strip or beads, it (they) may be incorporated into a single-use device.

The selection of the label of the detector probe(s) depend on the specific assay format and possible instrumentation. When biotin labelled probes are used, the hybrids may be detected using streptavidin or an antibody against the biotin label which antibody or streptavidin may be conjugated with an enzyme and the actual detection depend on the choice of the specific enzyme, preferably a phosphatase or a peroxidase, and the substrate for the selected enzyme. The signal may in some cases be enhanced using commercially available amplification systems such as the catalysed signal amplification system for biotinylated probes (CSA by DAKO). Various polymer-based enhancement systems may also be used. An example is a dextran polymer to which both a hapten specific antibody and an enzyme is coupled. The detector probe(s) may further be labelled with other haptens. e.g. digoxigenin, dinitro benzoic acid and fluorescein, in which case the hybrids may be detected using an antibody against the hapten which antibody may be conjugated with an enzyme. It is even possible to apply detector probe(s) which have enzymes coupled directly onto the probes. There are a wide range of possibilities for selection of enzyme substrates allowing for colourimetric (substrates e.g. p-nitrophenyl phosphate or tetra-methyl-benzidine), fluorogenic (substrates e.g. 4methylumbilliferylphosphate) or chemiluminescent (substrates e.g. 1,2-dioxetanes) detection.

The detector probes may further be labelled with various fluorescent labels, preferably fluorescein or rhodamine, in which case the hybrids may be detected by measuring the fluorescence.

The detector probe(s) will typically be different from the capture probe(s), thus ensuring dual species specificity. The dual specificity will most often allow at least one of the probes to be shorter, e.g. a 10 mer probe.

Furthermore, the capture of purine rich sequences may be improved by utilising bis-peptide nucleic acids as capture probes. Such bis-peptide nucleic acids are described in WO 96/02558. The bis-peptide nucleic acids comprise a first peptide nucleic acid strand capable of hybridising in parallel fashion to the target nucleic acid, and a second peptide nucleic acid strand capable of hybridising in antiparallel fashion to the purine rich sequence of the nucleic acid to be captured. The two peptide nucleic acid strands are connected by a linker and are in this way capable of forming a triplex structure with said purine rich sequence nucleic acid. The number of polymerised moieties of each linker-separated peptide nucleic add may be as previously defined for non-bis-peptide nucleic acids. However, due to the high stability of the triplexes formed, bis-peptide nucleic acids with short first and second strands can be used making the design of a pyrimidine rich probe easier.

Instead of using a detector probe, capture probe: nucleic acid complexes may be detected using a detection system based on an antibody reacting specifically with complexes formed between peptide nucleic acids and nucleic acids (such as described in WO 95/17430), in which detection system the primary antibody may comprise a label, or which detection system comprises a labelled secondary antibody, which specifically binds to the primary antibody. The specific detection again depends on the selected substrate which may be of any type of those mentioned above.

Depending on the type of specific assay format label and detection principle various types of instrumentation may be used including conventional microplate readers, luminometers and flow cytometers. Adaptation of adequate instrumentation may allow for automatisation of the assay.

In an example of this embodiment, a capture probe of the present invention is coupled to a microtiter plate by a photochemical reaction between antraquinon-labelled capture probe and polystyrene of the microwell. Target rRNA is added to the microwells and incubated under stringent conditions. Unbound rRNA is removed by washing and the microwell are incubated with a hapten-labelled detector probe under stringent conditions. The visualisation is carried out using an enzyme-labelled antibody against the hapten, which after removal of unbound antibody is detected using a chemiluminescence substrate.

In another example of this embodiment capture probes are coupled to latex particles, and hybridisation is carried out under suitable conditions in the presence of e.g. fluorescein labelled detector probe(s). After hybridisation and optionally washing, the hybrids are detected by flow cytometry. A range of different beads (e.g. by size or colours) may carry different capture probes for different targets, thus allowing a multiple detection system.

In a further embodiment of the in vitro assays format, the capture probe, the target nucleic acid and the detector probe may hybridise in solution, and subsequently the capture probe is attached to a solid phase. The solid phase, the hybridisation conditions and means of detection may be selected according to the specific method as described above.

In a further embodiment of in vitro assays, the target nucleic acid may be immobilised onto filter or polymer membranes or other types of solid phases well-known in the art. The hybridisation conditions and means of detection may be selected according to the specific set-up as described above.

In a further embodiment of the in vitro assay, an array of up to 100 or even more different probes directed against different target sequences may be immobilised onto a solid surface and hybridisation of the target sequences to all the probes is carried out simultaneously. The solid phase, the hybridisation conditions and means of detection may be as described above. This allow for simultaneous detection or identification of a range of parameters, i.e. species identification and resistance patterns.

The present probes further provide a method of diagnosing infection by mycobacteria and a method for determining the stage of the infection and the appropriate treatment by which methods one or more optionally labelled probes according to the invention are brought into contact with a patient sample and the type of treatment and/or the effect of a treatment is (are) evaluated.

Kits comprising at least one peptide nucleic acid probe as defined herein are also part of the present invention. Such kit may further comprise a detection system with at least one detecting reagent and/or a solid phase capture system.

DESCRIPTION OF SPECIFIC EMBODIMENTS

Examples of suitable Qs of adjacent moieties are given below. Peptide nucleic add probes comprising such Qs will be suitable for detecting mycobacteria, in particular mycobacteria of the MTC group or mycobacteria other than mycobacteria of the MTC group. The probes are written from left to right corresponding to from the N-terminal end towards the C-terminal end. Suitable Q subsequences for detecting 23S and 16S rRNA as well as 5S rRNA of the MTC group are given below. Suitable a subsequences for detecting 23S and 16S rRNA of mycobacteria other than mycobacteria of the MTC group are further given below. The Q subsequences include at least one nucleobase complementary to a nucleobase selected from the positions given in parenthesis. The Q subsequences are given as non-limiting examples of construction of suitable probe nucleobase sequences. It is to be understood that the probes may comprise fewer or more peptide nucleic acid moieties than indicated.

| | |
|---|---|
| MTC group (23S) | |
| AGA TGC GGG TAG CAC (selected from positions 149–158 in FIG. 1A), | (Seq ID no 1) |
| TGT TTT CTC CTC CTA (selected from positions 220–221 in FIG. 1A), | (Seq ID no 2) |
| ACT GCC TCT CAG CCG (selected from positions 328–361 in FIG. 1A and FIG. 1B), | (Seq ID no 3) |
| TGA TAC TAG GCA GGT (selected from positions 453–455 in FIG. 1B), | (Seq ID no 4) |
| CGG ATT CAC AGC GGA (selected from positions 490–501 in FIG. 1B), | (Seq ID no 5) |
| TCA CCA CCC TCC TCC (selected from positions 637–660 in FIG. 1C), | (Seq ID no 6) |
| CCA CCC TCC TCC (selected from positions 637–660 in FIG. 1C) | (modified Seq ID no 6) |
| TTA ACC TTG CGA CAT (selected from positions 706–712 in FIG. 1D), | (Seq ID no 7) |
| ACT ATT CAC ACG CGC (selected from positions 762–789 in FIG. 1D), | (Seq ID no 8) |
| CTC CGC GGT GAA CCA (selected from position 989 in FIG. 1D), | (Seq ID no 9) |
| GCT TTA CAC CAC GGC (selected from positions 1068–1072 in FIG. 1E), | (Seq ID no 10) |
| ACG CTT GGG GGC CTT (selected from position 1148 in FIG. 1E), | (Seq ID no 11) |
| CCA CAC CCA CCA CAA (selected from positions 1311–1329 in FIG. 1E), | (Seq ID no 12) |
| CCG GTG GCT TCG CTG (selected from positions 1361–1364 in FIG. 1F), | (Seq ID no 13) |
| ACT TGC CTT GTC GCT (selected from position 1418 in FIG. 1F), | (Seq ID no 14) |
| GAT TCG TCA CGG GCG (selected from positions 1563–1570 in FIG. 1F), | (Seq ID no 15) |
| AAC TCC ACA CCC CCG (selected from positions 1627–1638 in FIG. 1G), | (Seq ID no 16) |
| ACT CCA CAC CCC CGA (selected from positions 1627–1638 in FIG. 1G), | (Seq ID no 17) |
| ACC CCT TCG CTT GAC (selected from positions 1675–1677 in FIG. 1G), | (Seq ID no 18) |
| CTT GCC CCA GTG TTA (selected from position 1718 in FIG. 1G), | (Seq ID no 19) |
| CTC TCC CTA CCG GCT (selected from positions 1734–1740 in FIG. 1H), | (Seq ID no 20) |
| GAT ATT CCG GTC CCC (selected from positions 1967–1976 in FIG. 1H), | (Seq ID no 21) |
| ACT CCG CCC CAA CTG (selected from positions 2403–2420 in FIG. 1H), | (Seq ID no 22) |
| CTG TCC CTA AAC CCG (selected from positions 2457–2488 in FIG. 1I), | (Seq ID no 23) |
| TTC GAG GTT AGA TGC (selected from positions 2457–2488 in, FIG. 1I), | (Seq ID no 24) |
| GTC CCT AAA CCC GAT (selected from positions 2457–2488 in FIG. 1I), | (Seq ID no 25) |
| GGT GCA CCA GAG GTT (selected from positions 2952–2956 in FIG. 1I), | (Seq ID no 26) |
| CTG GCG GGA CAA CTG (selected from positions 2966–2969 in FIG. 1J), | (Seq ID no 27) |
| TTA TCC TGA CCG AAC (selected from positions 3000–3003 in FIG. 1J), | (Seq ID no 28) |
| GAC CTA TTG AAC CCG (selected from positions 3097–3106 in FIG. 1J), | (Seq ID no 29) |
| MTC group (16S) | |
| GAA GAG ACC TTT CCG (selected from positions 76–79 in FIG. 2A), | (Seq ID no 30) |
| CAC TCG AGT ATC TCC (selected from positions 98–101 in FIG. 2A), | (Seq ID no 31) |
| ATC ACC CAC GTG TTA (selected from positions 136–136 in FIG. 2A), | (Seq ID no 32) |
| GCA TCC CGT GGT CCT (selected from positions 194–201 in FIG. 2B), | (Seq ID no 33) |
| CAC AAG ACA TGC ATC (selected from positions 194–201 in FIG. 2B), | (Seq ID no 34) |
| TAA AGC GCT TTC CAC (selected from positions 222–229 in FIG. 2B), | (Seq ID no 35) |
| GCT CAT CCC ACA CCG (selected from position 242 in FIG. 2B), | (Seq ID no 36) |

-continued

| | |
|---|---|
| CCG AGA GAA CCC GGA (selected from position 474 in FIG. 2C), | (Seq ID no 37) |
| AGT CCC CAC CAT TAC (selected from positions 1136–1145 in FIG. 2C), | (Seq ID no 38) |
| AAC CTC GCG GCA TCG (selected from positions 1271–1272 in FIG. 2C), | (Seq ID no 39) |
| GGC TTT TAA GGA TTC (selected from positions 1287–1292 in FIG. 2D), | (Seq ID no 40) |
| GAC CCC GAT CCG AAC (selected from position 1313 in FIG. 2D), | (Seq ID no 41) |
| CCG ACT TCA CGG GGT (selected from position 1334 in FIG. 2D), | (Seq ID no 42) |
| MTC group (5S) | |
| CGG AGG GGC AGT ATC (selected from positions 86–90 in FIG. 3), | (Seq ID no 43) |
| Mycobacteria other than those of the MTC group (23S) | |
| GAT CAA TGC TCG GTT (selected from positions 99–101 in FIG. 4A), | (Seq ID no 44) |
| TTC CCC GCG TTA CCT (selected from position 183 in FIG. 4A), | (Seq ID no 45) |
| TTA GCC TGT TCC GGT (selected from positions 261–271 in FIG. 4A), | (Seq ID no 46) |
| GCA TGC GGT TTA GCC (selected from positions 281–284 in FIG. 4B), | (Seq ID no 47) |
| TAC CCG GTT GTC CAT (selected from positions 290–293 in FIG. 4B), | (Seq ID no 48) |
| GTA GAG CTG AGA CAT (selected from positions 327–335 and 343–357 in FIG. 4B), | (Seq ID no 49) |
| GCC GTC CCA GGC CAC (selected from positions 400–405 in FIG. 4B and FIG. 4C), | (Seq ID no 50) |
| CTC GGG TGT TGA TAT (selected from positions 453–462 in FIG. 4C), | (Seq ID no 51) |
| ACT ATT TCA CTC CCT (selected from positions 587–599 in FIG. 4C), | (Seq ID no 52) |
| ACG CCA TCA CCC CAC (selected from positions 637–660 in FIG. 4D), | (Seq ID no 53) |
| CGA CGT GTC CCT GAC (selected from positions 704–712 in FIG. 4D), | (Seq ID no 54) |
| ACT ACA CCC CAA AGG (selected from positions 763–789 in FIG. 4E), | (Seq ID no 55) |
| CAC GCT TTT ACA CCA (selected from positions 1060–1074 in FIG. 4E), | (Seq ID no 56) |
| GCG ACT ACA CAT CCT (selected from positions 1177–1185 in FIG. 4E), | (Seq ID no 57) |
| CGG CGC ATA ATC ACT (selected from positions 1259–1265 in FIG. 4E), | (Seq ID no 58) |
| CCA CAT CCA CCG TAA (selected from positions 1311–1327 in FIG. 4F), | (Seq ID no 59) |
| CGC TGA ATG GGG GAC (selected from positions 1345–1348 in FIG. 4F), | (Seq ID no 60) |
| GGA GCT TCG CTG AAT (selected from positions 1361–1364 in FIG. 4G), | (Seq ID no 61) |
| CGG TCA CCC GGA GCT (selected from positions 1361–1364 in FIG. 4G), | (Seq ID no 62) |
| GGA CGC CCA TAC ACG (selected from positions 1556–1570 in FIG. 4G), | (Seq ID no 63) |
| GAA GGG GAA TGG TCG (selected from positions 1608–1613 in FIG. 4H), | (Seq ID no 64) |
| AAT CGC CAC GCC CCC (selected from positions 1626–1638 in FIG. 4H), | (Seq ID no 65) |
| CAG CGA AGG TCC CAC (selected from positions 1651–1659 in FIG. 4H), | (Seq ID no 66) |
| GTC ACC CCA TTG CTT (selected from positions 1675–1677 in FIG. 4H), | (Seq ID no 67) |
| ATC GCT CTC TAC GGG (selected from positions 1734–1741 in FIG. 4H), | (Seq ID no 68) |
| GTG TAT GTG CTC GCT (selected from positions 1847–1853 in FIG. 4I), | (Seq ID no 69) |
| ACG GTA TTC CGG GCC (selected from positions 1967–1976 in FIG. 4I), | (Seq ID no 70) |
| GGC CGA ATC CCG CTC (selected from positions 2006–2010 in FIG. 4I), | (Seq ID no 71) |
| AAA CAG TCG CTA CCC (selected from positions 2025–2027 in FIG. 4I), | (Seq ID no 72) |
| CCT TAC GGG TTA ACG (selected from positions 2131–2132 in FIG. 4J), | (Seq ID no 73) |

-continued

| | |
|---|---|
| GAG ACA GTT GGG AAG (selected from positions 2252–2255 in FIG. 4J), | (Seq ID no 74) |
| TGG CGT CTG TGC TTC (selected from positions 2396–2405 in FIG. 4J and FIG. 4K), | (Seq ID no 75) |
| CGA CTC CAC ACA AAC (selected from positions 2416–2420 in FIG. 4K), | (Seq ID no 76) |
| GAT AAG GGT TCG ACG (selected from positions 2474–2478 in FIG. 4K), | (Seq ID no 77) |
| ATC CGT TGA GTG ACA (selected from position 2687 in FIG. 4K), | (Seq ID no 78) |
| CAG CCC GTT ATC CCC (selected from position 2719 in FIG. 4K), | (Seq ID no 79) |
| AAC CTT TGG GAC CTG (selected from position 2809 in FIG. 4L), | (Seq ID no 80) |
| TAA AAG GGT GAG AAA (selected from positions 3062–3068 in FIG. 4L), | (Seq ID no 81) |
| GTC TGG CCT ATC AAT (selected from positions 3097–3106 in FIG. 4L), | (Seq ID no 82) |
| Mycobacteria other then those of the MTC group (16S) | |
| AGA TTG CCC ACG TGT (selected from positions 135–136 in FIG. 5A), | (Seq ID no 83) |
| AAT CCG AGA AAA CCC (selected from positions 472–475 in FIG. 5A), | (Seq ID no 84) |
| GCA TTA CCC GCT GGC (selected from positions 1136–1144 in FIG. 5A), | (Seq ID no 85) |
| TTA AAA GGA TTC GCT (selected from positions 1287–1292 in FIG. 5B), | (Seq ID no 86) |
| AGA CCC CAA TCC GAA (selected from position 1313 in FIG. 5B), | (Seq ID no 87) |
| GAC TCC GAC TTC ATG (selected from position 1334 in FIG. 5B), | (Seq ID no 88) |
| Drug resistance | |
| 23S-mediated macrolide resistance (*M. avium*) | |
| GTC TTT TCG TCC TGC (wild-type) (selected from positions 2568–2569 in FIG. 6), | (Seq ID no 89) |
| GTC TTA TCG TCC TGC (selected from positions 2568 in FIG. 6), | (Seq ID no 90) |
| GTC TTC TCG TCC TGC (selected from positions 2568 in FIG. 6), | (Seq ID no 91) |
| GTC TTG TCG TCC TGC (selected from positions 2568 in FIG. 6), | (Seq ID no 92) |
| GTC TAT TCG TCC TGC (selected from positions 2568 in FIG. 6), | (Seq ID no 93) |
| GTC TCT TCG TCC TGC (selected from positions 2568 in FIG. 6), | (Seq ID no 94) |
| GTC TGT TCG TCC TGC (selected from positions 2568 in FIG. 6), | (Seq ID no 95) |
| 16S-mediated streptomycin resistance (*M. tuberculosis*) | |
| TTG GCC GGT GCT TCT (wild-type) (selected from positions 452 in FIG. 7), | (Seq ID no 96) |
| TTG GCC GGT ACT TCT (selected from positions 452 in FIG. 7), | (Seq ID no 97) |
| TTG GCC GGT CCT TCT (selected from positions 452 in FIG. 7), | (Seq ID no 98) |
| TTG GCC GGT TCT TCT (selected from positions 452 in FIG. 7), | (Seq ID no 99) |
| ACC GCG GCT GCT GGC (wild-type) (selected from positions 473–477 in FIG. 7), | (Seq ID no 100) |
| ACC GCG GCT ACT GGC (selected from positions 473 in FIG. 7), | (Seq ID no 101) |
| ACC GCG GCT CCT GGC (selected from positions 473 in FIG. 7), or | (Seq ID no 102) |
| ACC GCG GCT TCT GGC (selected from positions 473 in FIG. 7), | (Seq ID no 103) |
| CGG CAG CTG GCA CGT (selected from positions 474 in FIG. 7), | (Seq ID no 104) |
| CGG CCG CTG GCA CGT (selected from positions 474 in FIG. 7), | (Seq ID no 105) |
| CGG CTG CTG GCA CGT (selected from positions 474 in FIG. 7), | (Seq ID no 106) |
| CGT ATT ACC GCA GCT (selected from positions 477 in FIG. 7), | (Seq ID no 107) |
| CGT ATT ACC GCC GCT (selected from positions 477 in FIG. 7), | (Seq ID no 108) |

-continued

| | |
|---|---|
| CGT ATT ACC GCT GCT (selected from positions 477 in FIG. 7), | (Seq ID no 109) |
| TTC CTT TGA GTT TTA (wild-type) (selected from positions 865–866 in FIG. 7), | (Seq ID no 110) |
| TTC CTT TAA GTT TTA (selected from positions 865 in FIG. 7), | (Seq ID no 111) |
| TTC CTT TCA GTT TTA (selected from positions 865 in FIG. 7), | (Seq ID no 112) |
| TTC CTT TTA GTT TTA (selected from positions 865 in FIG. 7), | (Seq ID no 113) |
| TTC CTT AGA GTT TTA (selected from positions 866 in FIG. 7), | (Seq ID no 114) |
| TTC CTT CGA GTT TTA (selected from positions 866 in FIG. 7), | (Seq ID no 115) |
| TTC CTT GGA GTT TTA (selected from positions 866 in FIG. 7), | (Seq ID no 116) |

Other examples of suitable subsequences are given below.

| | |
|---|---|
| CAT GTG TCC TGT GGT and | (Seq ID no 117) |
| CGT CAG CCC GAG AAA | (Seq ID no 118) |

selected so as to be complementary to *M. gordonae* 16S rRNA (positions 174–188 and 452–466, respectively, of GenBank entry GB:MSGRR16SI, accession no. M29563). These positions correspond to positions 192–206 and 473–487, respectively, of the alignments shown in FIGS. 2 and 5. Probes having this or a similar nucleobase sequence are suitable for detecting *M. gordonae.*

| | |
|---|---|
| CAC TAC ACA CGC TCG, and | (Seq ID no 119) |
| TGG CGT TGA GGT TTC | (Seq ID no 120) |

selected so as to be complementary to positions 781–795 and 2369–2383, respectively, of *M. kansasli* 235 rRNA (GenBank entry MK23SRRNA accession number Z17212). These positions correspond to positions 774–794 and 2398–2412, respectively, of the alignments shown in FIGS. 1 and 4. Probes having this or a similar nucleobase sequence are suitable for detecting *M. kansasii.*

| Precursor rRNA | |
|---|---|
| AAC ACT CCC TTT GGA | (Seq ID no 123) |

A peptide nucleic add probe having the above-indicated nucleobase sequence is directed to *M. tuberculosis* precursor rRNA. The probe is complementary to positions 602 to 616 of GenBank accession number X58890.

Especially, probes based on those nucleobase sequences with sequence identification numbers Seq ID no 62, 79 and 80 (and other probes selected from positions 1361–1364 in FIG. 1F, 2719 in FIG. 4K and 2809 in FIG. 4L) are suitable for detecting *M. avium.* Probes based on the nucleobase sequence with sequence identification number Seq ID no 55 (and other probes selected from positions 763–789 in FIG. 4E) are suitable for detecting *M. avium, M. intracellulare* and *M. scrofulaceum* as a group (the organisms termed the MAIS group of mycobacteria). In addition, probes based on the nucleobase sequences with sequence identification numbers Seq ID no 77 and 81 are suitable for detecting *M. avium, M. intracellulare* and *M. paratuberculosis* as a group.

The invention is further illustrated by the non-limiting examples given below.

EXAMPLES

Example 1

Mycobacterium species (*M. bovis* and *M. intacellulare*) 23S rDNA were partly amplified by PCR, and the PCR products were sequenced (both strands) using Cy5-labelled oligonucleotide primers (DNA Technology, Aarhus, Denmark) and the 7deaza-dGTP Thermo Sequenase cycle sequencing kit from Amersham, Little Chalfont, England. Sequences were read using an ALFexpress automated sequencer and ALFwin (version 1.10) software from Pharmacia Biotech, Uppsala, Sweden. *M. bovis* and *M. intracellulare* 23S rRNA sequences are included at the following positions of the 23S rDNA sequence alignments: positions 681–729 (FIGS. 1C and 4D), positions 761–800 (FIGS. 1D and 4E), positions 2401–2440 (FIGS. 1H and 4K), positions 2441–2480 (FIGS. 1I and 4K), positions 2481–2520 (FIG. 1I), positions 3041–3080 (FIG. 4L), and positions 3081–3120 (FIGS. 1J and 4L).

Example 2

Sequence alignments (see FIGS. 1 to 5) of 23S,16S and 5S rDNA of mycobacteria of the MTC group, and 23S and 16S rDNA of mycobacteria other than those of the MTC group (MOTT) were done using the Megalign (version 3.12) alignment tool from DNASTAR (Madison, Wis. USA). Up to one hundred sequences were aligned at a time.

Peptide nucleic acid probes in which the nucleobase sequence was complementary to distinctive mycobacterial rRNA were designed with due regard to secondary structures using the PrimerSelect program (version 3.04) from DNASTAR. As a control of sequence specificity, all probe sequences were subsequently matched with the GenBank and EMBL databases using BLAST sequence similarity searching at the National Center for Biotechnology Information (http:/www.ncbi.nim.nih.gov).

As examples, the following sequences were selected:

| | |
|---|---|
| MTC 23S | |
| TCA CCA CCC TCC TCC | (Seq ID no 6) |
| CCA CCC TCC TCC | (modified Seq ID no 6) |
| ACT ATT CAC ACG CGC | (Seq ID no 8) |
| CCA CAC CCA CCA CAA | (Seq ID no 12) |
| AAC TCC ACA CCC CCG | (Seq ID no 16) |
| ACT CCA CAC CCC CGA | (Seq ID no 17) |
| ACT CCG CCC CAA CTG | (Seq ID no 22) |
| CTG TCC CTA AAC CCG | (Seq ID no 23) |
| TTC GAG GTT AGA TGC | (Seq ID no 24) |
| GTC CCT AAA CCC GAT | (Seq ID no 25) |
| GAC CTA TTG AAC CCG | (Seq ID no 29) |
| MTC 16S | |
| GCA TCC CGT GGT CCT | (Seq ID no 33) |
| CAC AAG ACA TGC ATC | (Seq ID no 34) |
| GGC TTT TAA GGA TTC | (Seq ID no 40) |
| MOTT 23S | |
| GAT CAA TGC TCG GTT | (Seq ID no 44) |
| CGA CTC CAC ACA AAC | (Seq ID no 76) |
| MOTT 16S | |
| GCA TTA CCC GCT GGC | (Seq ID no 85) |
| Drug resistance | |
| GTC TTA TCG TCC TGC | (Seq ID no 90) |
| GTC TTC TCG TCC TGC | (Seq ID no 91) |
| GTC TTG TCG TCC TGC | (Seq ID no 92) |
| GTC TAT TCG TCC TGC | (Seq ID no 93) |
| GTC TCT TCG TCC TGC | (Seq ID no 94) |
| GTC TGT TCG TCC TGC | (Seq ID no 95) |

-continued

| Precursor rRNA | |
|---|---|
| AAC ACT CCC TTT GGA | (Seq ID no 123) |
| Non-sense probes | |
| GTC CGT GAA CCC GAT | (Seq ID no 121) |
| TAC GCT CTT TGA GCT | (Seq ID no 122) |

Example 3

Peptide nucleic acid probes were synthesised using an Expedite 8909 Nucleic Acid Synthesis System purchased from PerSeptive Biosystems (Framingham, USA). The peptide nucleic acid probes were terminated with two β-alanine molecules or with one or two lysine molecule(s) and, before cleavage from the resin, labelled with 5-(or 6)-carboxyfluorescein (Flu) or rhodamine (Rho) at the β-amino group of alanine (peptide label) or ε-amino group of lysine (peptide label), respectively. Probes were purified using reverse phase HPLC at 50° C. and characterised using a G2025 A MALDI-TOF MS instrument (Hewlett Packard, San Fernando, Calif., USA). Molecular weights determined were within 0.1% of the calculated molecular weights.

The following labelled peptide nucleic acid probes were synthesised:

| MTC 23S | |
|---|---|
| Lys(Flu)-Lys(Flu)-TCA CCA CCC TCG TCC-$NH_2$ | (OK 446/ modified Seq ID no 6) |
| Lys(Flu)-Lys(Flu)-CCA CCC TCC TCC-$NH_2$ | (OK 575/ modified Seq ID no 6) |
| Lys(Flu)-Lys(Flu)-ACT ATT CAC ACG CGC-$NH_2$ | (OK 447/ modified Seq ID no 8) |
| Lys(Flu)-ACT ATT CAC ACG CGC-$NH_2$ | (OK 688/ modified Seq ID no 8) |
| Lys(Flu)-Lys(Flu)-CCA CAC CCA CCA CAA-$NH_2$ | (OK 448/ modified Seq ID no 12) |
| Lys(Flu)-Lys(Flu)-AAC TCC ACA CCC CCG-$NH_2$ | (OK 449/ modified Seq ID no 16) |
| Lys(Flu)-Lys(Flu)-ACT CCA CAC CCC CGA-$NH_2$ | (OK 309/ modified Seq ID no 17) |
| Lys(Flu)-Lys(Flu)-ACT CCG CCC CAA CTG-$NH_2$ | (OK 450/ modified Seq ID no 22) |
| Lys(Flu)-Lys(Flu)-CTG TCC CTA AAC CCG-$NH_2$ | (OK 305/ modified Seq ID no 23) |
| Lys(Flu)-Lys(Flu)-TTC GAG GTT AGA TGC-$NH_2$ | (OK 306/ modified Seq ID no 24) |
| Lys(Flu)-TTC GAG GTT AGA TGC-$NH_2$ | (OK 682/ modified Seq ID no 24) |
| Lys-(Flu)-Lys(Flu)-GTC CCT AAA CCC GAT-$NH_2$ | (OK 307/ modified Seq ID no 25) |
| Lys(Flu)-GTC CCT AAA CCG GAT-$NH_2$ | (OK 654/ modified Seq ID no 25) |
| Lys(Flu)-GAC CTA TTG AAC CCG-$NH_2$ | (OK 660/ modified Seq ID no 29) |

-continued

| MTC 16S | |
|---|---|
| Lys(Flu)-Lys(Flu)-Gly-GCA TCC CGT GGT CCT-$NH_2$ | (OK 223/ modified Seq ID no 33) |
| Lys(Flu)-Lys(Flu)-CAC AAG AGA TGC ATC-$NH_2$ | (OK 310/ modified Seq ID no 34) |
| Lys(Flu)-CAC AAG ACA TGC ATC-$NH_2$ | (OK 655/ modified Seq ID no 34) |
| Lys(Flu)-GGC TTT TAA GGA TTC-$NH_2$ | (OK 689/ modified Seq ID no 40) |
| Lys(Rho)-GGC TTT TAA GGA TTC-$NH_2$ | (OK 702/ modified Seq ID no 40) |
| MOTT 23S | |
| Flu-β-Ala-β-Ala-GAT CAA TGC TCG GTT-$NH_2$ | (OK 624/ modified Seq ID no 44) |
| Flu-β-Ala-β-Ala-CGA CTC CAC ACA AAC-$NH_2$ | (OK 612/ modified Seq ID no 76) |
| MOTT 16S | |
| Flu-β-Ala-β-Ala-GCA TTA CCC GCT GGC-$NH_2$ | (OK 623/ modified Seq ID no 85) |
| Drug resistance | |
| Lys(Flu)-GTC TTT TCG TCC TGC-$NH_2$ | (OK 745/ modified Seq ID no 89) |
| Lys(Rho)-GTC TTA TCG TCC TGC-$NH_2$ | (OK 746/ modified Seq ID no 90) |
| Lys(Rho)-GTC TTC TCG TCC TGC-$NH_2$ | (OK 746/ modified Seq ID no 91) |
| Lys(Rho)-GTC TTG TCG TCC TGC-$NH_2$ | (OK 746/ modified Seq ID no 92) |
| Lys(Rho)-GTC TAT TCG TCC TGC-$NH_2$ | (OK 747/ modified Seq ID no 93) |
| Lys(Rho)-GTC TCT TCG TCC TGC-$NH_2$ | (OK 747/ modified Seq ID no 94) |
| Lys(Rho)-GTC TGT TCG TCC TGC-$NH_2$ | (OK 747/ modified Seq ID no 95) |
| Precursor rRNA | |
| Lys(Flu)-AAC ACT CCC TTT GGA-$NH_2$ | (OK 749/ modified Seq ID no 123) |
| Reduction of non-specific binding | |
| GTC CGT GAA CCC GAT-$NH_2$ | (OK 507/ modified Seq ID no 121) |
| Gly-TAC GCT CTT TGA GCT-$NH_2$ | (OK 714/ modified Seq ID no 122) |

Example 4

Initially the ability of the peptide nucleic acid probes to react with target sequences of mycobacterial rRNA was tested by dot blot carried out with rRNA from *M. bovis* BCG, *M. avium* and *E.coli.*

*M. bovis* BCG (Statens Serum Institut, Denmark) and *M. intracellulare* (kindly provided by Statens Serum Institut) were grown in Dubos broth (Statens Serum Institut) or on L öwenstein-Jensen slants (Statens Serum Institut) at 37° C.

RNA was isolated from the bacterial cells using TRI-reagent (Sigma) following manufacture's directions. *E. coli* rRNA was purchased from Boehringer Mannheim, Germany.

200 ng *M. bovis* RNA. *M. intracellulare* RNA and *E. coli* rRNA were dotted onto membranes (Schleicher & Schüel, NY 13 N), and the membranes were dried and fixed under UV light for 2 minutes.

Protocol for dot blot assay

Each of the probes (70 nM probe in hybridisation solution (50 mM Tris, 10 mM NaCl, 10% (w/v) Dextran sulphate, 50% (v/v) glycerol, 5 mM EDTA, 0.1% (w/v) sodium pyrophosphate, 0.2% (w/v) polyvinylpyrrolidone, 0.2% (w/v) Ficoll, pH 7.6.)) were spotted onto a membrane. Hybridisation was continued for 1.5 hours at 55 or 65° C., respectively. The membranes were rinsed 2 times for 15 minutes in 2×SSPE buffer (1×SSPE: 0.15 M NaCl, 10 mM sodium phosphate, 1 mM EDTA, pH 7.4) containing 0.1% SDS at ambient temperature, and subsequently 2 times for 15 minutes in 0.1×SSPE buffer containing 0.1% SDS at 55 or 65 ° C. (see Table 1). The membrane was blocked with 0.5% (w/v) casein dissolved in 0.5M NaCl, 0.05M Tris/HCl pH 9.0. Thereafter, the membranes were incubated for 1 hour with rabbit-anti FITC antibody labelled with alkaline phosphatase (AP) (DAKO K0046 vial A) diluted 1:2000 in 0.5% casein dissolved in 0.5M NaCl, 0.05M Tris/HCl pH 9.0. After incubation, the membranes were washed 3 times 5 minutes with TST buffer (0.05M Tris, 0.5M NaCl, 0.5% (w/v) Tween 20®, pH 9) at ambient temperature. Bound probes were visualised following standard procedures using BCIP/NBT, and the visualisation was stopped by incubation for 10 minutes with 10 mM EDTA. The blot was dried at 50° C.

The results are given in Table 1 below.

TABLE 1

| | *E. coli* rRNA | | *M. bovis* BCG RNA | | *M. intracellulare* RNA | |
|---|---|---|---|---|---|---|
| Probe | 55° C. | 65° C. | 55° C. | 65° C. | 55° C. | 65° C. |
| OK 305 | negative | negative | positive | positive | negative | weak |
| OK 307 | negative | negative | positive | positive | negative | weak |
| OK 309 | negative | negative | positive | positive | negative | weak |
| OK 223 | negative | negative | positive | positive | nd | nd |
| OK 310 | negative | negative | negative | positive | negative | negative |

nd: Not determined

The results indicate that all five peptide nucleic acid probes are capable of hybridising to target sequence of *M. bovis* BCG rRNA (as a representative of the MTC group), whereas no hybridisation to *E coli* rRNA (as a representative of organisms other than mycobacteria) and no detectable hybridisation to *M. intracellulare* rRNA were observed (as a representative of the MOTT group).

Example 5

This example illustrates the ability of the peptide nucleic acid probes to penetrate the mycobacterial cell wall and subsequently hybridise to target sequence of mycobacteria of the MTC group and not mycobacteria of the MOTT group, in particular not mycobacteria of the MAC group, or *Neisseria gonorrhoeae,* by fluorescence in situ hybridisation (FISH).

Preparation of bacterial slides

*M. bovis* BCG (Statens Seruminstitut, Denmark), *M. avium* (kindly provided by Statens Seruminstitut, Denmark), and *M. intracellulare* (kindly provided by Statens Seruminstitut, Denmark) were grown in Dubos broth (Statens Seruminstitut, Denmark) or on Löwenstein-Jensen slants (Statens Seruminstitut, Denmark) at 37° C. *N. gonorrhoeae* (Statens Seruminstitut, Denmark) was grown on chocolate agar (Statens Seruminstitut, Denmark) at 37° C. with additional 5% $CO_2$.

Cultures were smeared onto microscope slides and fixed according to standard procedures. Prior to the hybridisation, the smears were immersed into 80% ethanol for 15 minutes, and subsequently rinsed with water and air dried. This step is not essential for the following hybridisation step, but it is anticipated that it will kill any viable mycobacteria on the slides, and may further serve as an additional fixation step.

Protocol for fluorescence in situ hybridisation (FISH)

1. The bacterial slide was covered with a hybridisation solution containing the probe in question.
2. The slide was incubated in a humid incubation chamber at 45° C. or 55° C. for 90 minutes.
3. The slide was washed 25 minutes at 45° C. or 55° C. in prewarned wash solution (5 mM Tris, 145 mM NaCl, pH 10) followed by 30 seconds in water.
4. The slide was dried and mounted with IMAGEN Mounting Fluid (DAKO, Copenhagen, Denmark)

The hybridisation solution contains 50 mM Tris, 10 mM NaCl, 10% (w/v) Dextran sulphate, 30% (v/v) formamide, 0.1% (v/v) Triton X-100®, 5 mM EDTA, 0.1% (w/v) sodium pyrophosphate, 0.2% (w/v) polyvinylpyrrolidone, 0.2% (w/v) Ficoll, pH 7.6.

Whenever possible, the applied equipment was heat-treated, and solutions were exposed to 1 μl/ml diethylpyrocarbonate (Sigma Chemical Co.) in order to inactivate nucleases.

Microscopically examinations were conducted using a fluorescence microscope (Leica, Wetzlar, Germany) equipped with a 100×/1.20 water objective, a HBO 100 W lamp and a FITC filter set. Mycobacteria were identified as fluorescent, 1–10 μm slender, rod-shaped bacilli.

Fluorescein-labelled peptide nucleic acid probes targeting 23S rRNA of the mycobacteria of the MTC group (OK 306, OK 309, OK 446, OK 449) and 16S rRNA of the mycobacteria of the MTC group (OK 310) were tested. Individual probe concentrations and incubation temperatures are listed together with the results in Table 2 and 3.

TABLE 2

| | OK 306 250 nM 45° C. | OK 309 250 nM 45° C. | OK 446 500 nM 55° C. | OK 449 500 nM 55° C. |
|---|---|---|---|---|
| *M. bovis* BCG | positive | positive | positive | positive |
| *M. avium* | negative | negative | negative | negative |
| *M. intracellulare* | negative | negative | not determined | not determined |
| *N. gonorrhoeae* | negative | negative | not determined | not determined |

TABLE 3

| | OK 447 1 μM 55° C. | OK 310 250 nM 45° C. | OK 306/OK 310 500/500 nM 55° C. |
|---|---|---|---|
| *M. bovis* BCG | positive | positive | positive |
| *M. avium* | negative | negative | negative |
| *M. intracellulare* | not determined | negative | negative |
| *N. gonorrhoeae* | not determined | negative | not determined |

It can be concluded that the probes are able to penetrate the mycobacterial cell wall of mycobacterium cultures and subsequently hybridise to target rRNA sequence. This makes possible the development of fluorescence in situ hybridisation (FISH) protocols for specific detection of mycobacteria.

Example 6

Test of probes on clinical smears of sputum

The ability of the peptide nucleic acid to penetrate the cell wall of mycobacteria of the MTC group in clinical samples was tested on smears of sputum from suspected cases of tuberculosis (kindly provided by Division of Microbiology, Ramathibodi Hospital, Bangkok, Thailand) by fluorescence in situ hybridisation (FISH). Smears from the same patient were initially evaluated positive by Ziehl-Neelsen staining, which shows only the presence of acid fast bacilli, not whether these are mycobacteria of the MTC group.

Fluorescein-labelled peptide nucleic acid probes targeting 23S rRNA of the mycobacteria of the MTC group (OK 306, OK 446, OK 449) and 16S rRNA of the mycobacteria of the MTC group (OK 310) were used. Furthermore, a random peptide nucleic acid probe (a 15-mer wherein each position may be A, T, C or G (obtained from Millipore Corporation, Bedford, Mass., USA) was added to the hybridisation solution in order to increase the signal-to-noise ratio. FISH was carried out at 55° C. as described in Example 5. Applied probe concentrations are listed together with the results in Table 4 and 5.

TABLE 4

| Sample number | OK 446/Random 1 $\mu$M/50 $\mu$M | OK 449/Random 1 $\mu$M/50 $\mu$M | Ziehl-Neelsen staining |
|---|---|---|---|
| 285 | Positive | Positive | 4+ |
| 335 | Positive | Eq. | 2+ |
| 345 | Positive | Positive | 3+ |
| 224 | Positive | Positive | 3+ |
| 297 | Negative | Eq. | 2+ |
| 179 | Negative | Negative | 4+ |
| 247 | Negative | Negative | 2+ |
| 255 | Positive | Positive | 2+ |
| 202 | Eq. | Positive | 2+ |

TABLE 5

| Sample number | OK 306/OK 310 500/500 nM | Ziehl-Neelsen staining |
|---|---|---|
| 213 | Positive | 4+ |
| 292 | Positive | 4+ |
| 159 | Positive | 3+ |
| 287 | Positive | 3+ |

Smears stained by Ziehl-Neelsen staining were examined with a 100× objective and scored according to the following method;–: 0 bacilli, +/–: 1–200 per 300 fields, 2+: 1–9 per 10 fields, 3+: 1–9 per field, 4+:>9 per field.

Positive: Several mycobacteria were identified in the smear. Negative: No fluorescent mycobacteria were identified in the smear. Eq: Few (1–3) fluorescent mycobacteria were identified in the smear.

It appears from the table that the peptide nucleic acid probes are able to penetrate and subsequently hybridise to target sequence of mycobacteria of the MTCgroup in AFB-positive sputum smears. The act that not all AFB-positive sputum smears are found positive with applied probes indicate that not all AFB-positive sputum smears contains mycobacteria of the MTC-group.

Example 7

The reactivity and specificity of selected peptide nucleic acid probes for detecting mycobacteria of the MTC group as well as probes for detecting mycobacteria of the MOTT group were evaluated by fluorescence in situ hybridisation (FISH) on control smears prepared from cultures of different mycobacterium species. The mycobacterium species were selected so as to be representative for the mycobacterium genus as well as to include clinically relevant species.

*M. tuberculosis* (ATCC 25177), *M. bovis* BCG (ATCC 35734), *M. intacellulare* (ATCC 13950), *M. avium* (ATCC 25292), *M. kansasii* (ATCC12479), *M. gordonae* (ATCC 14470), *M. scrofulaceum* (ATCC 19981), *M. abscessus* (ATCC19977), *M. marinum* (ATCC 927), *M. simiae* (ATCC 25575), *M. szulgai* (ATCC 35799), *M. flavescens* (ATCC 23033), *M. fortuitum* (ATCC 43266) and *M. xenopi* (ATCC19250) were grown at Dubos broth (Statens Serum Institut) at 37° C. with the exception of *M. marinum* which was grown at 32° C.

Smears were prepared as described in Example 5. FISH was carried out as described below.

Protocol for fluorescence in situ hybridisation (FISH)

1. The bacterial slide was covered with a hybridisation solution containing the probe in question.
2. The slide was incubated in a humid incubation chamber at 55° C. for 90 minutes.
3. The slide was washed 30 minutes at 55° C. in pre-warmed wash solution (5 mM Tris, 15 mM NaCl, 0.1% (w/v), Triton X-100®, pH 10) followed by 30 seconds in water.
4. The slide was dried and mounted with IMAGEN Mounting Fluid (DAKO, Copenhagen, Denmark)

The hybridisation solution contained 50 mM Tris, 10 mM NaCl, 10% (w/v) Dextran sulphate, 30% (v/v) formamide, 0.1% (v/v) Triton X-100®, 5 mM EDTA, 0.1% (w/v) sodium pyrophosphate, 0.2% (w/v) polyvinylpyrrolidone, and 0.2% (w/v) Ficoll, pH 7.6. To avoid non-specific binding of the labelled peptide nucleic acid probe, 1–5 $\mu$M of non-labelled, non-sense peptide nucleic acid probe (OK 507/modified Seq ID no 121 and/or OK 714/modified Seq ID no 122) was added to the hybridisation solution.

Whenever possible, the applied equipment was heat-treated, and solutions were exposed to 1 $\mu$/ml diethylpyrocarbonate (Sigma Chemical Co.) in order to inactivate nucleases.

Microscopic examinations were conducted using a fluorescence microscope (Leica, Wetzlar, Germany) equipped with a 100×/1.30 oil objective, a HBO 100 W lamp and a FITC/TRITC dual band filter set. Mycobacteria were identified on basis of both fluorescence (strong, medium, weak, no) and morphology (1–10 $\mu$m slender, rod-shaped bacilli. Mycobacteria of the MOTT group may appear pleomorphic, ranging in appearance from long rods to coccoid forms)

Probe concentrations are listed together with the results in Table 6 and 7 (probes targeting mycobacteria of the MTC group) and Table 8 (probes targeting to mycobacteria of the MOTT group).

TABLE 6

| | OK 450 25 nM | OK 682 100 nM | OK 689 100 nM | OK 688 250 nM | OK 660 100 nM |
|---|---|---|---|---|---|
| *M. tuberculosis* | +++ | +++ | +++ | +++ | +++ |
| *M. bovis* BCG | +++ | +++ | +++ | +++ | +++ |
| *M. intracellulare* | – | – | – | – | – |
| *M. avium* | – | – | – | – | – |
| *M. kansasii* | ++ | – | – | – | – |
| *M. gordonae* | – | – | – | – | – |

TABLE 6-continued

| | OK 450 25 nM | OK 682 100 nM | OK 689 100 nM | OK 688 250 nM | OK 660 100 nM |
|---|---|---|---|---|---|
| *M. scrofulaceum* | +++ | – | – | – | – |
| *M. abscessus* | – | – | – | – | + |
| *M. marinum* | +++ | – | + | + | +++ |
| *M. simiae* | – | – | – | – | – |
| *M. szulgai* | +++ | – | – | – | – |
| *M. flavescens* | – | ++ | – | – | – |
| *M. fortuitum* | – | + | – | – | – |
| *M. xenopi* | – | ++ | – | – | – |

+++ strong fluorescence, ++ medium fluorescence, + weak fluorescence. – no fluorescence

TABLE 7

| Mycobacteria | OK 855 150 nM | OK 448 50 nM | OK 654 100 nM | OK 446 25 nM |
|---|---|---|---|---|
| *M. tuberculosis* | +++ | +++ | +++ | +++ |
| *M. bovis* BCG | +++ | +++ | +++ | +++ |
| *M. intracellulare* | – | – | – | – |
| *M. avium* | – | – | – | – |
| *M. kansasii* | – | – | – | – |
| *M. gordonae* | – | – | – | – |
| *M. scrofulaceum* | – | – | – | – |
| *M. abscessus* | – | – | + | – |
| *M. marinum* | – | – | + | +++ |
| *M. simiae* | – | – | – | – |
| *M. szulgai* | – | – | – | – |
| *M. flavescens* | – | – | – | – |
| *M. fortuitum* | – | – | – | – |
| *M. xenopi* | – | – | – | – |

+++ strong fluorescence, ++ medium fluorescence, + weak fluorescence, – no fluorescence

TABLE 8

| Mycobacteria | OK 612 100 nM | OK 624 100 nM | OK 623 100 nM |
|---|---|---|---|
| *M. tuberculosis* | – | – | – |
| *M. bovis* BCG | – | – | – |
| *M. intracellulare* | – | ++ | ++ |
| *M. avium* | +++ | +++ | +++ |
| *M. kansasii* | – | – | +++ |
| *M. gordonae* | – | ++ | ++ |
| *M. scrofulaceum* | – | ++ | ++ |
| *M. abscessus* | – | ++ | +++ |
| *M. marinum* | – | – | – |
| *M. simiae* | – | ++ | +++ |
| *M. szulgai* | – | – | +++ |
| *M. flavescens* | – | – | – |
| *M. fortuitum* | – | ++ | – |
| *M. xenopi* | – | – | – |

+++ strong fluorescence, ++ medium fluorescence, + weak fluorescence, – no fluorescence Each of probes indicated in Table 6, 7 and 8 was further investigated with regard to hybridisation to other common respiratory bacteria, namely Corynebacterium spp., *Fusobacterium nucleatum, Haemophitus influenzae, Klebsiella pneumoniae, Pseudomonas aeruginosa, Propionibacterium acnes, Streptococcuc pneumoniae, Staphyloccus aureus, Brahamella catarrhalis, Escherichia coli,* Neisseria spp., *Actinobacter calcoaceticus,* Actinomyces spp., *Enterobacter aerogenes, Proteus mirabilis, Pseudomonas maltophilia, Streptocussuc viridans,* and *Norcardia asteroides.* No cross-hybridisation was observed by fluorescence in situ hybridisation to any of these bacteria in the case of OK 682, OK 654, OK 655, OK 688, OK 660, OK 612. OK 624 and OK 623. Some cross-reactivity was observed in the case of OK 446 (to *P. acnes*), OK 448 (to *P. acnes* and *B. catarrhalis*), and OK 450 (to *P. acnes* and *B. catarrhalis*).

Table 6 and 7 shows that none of the MTC probes cross-react with *M. intracellulare* and/or *M. avium,* but indeed strongly with *M. tuberculosis* and *M. bovis* BCG. As shown in Table 8, both OK 624 and OK 623 hybridise to *M. intracellulare* and *M. avium* which are both members of the MAC group, whereas none of them hybridise to *M. tuberculosis* or *M. bovis* BCG. OK 612 hybridises to *M. avium* only. It should be noted that the aligned sequence of *M. intracellulare* has just one nucleobase difference to the target sequence of *M. avium,* see FIG. 4K.

The data support the use of the methodology described in claim 3 and 4 and exemplified in Example 2 for design of peptide nucleic acid probes that are capable of hybridising to target sequence of one or more mycobacterium species and not to other mycobacterium species having at least one nucleobase difference to the target sequence.

Example 8

To study the usefulness of the peptide nucleic acid probes in distinguishing between mycobacteria of the MTC group and mycobacteria of the MOTT group, the probes were tested on smears of mycobacterium-positive cultures prepared from 34+28 clinical samples (sputum samples, other respiratory samples and extrapulmonary samples) from individuals suspected of tuberculosis or other mycobacterial infections (kindly provided by the Mycobacterium Department, Statens Serum institut, Denmark). Complex/species Identification data obtained with the AccuProbe tests from Gen-Probe Inc., USA were available for each sample.

Table 9 shows the results obtained with four different peptide nucleic add probes targeting mycobacteria of the MTC group (OK 682, OK 660, OK 688 and OK 689) and one probe targeting mycobacteria of the MOTT group (OK 623), and Table 10 shows the results obtained with two peptide nucleic acid probes targeting mycobacteria of the MOTT group (OK 623 and OK 612) and a mixture of two probes targeting mycobacteria of the MTC group (OK 688 and OK 689). Data are arranged according to the results obtained by AccuProbe. Sample preparation, hybridisation and visualisation were performed as described in Example 7.

TABLE 9

| Complex/ species (n) | OK 623 25 nM $n_p$ | OK 682 100 nM $n_p$ | OK 660 100 nM $n_p$ | OK 688 250 nM $n_p$ | OK 689 100 nM $n_p$ |
|---|---|---|---|---|---|
| MTC (23) | 0 | 23 | 23 | 23 | 23 |
| *M. avium* (5) | 5 | 0 | 0 | 0 | 0 |
| *M. gordonae* (3) | 3 | 0 | 0 | 0 | 0 |
| Unknown (3) | 3 | 0 | 0 | 0 | 0 |

$n_p$ denotes number of positive samples.
The term "unknown" means that the sample not contains mycobacteria of the MTC group, or mycobacteria of the MAC group according the AccuProbe test, but further species identification was not performed.

TABLE 10

| Complex/ species (n) | OK 623 25 nM $n_p$ | OK 612 100 nM $n_p$ | OK 688/OK 689 50 nM/50 nM $n_p$ |
|---|---|---|---|
| MTC (17) | 0 | | 16 |
| *M. avium* (2) | 2 | 2 | 0 |

TABLE 10-continued

| Complex/ species (n) | OK 623 25 nM $n_p$ | OK 612 100 nM $n_p$ | OK 688/OK 689 50 nM/50 nM $n_p$ |
|---|---|---|---|
| *M. gordonae* (4) | 3 | 0 | 0 |
| Unknown (5) | 5 | 0 | 0 |

$n_p$ denotes number of positive samples.
The term "unknown" means that the sample not contains mycobacteria of the MTC group, or mycobacteria of the MAC group according the Accu-Probe test, but further species identification was not performed.

The results shown in Table 9 are in conformity with the complex/species identification performed with the Accu-Probe tests, and thus confirm that peptide nucleic acid probes can be used to determine whether an infection is caused by mycobacteria of the MTC group or by mycobacteria of the MOTT group.

From the results in Table 10, it can be seen that it is possible to differentiate between mycobacteria of the MTC group and mycobacteria of the MOTT group with 100% specificity and 91–94% sensitivity relative to results obtained by the AccuProbe tests. Furthermore, OK 612 is very suitable for specific identification of *M. avium* among those being positive for mycobacteria of the MOTT group as the result is positive in the case of *M. avium* and negative in the other cases of mycobacteria of the MOTT group.

Example 9

Direct detection of mycobacteria in clinical smears of sputum

This example demonstrates the ability of the peptide nucleic acid to detect and identify mycobacteria directly in AFB-positive sputum samples from suspected cases of tuberculosis (kindly provided by Division of Microbiology, Ramathibodi Hospital, Bangkok, Thailand) and suspected cases of other mycobacterial infections (kindly provided by Clinical Microbiology Dept., Rigshospitalet, Copenhagen, Denmark) by FISH is shown.

The clinical smears were prepared according to the procedure described in Example 5, and FISH was performed as described in Example 7. The results are shown in Table 11.

TABLE 11

| Sample no. | OK 623 25 nM | OK 654 100 nM | OK 655 150 nM | OK 682 100 nM | OK 688 250 nM | OK 689 100 nM |
|---|---|---|---|---|---|---|
| 1 | – | ++ | ++ | ++ | ++ | ++ |
| 175 | – | ++ | nd | nd | ++ | ++ |
| 459 | – | – | nd | nd | – | – |
| 166 | – | – | – | nd | – | – |
| 268 | – | ++ | ++ | ++ | ++ | ++ |
| 34267 | ++ | – | – | – | – | – |

nd: not determined
+++ strong fluorescence, ++ medium fluorescence, + weak fluorescence, – no fluorescence It appears from examples in Table 11 that AFB-positive sputum smears were evaluated positive for mycobacteria of the MTC group (sample numbers 1, 175, and 268), positive for mycobacteria of the MOTT group (sample number 37267), or negative for mycobacteria (sample numbers 459 and 166) by the applied probes. Thus, PNA-probes are useful reagents for specific identification of mycobacteria directly in sputum smears by fluorescence in situ hybridisation. AFB-positive sputum samples that are negative with all probes may be explained in three ways: a) the sample may contain mycobacteria not detected by the probes, e.g. *M. fortuitum,* b) the sample may contain other acid-fast bacteria than mycobacteria, or c) the mycobacteria in the sample lack or have a strongly reduced content of rRNA due to for example antibiotic treatment.

In conclusion, direct identification of mycobacteria in smear-positive sputum samples by peptide nucleic acid-based fluorescence in situ hybridisation combines simplicity and morphological advantages of current staining methods with concomitant species identification, and will thus allow clinical microbiology laboratories to benefit from the advantages offered by molecular techniques to provide crucial information pertaining to therapy and patient management.

Example 10

This example demonstrates simultaneous detection and identification of mycobacteria of the MTC group and mycobacteria of the MOTT group using differently labelled probes targeting mycobacteria of the MTC group and mycobacteria of the MOTT group respectivety, by fluorescence in situ hybridisation.

Control smears of different mycobacterium species were prepared as described in Example 5. In addition, smears containing a mixture of *M. tuberculosis* and *M. avium* were prepared (Table 8. last row). FISH was performed as described in Example 7.

A rhodamine-labelled peptide nucleic acid probe targeting 16S rRNA of mycobacteria of the MTC group (OK 702) and a fluorescein-labelled peptide nucleic acid probe targeting 16S rRNA of mycobacteria of the MOTT group (OK 623) were applied simultaneously in the concentrations listed in Table 12 together with the results.

TABLE 12

| Mycobacterium species | OK 623/OK 702 25/250 nM |
|---|---|
| *M. tuberculosis* | –(G)/+++(R) |
| *M. bovis* BCG | –(G)/+++(R) |
| *M. avium* | +++(G)/–(R) |
| *M. intracellulare* | +++(G)/–(R) |
| *M. kansasii* | +++(G)/–(R) |
| *M. avium/M. tuberculosis* | +++(G)/+++(R) |

+++ strong fluorescence – no fluorescence
G green fluorescence, R red fluorescence Mycobacteria of the MTC group. i.e. *M. tuberculosis* and *M. bovis,* were observed as green fluorescent mycobacteria, whereas mycobacteria of the MOTT group, i.e. *M. avium, M. intracellulare* and *M. kansasii,* were observed as red fluorescent mycobacteria. Mycobacteria in the *M. avium/M. tuberculosis* mixture were identified by a mixture of both green fluorescent mycobacteria and red fluorescent mycobacteria.

The results show that it is possible to distinguish between different Mycobacterium species in one smear using a mixture of differently labelled probes. Such simultaneous detection and identification of mycobacteria may further be extended to comprise three or more differently labelled peptide nucleic acid probes.

Example 11

The ability of a peptide nucleic acid probes to hybridise to precursor rRNA and further to distinguish between precursor rRNA of *M. tuberculosis* and precursor rRNA of *M. avium* was investigated by fluorescence in situ hybridisation.

Smears were prepared as described in Example 5 and FISH were carried out as described in Example 7 using a fluorescein-labelled probe targeting precursor rRNA of *M. tuberculosis* (OK 749). The results are given in Table 13.

TABLE 13

| Mycobacterium | OK 749 1000 nM |
|---|---|
| *M. tuberculosis* | + |
| *W. avium* | – |

+ weak fluorescence – no fluorescence

From the results, it can be concluded that it is possible to detect precursor rRNA, and further that is possible to distinguish between precursor rRNA from different mycobacterium species. The application of peptide nucleic acid targeting precursor rRNA may be particularly useful for measuring the mycobacterial growth and thus be an indicator of the viability of the mycobacteria. This would in particular be important for monitoring of the effect of antibiotics in relation to both treatment of tuberculosis and drug susceptibility studies.

Example 12

The ability of peptide nucleic acid probes for differentiation of drug susceptible and drug resistant mycobacteria was evaluated using a fluorescein-labelled probe targeting the wild type sequence of 23S rRNA of *M. avium* and *M. intracellulare* together with rhodamine-labelled probes targeting single point mutations associated with macrolide resistance in *M. avium* and *M. intracellulare.*

Smears were prepared as described in Example 5 from cultures of *M. avium* (ATCC no. 25292) and *M. intracellulare* (ATCC no. 13950). These strains are anticipated to contain the wild type sequence of rRNA. Macrolide resistant variants were not available. FISH was carried out as described in Example 7 using a fluorescein-labelled peptide nucleic acid probe targeting wild type 23S rRNA (OK 745) and a mixture of rhodamine-labelled peptide nucleic acid probes targeting the three possible mutations at position 2568 (OK 746) and at position 2569 (OK 747) of *M. avium* 23S rDNA of GenBank entry X52917 (see FIG. 6). The results are given in Table 14.

TABLE 14

| Mycobacterium species | OK 745/OK 746/OK 747 500/500/500 nM |
|---|---|
| *M. avium* (wild type) | +++(G)/–(R) |
| *M. intracellulare* (wild type) | +++(G)/–(R) |

+++strong fluorescence – no fluorescence
G green fluorescence, R red fluorescence
OK 746 and OK 747 are each a mixture of three single point mutation probes The results in Table 14 show that *M. avium* and *M. intracellulare* are detected with the fluorescein-labelled probe (OK 745) targeting *M. avium* and *M. intracellulare* wild types and not detected with the mixture of rhodamine-labelled probes (OK 746 and OK 747) targeting single point mutations associated with macrolide resistance. Such peptide nucleic acid probes targeting the wild type and drug resistant variants, respectively, may be important tools for both the prediction of an efficient therapy as well as for monitoring the effect of the treatment.

Example 13

To illustrate the speed with which peptide nucleic acid probes penetrate the mycobacterial cell wall and subsequently hybridise to their target sequence the protocol described in Example 7 was modified to 15 minutes hybridisation time and the results compared with 90 minutes hybridisation time. Smears were prepared as described in Example 5. The results are given in Table 15.

TABLE 15

| | OK 623 25 nM | | OK 689 100 nM | |
|---|---|---|---|---|
| | 15 min | 90 min | 15 min | 90 min |
| *M. tuberculosis* | | | ++ | +++ |
| *M. avium* | ++ | +++ | | |

+++ strong fluorescence ++ medium fluorescence + weak fluorescence – no fluorescence The data presented in Table 15 show that hybridisation by peptide nucleic acid probes inside the mycobacterial cells is accomplished in a very short time resulting in a detectable signal after just 15 minutes incubation. Thus, the use peptide nucleic acid probes makes possible the development of very fast fluorescence in situ hybridisation protocols.

Example 14

To describe the ability of very short peptide nucleic acid probes to hybridise to target sequences, a 12-mer peptide nucleic acid probe labelled with fluorescein (OK 575) was tested by fluorescence in situ hybridisation (FISH).

Smears were prepared as described in Example 5 and FISH were carried out as described in Example 7. The results are given in Table 16.

TABLE 16

| Mycobacterium | OK 575 50 nM |
|---|---|
| *M. tuberculosis* | + |
| *M. bovis* BCG | ++ |
| *M. avium* | – |
| *M. intracellulare* | – |
| *M. kansasii* | – |

++ medium fluorescence + weak fluorescence – no fluorescence

The results in table 17 shows that a 12-mer peptide nucleic acid probe is capable of hybridising specifically to target sequences under the same stringency conditions as 15-mers. A lower florescence intensity is obtained as the $T_m$ for a 12-mer peptide nucleic acid probe is lower than $T_m$ for a 15-mer peptide nucleic acid probe.

The date clearly suggest that by lowering the stringency condition, e.g. by decreasing the hybridisation/washing temperature and/or the concentration of formamide, even shorter probes may be applied for detection of mycobacteria provided that specific sequences of such can be designed.

What is claimed is:

1. A peptide nucleic acid probe comprising from 15 to 30 polymerized moieties of formula (I)

(I)

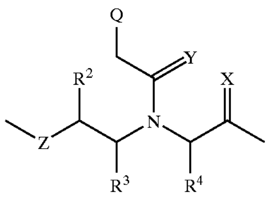

wherein each X and Y are independently chosen from O and S, each Z independently is chosen from O, S, $NR^1$, and $C(R^1)_2$, wherein each $R^1$ is independently chosen from H, $C_{1-6}$ alkyl, $C_{1-6}$ alkenyl, and $C_{1-6}$ alkynyl, each $R^2$, $R^3$ and $R^4$ are independently chosen from H, the side chain of a naturally occurring amino acid, the side chain of a non-naturally occurring amino acid, $C_{1-4}$ alkyl, $C_{1-4}$ alkenyl, $C_{1-4}$ alkynyl, and a functional group, and each Q is independently chosen from a naturally occurring nucleobase, a non-naturally occurring nucleobase, an intercalator, a nucleobase-binding group, a label and H, wherein a series of Qs of adjacent moieties are chosen so as to form one of the following subsequences

| | |
|---|---|
| GGC TTT TAA GGA TTC | (SEQ ID NO: 40) |
| GAT CAA TGC TCG GTT | (SEQ ID NO: 44) |
| CGA CTC CAC ACA AAC | (SEQ ID NO: 76) |
| GTC TTT TCG TCC TGC | (SEQ ID NO: 89), or |
| GTC TTA TCG TCC TGC | (SEQ ID NO: 90) |

or a mixture of such probes.

2. The peptide nucleic acid probe of claim 1, wherein each of the 15 to 30 polymerized moieties of formula (I) are independently chosen from (II)

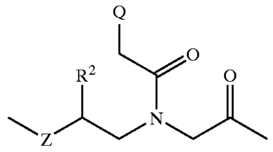

(III)

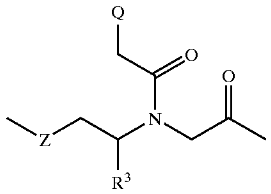

(IV)

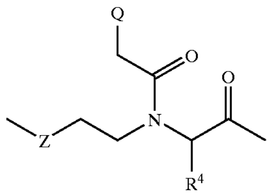

or a mixture of such probes.

3. The peptide nucleic acid probe according to claim 1, wherein each Z is independently chosen from NH, $NCH_3$ and O, and each $R^2$, $R^3$ and $R^4$ is independently chosen from H, the side chain of a naturally occurring amino acid, the side chain of a non-naturally occurring amino acid, and $C_{1-4}$ alkyl, or a mixture of such probes.

4. The peptide nucleic acid probe according to claim 1, wherein each Z is independently chosen from NH and O, and each $R^2$ is independently chosen from H or the side chain of Ala, Asp, Cys, Glu, His, HomoCys, Lys, Orn, Ser and Thr, or a mixture of such probes.

5. The peptide nucleic acid probe of claim 1, further comprising one or more labels, or a mixture of such probes, which labels may be mutually identical or different, which probes may comprise one or more linkers, and which probes may be mutually identical or different.

6. The peptide nucleic acid probe of claim 1 chosen from

| | |
|---|---|
| Lys(Flu)-GGC TTT TAA GGA TTC-$NH_2$ | (OK 689/modified SEQ ID NO: 40) |
| Lys(Rho)-GGC TTT TAA GGA TTC-$NH_2$ | (OK 702/modified SEQ ID NO: 40) |
| Flu-β-Ala-β-Ala-GAT CAA TGC TCG GTT-$NH_2$ | (OK 624/modified SEQ ID NO: 44) |
| Flu-β-Ala-β-Ala-CGA CTC CAC ACA AAC-$NH_2$ | (OK 612/modified SEQ ID NO: 76) |
| Lys(Flu)-GTC TTT TCG TCC TGC-$NH_2$ | (OK 745/modified SEQ ID NO: 89) |
| Lys(Rho)-GTC TTA TCG TCC TGC-$NH_2$ | (OK 746/modified SEQ ID NO: 90) |

wherein Flu denotes a 5-(and 6)-carboxyfluoroescein label and Rho denotes a rhodamine label, or a mixture of such probes.

7. A kit comprising:

at least one peptide nucleic acid probe comprising from 15 to 30 polymerized moieties of formula (I)

(I)

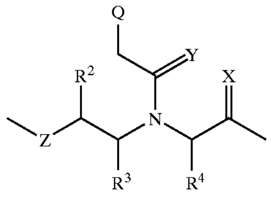

wherein each X and Y are independently chosen from O and S, each Z independently is chosen from O, S, $NR^1$, and $C(R^1)_2$, wherein each $R^1$ is independently chosen from H, $C_{1-6}$ alkyl, $C_{1-6}$ alkenyl, and $C_{1-6}$ alkynyl, each $R^2$, $R^3$ and $R^4$ are independently chosen from H, the side chain of a naturally occurring amino acid, the side chain of a non-naturally occurring amino acid, $C_{1-4}$ alkyl, $C_{1-4}$ alkenyl, $C_{1-4}$ alkynyl, and a functional group, and each Q is independently chosen from a naturally occurring nucleobase, a non-naturally occurring nucleobase, an intercalator, a nucleobase-binding group, a label or H, wherein a series of Qs of adjacent moieties are chosen so as to form one of the following subsequences

| | |
|---|---|
| GGC TTT TAA GGA TTC | (SEQ ID NO: 40) |
| GAT CAA TGC TCG GTT | (SEQ ID NO: 44) |
| CGA CTC CAC ACA AAC | (SEQ ID NO: 76) |
| GTC TTT TCG TCC TGC | (SEQ ID NO: 89), or |
| GTC TTA TCG TCC TGC | (SEQ ID NO: 90) |

and a detection system with at least one detecting reagent.

8. The kit of claim 7 comprising a mixture of the at least one peptide nucleic acid probe.

9. The kit of claim 7, further comprising a solid phase capture system.

* * * * *

SEQUENCE LISTING (1) GENERAL INFORMATION:

(iii) NUMBER OF SEQUENCES: 123

(2) INFORMATION FOR SEQ ID NO: 1:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 1:

AGATCGGGGT AGCAC 15

(2) INFORMATION FOR SEQ ID NO: 2:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 2:

TGTTTTCTCC TCCTA 15

(2) INFORMATION FOR SEQ ID NO: 3:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 3:

ACTGCCTCTC AGCCG 15

(2) INFORMATION FOR SEQ ID NO: 4:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 4:

TGATACTAGG CAGGT 15

(2) INFORMATION FOR SEQ ID NO: 5:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 5:

CGGATTCACA GCGGA 15

(2) INFORMATION FOR SEQ ID NO: 6:

(i) SEQUENCE CHARACTERISTICS:
(A) LENGTH: 15 basepairs
(B) TYPE: nucleic acid basepairs
(C) STRANDEDNESS: single -continued (D) TOPOLOGY: linear (xi) SEQUENCE DESCRIPTION: SEQ ID NO: 6:

TCACCACCCT CCTCC 15

(2) INFORMATION FOR SEQ ID NO: 7:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 7:

TTAACCTTGC GACAT 15

(2) INFORMATION FOR SEQ ID NO: 8:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 8:

ACTATTCACA CGCGC 15

(2) INFORMATION FOR SEQ ID NO: 9:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 9:

CTCCGCGGTG AACCA 15

(2) INFORMATION FOR SEQ ID NO: 10:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 10

GCTTTACACC ACGGC 15

(2) INFORMATION FOR SEQ ID NO: 11:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 11:

ACGCTTGGGG GCCTT 15

(2) INFORMATION FOR SEQ ID NO: 12:

(i) SEQUENCE CHARACTERISTICS:
(A) LENGTH: 15 basepairs
(B) TYPE: nucleic acid basepairs
(C) STRANDEDNESS: single
(D) TOPOLOGY: linear -continued (xi) SEQUENCE DESCRIPTION: SEQ ID NO: 12:

CCACACCCAC CACAA 15

(2) INFORMATION FOR SEQ ID NO: 13:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 13:

CCGGTGGCTT CGCTG 15

(2) INFORMATION FOR SEQ ID NO: 14:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 14:

ACTTGCCTTG TCGCT 15

(2) INFORMATION FOR SEQ ID NO: 15:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 15:

GATTCGTCAC GGGCG 15

(2) INFORMATION FOR SEQ ID NO: 16:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 16:

AACTCCACAC CCCCG 15

(2) INFORMATION FOR SEQ ID NO: 17:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 17:

ACTCCACACC CCCGA 15

(2) INFORMATION FOR SEQ ID NO: 18:

(i) SEQUENCE CHARACTERISTICS:
(A) LENGTH: 15 basepairs
(B) TYPE: nucleic acid basepairs
(C) STRANDEDNESS: single
(D) TOPOLOGY: linear -continued (xi) SEQUENCE DESCRIPTION: SEQ ID NO: 18:

ACCCCTTCGC TTGAC 15

(2) INFORMATION FOR SEQ ID NO: 19:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 19:

CTTGCCCCAG TGTTA 15

(2) INFORMATION FOR SEQ ID NO: 20:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 20:

CTCTCCCTAC CGGCT 15

(2) INFORMATION FOR SEQ ID NO: 21:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 21:

GATATTCCGG TCCCC 15

(2) INFORMATION FOR SEQ ID NO: 22:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 22:

ACTCCGCCCC AACTG 15

(2) INFORMATION FOR SEQ ID NO: 23:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 23:

CTGTCCCTAA ACCCG 15

(2) INFORMATION FOR SEQ ID NO: 24:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 24:

-continued

TTCGAGGTTA GATGC 15

(2) INFORMATION FOR SEQ ID NO: 25:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 25:

GTCCCTAAAC CCGAT 15

(2) INFORMATION FOR SEQ ID NO: 26:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 26:

GGTGCACCAG AGGTT 15

(2) INFORMATION FOR SEQ ID NO: 27:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 27:

CTGGCGGGAC AACTG 15

(2) INFORMATION FOR SEQ ID NO: 28:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 28:

TTATCCTGAC CGAAC 15

(2) INFORMATION FOR SEQ ID NO: 29:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 29:

GACCTATTGA ACCCG 15

(2) INFORMATION FOR SEQ ID NO: 30:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 30:

-continued

GAAGAGACCT TTCCG 15

(2) INFORMATION FOR SEQ ID NO: 31:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 31:

CACTCGAGTA TCTCC 15

(2) INFORMATION FOR SEQ ID NO: 32:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 32:

ATCACCCACG TGTTA 15

(2) INFORMATION FOR SEQ ID NO: 33:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 33:

GCATCCCGTG GTCCT 15

(2) INFORMATION FOR SEQ ID NO: 34:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 34:

CACAAGACAT GCATC 15

(2) INFORMATION FOR SEQ ID NO: 35:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 35:

TAAAGCGCTT TCCAC 15

(2) INFORMATION FOR SEQ ID NO: 36:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 36:

GCTCATCCCA CACCG 15

-continued (2) INFORMATION FOR SEQ ID NO: 37:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 37:

CCGAGAGAAC CCGGA 15

(2) INFORMATION FOR SEQ ID NO: 38:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 38:

AGTCCCCACC ATTAC 15

(2) INFORMATION FOR SEQ ID NO: 39:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 39:

AACCTCGCGG CATCG 15

(2) INFORMATION FOR SEQ ID NO: 40:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 40:

GGC TTTTAAG GATTC 15

(2) INFORMATION FOR SEQ ID NO: 41:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 41:

GACCCCGATC CGAAC 15

(2) INFORMATION FOR SEQ ID NO: 42:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 42:

CCGACTTCAC GGGGT 15

-continued (2) INFORMATION FOR SEQ ID NO: 43:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 43:

CGGAGGGGCA GTATC 15

(2) INFORMATION FOR SEQ ID NO: 44:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 44:

GATCAATGCT CGGTT 15

(2) INFORMATION FOR SEQ ID NO: 45:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 45:

TTCCCCGCGT TACCT 15

(2) INFORMATION FOR SEQ ID NO: 46:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 46:

TTAGCCTGTT CCGGT 15

(2) INFORMATION FOR SEQ ID NO: 47:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 47:

GCATGCGGTT TAGCC 15

(2) INFORMATION FOR SEQ ID NO: 48:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 48:

TACCCGGTTG TCCAT 15

-continued (2) INFORMATION FOR SEQ ID NO: 49:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 49:

GTAGAGCTGA GACAT 15

(2) INFORMATION FOR SEQ ID NO: 50:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 50:

GCCGTCCCAG GCCAC 15

(2) INFORMATION FOR SEQ ID NO: 51:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 51:

CTCGGGTGTT GATAT 15

(2) INFORMATION FOR SEQ ID NO: 52:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 52:

ACTATTTCAC TCCCT 15

(2) INFORMATION FOR SEQ ID NO: 53:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 53:

ACGCCATCAC CCCAC 15

(2) INFORMATION FOR SEQ ID NO: 54:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 54:

CGACGTGTCC CTGAC 15

(2) INFORMATION FOR SEQ ID NO: 55:

-continued (i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 55:

ACTACACCCC AAAGG 15

(2) INFORMATION FOR SEQ ID NO: 56:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 56:

CACGCTTTTA CACCA 15

(2) INFORMATION FOR SEQ ID NO: 57:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 57:

GCGACTACAC ATCCT 15

(2) INFORMATION FOR SEQ ID NO: 58:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 58:

CGGCGCATAA TCACT 15

(2) INFORMATION FOR SEQ ID NO: 59:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 59:

CCACATCCAC CGTAA 15

(2) INFORMATION FOR SEQ ID NO: 60:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 60:

CGCTGAATGG GGGAC 15

(2) INFORMATION FOR SEQ ID NO: 61:

-continued (i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 61:

GGAGCTTCGC TGAAT 15

(2) INFORMATION FOR SEQ ID NO: 62:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 62:

CGGTCACCCG GAGCT 15

(2) INFORMATION FOR SEQ ID NO: 63:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 63:

GGACGCCCAT ACACG 15

(2) INFORMATION FOR SEQ ID NO: 64:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 64:

GAAGGGGAAT GGTCG 15

(2) INFORMATION FOR SEQ ID NO: 65:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 65:

AATCGCCACG CCCCC 15

(2) INFORMATION FOR SEQ ID NO: 66:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 66:

CAGCGAAGGT CCCAC 15

(2) INFORMATION FOR SEQ ID NO: 67:

(i) SEQUENCE CHARACTERISTICS:

-continued (A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 67:

GTCACCCCAT TGCTT 15

(2) INFORMATION FOR SEQ ID NO: 68:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 68:

ATCGCTCTCT ACGGG 15

(2) INFORMATION FOR SEQ ID NO: 69:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 69:

GTGTATGTGC TCGCT 15

(2) INFORMATION FOR SEQ ID NO: 70:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 70:

ACGGTATTCC GGGCC 15

(2) INFORMATION FOR SEQ ID NO: 71:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 71:

GGCCGAATCC CGCTC 15

(2) INFORMATION FOR SEQ ID NO: 72:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 72:

AAACAGTCGC TACCC 15

(2) INFORMATION FOR SEQ ID NO: 73:

(i) SEQUENCE CHARACTERISTICS:
(A) LENGTH: 15 basepairs

-continued (B) TYPE: nucleic acid basepairs
(C) STRANDEDNESS: single
(D) TOPOLOGY: linear (xi) SEQUENCE DESCRIPTION: SEQ ID NO: 73:

CCTTACGGGT TAACG 15

(2) INFORMATION FOR SEQ ID NO: 74:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 74:

GAGACAGTTG GGAAG 15

(2) INFORMATION FOR SEQ ID NO: 75:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 75:

TGGCGTCTGT GCTTC 15

(2) INFORMATION FOR SEQ ID NO: 76:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 76:

CGACTCCACA CAAAC 15

(2) INFORMATION FOR SEQ ID NO: 77:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 77:

GATAAGGGTT CGACG 15

(2) INFORMATION FOR SEQ ID NO: 78:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 78:

ATCCGTTGAG TGACA 15

(2) INFORMATION FOR SEQ ID NO: 79

(i) SEQUENCE CHARACTERISTICS:
(A) LENGTH: 15 basepairs
(B) TYPE: nucleic acid basepairs -continued (C) STRANDEDNESS: single
(D) TOPOLOGY: linear (xi) SEQUENCE DESCRIPTION: SEQ ID NO: 79:

CAGCCCGTTA TCCCC 15

(2) INFORMATION FOR SEQ ID NO: 80:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 80:

AACCTTTGGG ACCTG 15

(2) INFORMATION FOR SEQ ID NO: 81:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 81:

TAAAAGGGTG AGAAA 15

(2) INFORMATION FOR SEQ ID NO: 82:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 82:

GTCTGGCCTA TCAAT 15

(2) INFORMATION FOR SEQ ID NO: 83:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 83:

AGATTGCCCA CGTGT 15

(2) INFORMATION FOR SEQ ID NO: 84

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 84:

AATCCGAGAA AACCC 15

(2) INFORMATION FOR SEQ ID NO: 85:

(i) SEQUENCE CHARACTERISTICS:
(A) LENGTH: 15 basepairs
(B) TYPE: nucleic acid basepairs
(C) STRANDEDNESS: single -continued (D) TOPOLOGY: linear (xi) SEQUENCE DESCRIPTION: SEQ ID NO: 85:

GCATTACCCG CTGGC 15

(2) INFORMATION FOR SEQ ID NO: 86:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 86:

TTAAAAGGAT TCGCT 15

(2) INFORMATION FOR SEQ ID NO: 87:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 87:

AGACCCCAAT CCGAA 15

(2) INFORMATION FOR SEQ ID NO: 88:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 88:

GACTCCGACT TCATG 15

(2) INFORMATION FOR SEQ ID NO: 89:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 89:

GTCTTTTCGT CCTGC 15

(2) INFORMATION FOR SEQ ID NO: 90:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 90:

GTCTTATCGT CCTGC 15

(2) INFORMATION FOR SEQ ID NO: 91:

(i) SEQUENCE CHARACTERISTICS:
(A) LENGTH: 15 basepairs
(B) TYPE: nucleic acid basepairs
(C) STRANDEDNESS: single
(D) TOPOLOGY: linear -continued (xi) SEQUENCE DESCRIPTION: SEQ ID NO: 91:

GTCTTCTCGT CCTGC 15

(2) INFORMATION FOR SEQ ID NO: 92:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 92:

GTCTTGTCGT CCTGC 15

(2) INFORMATION FOR SEQ ID NO: 93:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 93:

GTCTATTCGT CCTGC 15

(2) INFORMATION FOR SEQ ID NO: 94:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 94:

GTCTCTTCGT CCTGC 15

(2) INFORMATION FOR SEQ ID NO: 95:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 95:

GTCTGTTCGT CCTGC 15

(2) INFORMATION FOR SEQ ID NO: 96:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 96:

TTGGCCGGTG CTTCT 15

(2) INFORMATION FOR SEQ ID NO: 97:

(i) SEQUENCE CHARACTERISTICS:
(A) LENGTH: 15 basepairs
(B) TYPE: nucleic acid basepairs
(C) STRANDEDNESS: single
(D) TOPOLOGY: linear -continued (xi) SEQUENCE DESCRIPTION: SEQ ID NO: 97:

TTGGCCGGTA CTTCT 15

(2) INFORMATION FOR SEQ ID NO: 98:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 98:

TTGGCCGGTC CTTCT 15

(2) INFORMATION FOR SEQ ID NO: 99:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 99:

TTGGCCGGTT CTTCT 15

(2) INFORMATION FOR SEQ ID NO: 100:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 100:

ACCGCGGCTG CTGGC 15

(2) INFORMATION FOR SEQ ID NO: 101:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 101:

ACCGCGGCTA CTGGC 15

(2) INFORMATION FOR SEQ ID NO: 102:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 102:

ACCGCGGCTC CTGGC 15

(2) INFORMATION FOR SEQ ID NO: 103:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 103:

-continued

ACCGCGGCTT CTGGC 15

(2) INFORMATION FOR SEQ ID NO: 104:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 104:

CGGCAGCTGG CACGT 15

(2) INFORMATION FOR SEQ ID NO: 105:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 105:

CGGCCGCTGG CACGT 15

(2) INFORMATION FOR SEQ ID NO: 106:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 106:

CGGCTGCTGG CACGT 15

(2) INFORMATION FOR SEQ ID NO: 107:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 107:

CGTATTACCG CAGCT 15

(2) INFORMATION FOR SEQ ID NO: 108:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 108:

CGTATTACCG CCGCT 15

(2) INFORMATION FOR SEQ ID NO: 109:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 109:

-continued

CGTATTACCG CTGCT 15

(2) INFORMATION FOR SEQ ID NO: 110:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 110:

TTCCTTTGAG TTTTA 15

(2) INFORMATION FOR SEQ ID NO: 111

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 111:

TTCCTTTAAG TTTTA 15

(2) INFORMATION FOR SEQ ID NO: 112:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 112:

TTCCTTTCAG TTTTA 15

(2) INFORMATION FOR SEQ ID NO: 113:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 113:

TTCCTTTTAG TTTTA 15

(2) INFORMATION FOR SEQ ID NO: 114:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 114:

TTCCTTAGAG TTTTA 15

(2) INFORMATION FOR SEQ ID NO: 115:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 115:

TTCCTTCGAG TTTTA 15

-continued (2) INFORMATION FOR SEQ ID NO: 116:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 116:

TTCCTTGGAG TTTTA 15

(2) INFORMATION FOR SEQ ID NO: 117:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 117:

CATGTGTCCT GTGGT 15

(2) INFORMATION FOR SEQ ID NO: 118:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 118:

CGTCAGCCCG AGAAA 15

(2) INFORMATION FOR SEQ ID NO: 119:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 119:

CACTACACAC GCTCG 15

(2) INFORMATION FOR SEQ ID NO: 120:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 120:

TGGCGTTGAG GTTTC 15

(2) INFORMATION FOR SEQ ID NO: 121:

(i) SEQUENCE CHARACTERISTICS:
(A) LENGTH: 15 basepairs
(B) TYPE: nucleic acid basepairs
(C) STRANDEDNESS: single
(D) TOPOLOGY: linear (xi) SEQUENCE DESCRIPTION: SEQ ID NO: 121:

GTCCGTGAAC CCGAT 15

-continued

```
(2) INFORMATION FOR SEQ ID NO: 122:

    (i) SEQUENCE CHARACTERISTICS:
        (A) LENGTH: 15 basepairs
        (B) TYPE: nucleic acid basepairs
        (C) STRANDEDNESS: single
        (D) TOPOLOGY: linear

   (xi) SEQUENCE DESCRIPTION: SEQ ID NO: 122:

TACGCTCTTT GAGCT                                                    15


(2) INFORMATION FOR SEQ ID NO: 123:

    (i) SEQUENCE CHARACTERISTICS:
        (A) LENGTH: 15 basepairs
        (B) TYPE: nucleic acid basepairs
        (C) STRANDEDNESS: single
        (D) TOPOLOGY: linear

   (xi) SEQUENCE DESCRIPTION: SEQ ID NO: 123:

AACACTCCCT TTGGA                                                    15
```